US012630601B2

(12) United States Patent
Coffin et al.

(10) Patent No.: US 12,630,601 B2
(45) Date of Patent: May 19, 2026

(54) PROCESS FOR PREPARING A GIP/GLP1 DUAL AGONIST

(71) Applicant: Eli Lilly and Company, Indianapolis, IN (US)

(72) Inventors: Stephanie Ruth Coffin, Plainfield, IN (US); Michael Eugene Kopach, Greenwood, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/800,436

(22) Filed: Aug. 12, 2024

(65) Prior Publication Data

US 2024/0391975 A1 Nov. 28, 2024

Related U.S. Application Data

(62) Division of application No. 17/310,247, filed as application No. PCT/US2020/015353 on Jan. 28, 2020.

(60) Provisional application No. 62/818,342, filed on Mar. 14, 2019, provisional application No. 62/815,053, filed on Mar. 7, 2019, provisional application No. 62/797,963, filed on Jan. 29, 2019.

(51) Int. Cl.

| | |
|---|---|
| ***C07K 14/605*** | (2006.01) |
| ***C07C 233/47*** | (2006.01) |
| ***C07C 271/22*** | (2006.01) |
| ***C07K 1/113*** | (2006.01) |
| ***C07K 14/00*** | (2006.01) |

(52) U.S. Cl.

CPC .......... *C07K 14/605* (2013.01); *C07C 233/47* (2013.01); *C07C 271/22* (2013.01); *C07K 1/113* (2013.01); *C07K 14/001* (2013.01)

(58) Field of Classification Search

None

See application file for complete search history.

(56) References Cited

U.S. PATENT DOCUMENTS

| | | | |
|---|---|---|---|
| 8,129,343 B2 | 3/2012 | Lau et al. | |
| 9,474,780 B2 * | 10/2016 | Bokvist | A61P 43/00 |
| 2011/0313131 A1 | 12/2011 | Carl et al. | |
| 2017/0114115 A1 | 4/2017 | Alsina-Fernandez et al. | |

FOREIGN PATENT DOCUMENTS

| | | | | |
|---|---|---|---|---|
| CN | 104356224 A | | 2/2015 | |
| CN | 108676086 A | * | 10/2018 | C07K 14/605 |
| CN | 108676087 A | * | 10/2018 | C07K 14/605 |
| WO | 200147816 A1 | | 12/2007 | |
| WO | 2009115469 A1 | | 9/2009 | |
| WO | 2010029159 | | 3/2010 | |
| WO | 2010125079 | | 11/2010 | |
| WO | 2011006644 A2 | | 1/2011 | |
| WO | 2011095989 A2 | | 8/2011 | |
| WO | 2015052088 A1 | | 4/2015 | |
| WO | 2016046753 A1 | | 3/2016 | |
| WO | 2016067271 A1 | | 5/2016 | |
| WO | 2016111971 | | 7/2016 | |
| WO | 2016111971 A1 | | 7/2016 | |
| WO | 2021034815 A1 | | 2/2021 | |

OTHER PUBLICATIONS

Coin et al. "Depsipeptide Methodology for Solid-Phase Peptide Synthesis: Circumventing Side Reactions and Development of an Automated Technique via Depsidipeptide Units," J. Org. Chem. 2006, 71, 6171-6177 (Year: 2006).*

Coin "The depsipeptide method for solid-phase synthesis of difficult peptides," J. Pept. Sci. 2010, 16: 223-230 (Year: 2010).*

Coskun et al. "LY3298176, a novel dual GIP and GLP-1 receptor agonist for the treatment of type 2 diabetes mellitus: From discovery to clinical proof of concept," Molecular Metabolism 18 (2018) 3-14 (Year: 2018).*

Frias et al. "Efficacy and safety of LY3298176, a novel dual GIP and GLP-1 receptor agonist, in patients with type 2 diabetes: a randomised, placebo-controlled and active comparator-controlled phase 2 trial," The Lancet, vol. 392, Issue 10160, 2180-2193 (Year: 2018).*

Machine translation to English of CN108676086B downloaded from Google Patents on Jan. 7, 2025. (Year: 2025).*

Machine translation to English of CN108676087B downloaded from Google Patents on Jan. 7, 2025. (Year: 2025).*

Mant et al. HPLC analysis and purification of peptides. Methods Mol Biol. 2007;386:3-55. doi: 10.1007/978-1-59745-430-8_1. PMID: 18604941; PMCID: PMC7119934. (Year: 2007).*

Yang, Chapter 4—Peptide Rearrangement Side Reactions, Editor(s): Yi Yang, Side Reactions in Peptide Synthesis, Academic Press, 2016, pp. 77-93 (Year: 2016).*

International Search Report of the International Searching Authority pertaining to International Application No. PCT/US2020/015353; Date of Mailing: Jun. 24, 2020; 10 pages.

Mroz, Piotr A., et al. "Optimized GIP analogs promote body weight lowering in mice through GIPR agonism not antagonism." Molecular Metabolism 20 (2019): 51-62.

Nyfeler, Rolf. "Peptide synthesis via fragment condensation." Peptide Synthesis Protocols (1995): 303-316.

Written Opinion of the International Search Report of the International Searching Authority pertaining to International Application No. PCT/US2020/015353; Date of Mailing: Jun. 24, 2020; 11 pages.

Zompra et al, "Manufacturing Peptides as Active Pharmaceutical Ingredients", Future Medicinal Chemistry: Future Science, May 1, 2009, pp. 361-377, vol. 1, No. 2.

(Continued)

*Primary Examiner* — Christina Bradley

(74) *Attorney, Agent, or Firm* — Parker D. McCrary; MaCharri R. Vorndran-Jones

(57) ABSTRACT

The present invention provides novel intermediates and processes useful in the manufacture of tirzepatide, or a pharmaceutically acceptable salt thereof.

5 Claims, No Drawings

Specification includes a Sequence Listing.

(56) References Cited

OTHER PUBLICATIONS

Goodwin et al, "Peptides As Therapeutics with Enhanced Bioactivity", Current Medicinal Chemistry, Dec. 31, 2012, pp. 4451-4461, vol. 19, No. 26.
Frederick et al, "Kilogram-Scale GMP Manufacture of Tirzepatide Using a Hybrid SPPS/LPPS Approach with Continuous Manufacturing", American Chemical Society: Organic Process Research and Development, Jun. 17, 2021, pp. 1628-1636, vol. 25, No. 7.
European Search Report of EP20707971 (filed Jan. 28, 2020 by Eli Lilly and Company), Search completed on Feb. 24, 2025, Mailed on Mar. 4, 2025 by the European Patent Office, 19 pages.
Richard Raz, et al. "HF-Free Boc Synthesis of Peptide Thioesters for Ligation and Cyclization", Angewandte Chemie, Wiley-VCH, 2016, vol. 128 Issue: 42 pp. 13368-13373.
Yahson Fernando and Varela Quitián, "Obtaining a High Molecular Weight Chimeric Peptide Derived From *Plasmodium falciparum* Proteins", National University of Colombia, Department of Chemistry, 2016.
Dou, et al., "Expression, purification, and characterization of recombinant human serum albumin fusion protein with two human glucagon-like peptide-1 mutants in Pichia pastoris", Protein Expression and Purification, vol. 61, Issue 1, 2008, pp. 45-49.
Frias, at at., "Efficacy and safety of LY3298176, a novel dual GIP and GLP-1 receptor agonist, in patients with type 2 diabetes: a randomised, placebo-controlled and active comparator-controlled phase 2 trial", The Lancet, 2018, vol. 392, p. 2180-2193.
Kulkarni, et al., "Rapid and efficient protein synthesis through expansion of the native chemical ligation concept", Nature Reviews Chemistry, vol. 2, Article 0122, 2018, pp. 17.
Malins, et al., "Synthetic Amino Acids for Applications in Peptide Ligation—Desulfurization Chemistry", Aust. J. Chem., 2015, 68, 521-537.
Paik, et al., "Comparability studies of new 3rd generation recombinant human factor VIII GreenGene F after improvement of formulation and viral inactivation/removal process", Biologicals, vol. 40, Issue 6, 2012, pp. 405-414.
Thapa, et al., "Native chemical ligation: a boon to peptide chemistry", Molecules, 2014, 19, 14461-14483.
Wan et al., "Free-Radical-Based, Specific Desulfurization of Cysteine: A Powerful Advance in the Synthesis of 7 Polypeptides and Glycopolypeptides", vol. 6, Issue.48, Angew. Chem. Int. Ed., Dec. 5, 2007, pp. 9248-9252.
EP Patent Application No. 2500006.2, filed on Sep. 3, 2025 by Eli Lilly and Company. Extended European Search Report, search completed on Mar. 12, 2026, mailed on Mar. 23, 2026. 10 pages.
EP Patent Application No. 2500006.0, filed on Sep. 3, 2025 by Eli Lilly and Company. Extended European Search Report, search completed on Mar. 13, 2026, mailed on Mar. 23, 2026. 10 pages.

* cited by examiner

PROCESS FOR PREPARING A GIP/GLP1 DUAL AGONIST

The present application is being filed along with a Sequence Listing in ST.26 XML format. The Sequence Listing is provided as a file titled "X22015B_US.xml" created Aug. 12, 2024, and is 197 KB kilobytes in size. The Sequence Listing information in the ST.26 XML format is incorporated herein by reference in its entirety. No new matter is added herewith.

The present invention provides processes and intermediates for making a GIP/GLP1 dual agonist peptide, tirzepatide, or a pharmaceutically acceptable salt thereof.

Diabetes mellitus is a chronic disorder characterized by hyperglycemia resulting from defects in insulin secretion, insulin action, or both. In type 2 diabetes mellitus ("T2D"), the combined effects of impaired insulin secretion and insulin resistance are associated with elevated blood glucose levels. The GIP/GLP1 dual agonist, tirzepatide is described and claimed in U.S. Pat. No. 9,474,780 ("780 patent"). Tirzepatide can be useful in the treatment of T2D.

U.S. Pat. No. 9,474,780 generally describes peptides and a method for making a GIP/GLP1 dual agonist.

There is a need for processes and intermediates to enable improved technology for production of tirzepatide having a combination of advantages including commercially desired purity. Similarly, there is a need for efficient and environmentally "green" processes, including stable intermediates to provide tirzepatide with fewer purification steps. Improved technology is also needed to provide tirzepatide manufacturing processes producing minimal waste streams for both environmental and operator enhanced safety. The preparation of large-scale, pharmaceutically-elegant tirzepatide presents a number of technical challenges that may affect the overall yield and purity. There is a need for processes to avoid the use of transition metals and/or harsh reaction conditions that are incompatible with peptide synthesis.

The present invention seeks to meet these needs by providing novel intermediates and processes useful in the manufacture of tirzepatide (SEQ ID NO:1), or a pharmaceutically acceptable salt thereof. The improved terzepatide manufacturing processes of the present invention provide intermediates and process reactions embodying a combination of advances, including an efficient route having fewer steps, while at the same time maintaining high quality and purity. Importantly, the improved processes and intermediates decrease resource intensity and minimize waste streams.

The improved processes described herein provide various embodiments of intermediates useful for production of terzepitide.

The present invention provides a compound of SEQ ID NO: 17, or a pharmaceutically acceptable salt thereof. The present invention provides a compound of SEQ ID NO:11, or a pharmaceutically acceptable salt thereof. The present invention provides a compound of SEQ ID NO:22, or a pharmaceutically acceptable salt thereof. The present invention provides a compound of SEQ ID NO:21, or a pharmaceutically acceptable salt thereof. The present invention provides a compound of SEQ ID NO:20, or a pharmaceutically acceptable salt thereof. The present invention provides a compound of SEQ ID NO:2, or a pharmaceutically acceptable salt thereof. The present invention provides a compound of SEQ ID NO:4, or a pharmaceutically acceptable salt thereof. The present invention provides a compound of SEQ ID NO:7, or a pharmaceutically acceptable salt thereof. The present invention provides a compound of SEQ ID NO: 14, or a pharmaceutically acceptable salt thereof. The present invention provides a compound of SEQ ID NO:33, or a pharmaceutically acceptable salt thereof. The present invention provides a compound of SEQ ID NO:32, or a pharmaceutically acceptable salt thereof. The present invention provides a compound of SEQ ID NO:34, or a pharmaceutically acceptable salt thereof. The present invention provides a compound of SEQ ID NO:35, or a pharmaceutically acceptable salt thereof. The present invention provides a compound of SEQ ID NO:36, or a pharmaceutically acceptable salt thereof. The present invention provides a compound of SEQ ID NO:38, or a pharmaceutically acceptable salt thereof. The present invention provides a compound of SEQ ID NO:39, or a pharmaceutically acceptable salt thereof.

Provided is a compound of the formula:

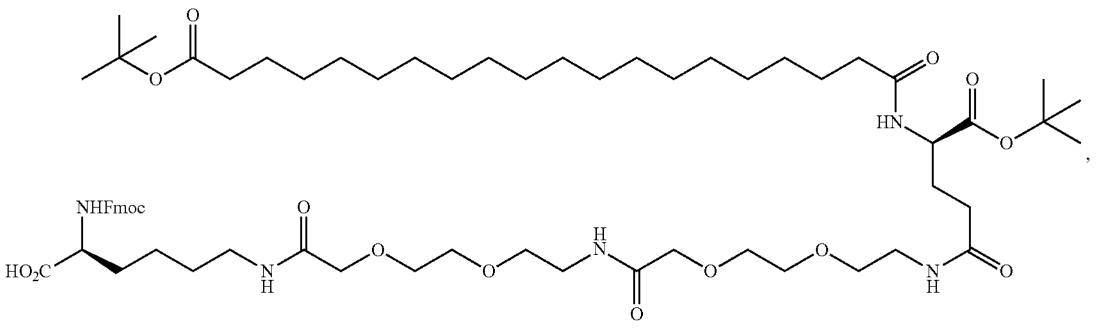

or a pharmaceutically acceptable salt thereof.

Provided is a compound of the formula:

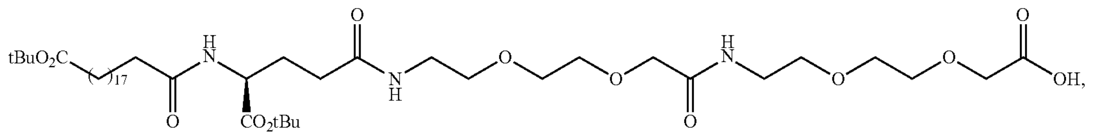

or a pharmaceutically acceptable salt thereof.

The present invention provides a process wherein tirzepatide is prepared using nanofiltration.

The present invention provides a process to prepare tirzepatide, comprising deprotecting a compound, or pharmaceutically acceptable salt, of a compound of SEQ ID NO: 22.

Provided is a process to selectively acylate a lysine amino acid wherein the lysine amino acid and N terminus are protected. Provided is a process to selectively acylate a lysine amino acid in a peptide comprising coupling a resin bound peptide-Lysine-$NH_2$ with t-butyl-eicosanedioyl-Glu-(O-tert-butyl)-(8-amino-3,6-dioxaoctanoic acid)-(8-amino-3,6-dioxaoctanoic acid)-OH. Provided is a process to prepare tirzepatide, comprising deprotecting a compound of SEQ ID NO:22, or a pharmaceutically acceptable salt thereof.

Provided is a process to deprotect tirzepatide wherein the deprotection solution comprises dithiothreitol, triisopropylsilane, and trifluoroacetic acid.

Provided is a process to selectively acylate a lysine amino acid wherein the resin bound peptide-Lysine-$NH_2$ is a compound of the formula:

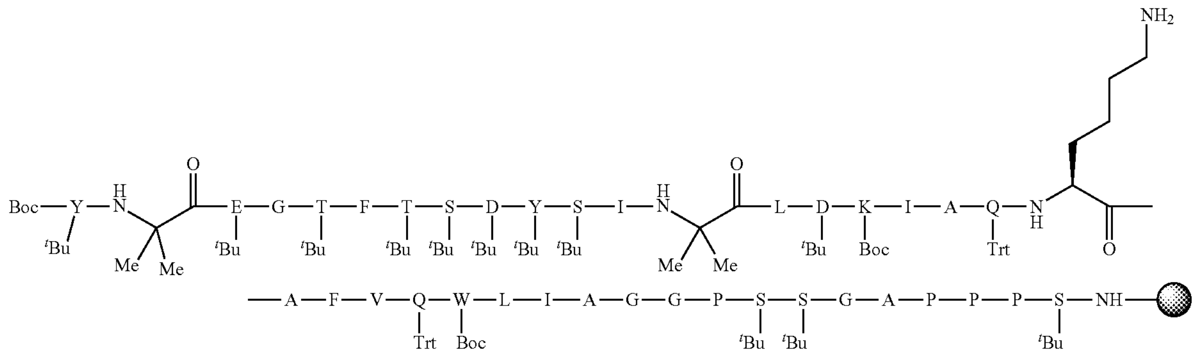

or a pharmaceutically acceptable salt thereof.

Provided is a process to convert depsi peptide isomer to the desired peptide comprising: adjusting the depsi peptide isomer to a pH between about pH 7 to about pH 10; and incubating the depsi peptide isomer at pH 7 to pH 10 for at least one hour.

Provided is a process to convert depsi peptide isomer wherein the depsi peptide isomer is adjusted to about pH 8.5 to about pH 9.5.

Provided is a process to convert depsi peptide isomer wherein the depsi peptide isomer is a compound of SEQ ID NO:40, or a pharmaceutically acceptable salt thereof.

Provided is a radical based desulfurization comprising contacting a peptide with a radical initiator. In an embodiment desulfurization comprises contacting a peptide suitable for desulfurization with a water soluble radical initiator. In an embodiment, the radical initiator is an azo initiator. In an embodiment, the radical initiator is selected from the group consisting of 2,2'-azobis[2-(2-imidazolin-2-yl) propane] Dihydrochloride (VA-044) and 2,2'-Azobis(2-methylpropionamidine) dihydrochloride (VA-050).

The radical based desulfurization method provided herein is environmentally desirable, transition metal free and conditions compatible with peptide synthesis.

As used herein, the following abbreviations have the meanings as set forth herein: "SPPS" means Solid Phase Peptide Synthesis, "Fmoc" means fluorenylmethyloxycarbonyl chloride, "Pip" means piperidine, "DIC" means diisopropylcarbodiimide, "Oxyma" means Ethyl cyanohydroxyiminoacetate, "DCM" means dichloromethane, "IPA" means isopropanol, "MTBE" means methyl-tert-butyl ether, "TFA" means trifluoroacetic acid, "TIPS" means triisopropylsilane, "DTT" means dithiothreitol, "UPLC" means Ultra High Performance Liquid Chromatography, "HFIP" means hexafluoroisopropanol, "CTC" means chlorotrityl, "HATU" means (1-[bis(dimethylamino)methylene]-1H-1,2,3-triazolo [4,5-b]pyridinium 3-oxide hexafluorophosphate, "TFET" means 2,2,2-trifluoroethanethiol, "DIEA" means N,N-diisopropylethylamine, "AEEA" means 17-amino-10-oxo-3,6, 12,15 tetraoxa-9-aza heptadecanoic acid, "TCEP" means tris(2-carboxyethyl) phosphine, "DCU" means dicyclyhexylurea, "DCC" means dicyclhexylcarbodiimide, "TMSA" means trimethylsilyalmide, "HOBt" means hydroxybenzotriazole, "HRMS" means high resolution mass spectrometry, "LPPS" means liquid phase peptide synthesis, "MSMPR" means mixed product mixed suspension reactor, "MPA" means mobile phase A, "MPB" means mobile phase B, "L-GSH" means L-glutathione reduced solution, "TZP" means tirzepatide, "AP" means active pharmaceutical, and "API" means active pharmaceutical ingredient, "PyBOP" means (benzotriazol-1-yloxy)tripyrrolidinophosphonium hexafluorophosphate), "DEA" means diethylamine, "TBTU" means 2-(1H-benzotriazole-1-yl)-1,1,3,3-tetramethylaminium tetrafluoroborate, "TNTU" means 2-(5-Norbornene-2,3-dicarboximido)-1,1,3,3-tetramethyluronium Tetrafluoroborates, "PyOxim" means 1-Cyano-2-ethoxy-2-oxoethylideneaminooxy-tris-pyrrolidino-phosphonium hexafluorophosphate, "PyClock" means 6-chloro-benzotriazole-1-yloxy-tris-pyrrolidino-phosphonium hexafluorophosphate. As presented herein, amino acid one letter abbreviations are presented in bold print, while atoms are presented as unbolded text, and generally in smaller font, to distinguish from one letter amino acid abbreviations. As used herein, when an amino acid abbreviation appears with a number above the amino acid, the number refers to the corresponding amino acid position in the final tirzepatide product. The numbers are provided for convenience and the appearance or absence of such numbers in a sequence does not influence the amino acid sequence or the peptide indicated in such sequence. As used herein, the term "protected" means that a protecting group is attached to at the indicated position. The artisan will recognize that a variety of protecting groups are well known, and alternative protecting groups may be suitable for a particular process.

The artisan will appreciate that there are alternative resins for building the peptides presented herein. For example, Sieber and Rink amide resins are well known to the artisan for preparing peptides disclosed herein; however, alternative resins may be selected for the preparation of peptides described herein. For example, but not limited to, 2-CTC and related resins may be used to prepare a target peptide, followed by a C terminus amidation step.

The Solid Phase Peptide Synthesis (SPPS) builds are accomplished using standard fluorenylmethyloxycarbonyl chloride (Fmoc) peptide chemistry techniques employing sequential couplings with an automated peptide synthesizer. The resin is swelled with DMF then de-protected using 20% piperidine (Pip)/DMF (3×30 min). Subsequent Fmoc deprotections use 20% Pip/DMF 3×30 min treatments and 4×30 min treatments are used for more difficult couplings. After deprotection, the resin is washed with 5×2 min, 10 volume DMF washes. Amino acid pre-activation uses diisopropylcarbodiimide (DIC)/ethyl cyanohydroxyiminoacetate (Oxyma) DMF solutions at room temp for 30 min. Coupling of the activated amino acid to the resin bound peptide occurs for a specified time for each individual amino acid. Solvent washing with 5×2 min 10 volumes DMF is performed after each coupling. For isolation of the final product, the resin bound product is washed 5×2 min with 10 volume DCM to remove DMF. The resin is washed with 2×2 min 10 volume IPA to remove DCM, washed 5×2 min 10 volume methyl-tert-butyl ether (MTBE), then the product is dried at 40° C. under vacuum. The resin bound product is stored cold (−20° C.). For analysis, peptide is cleaved from the resin with an acidic cocktail consisting of trifluoroacetic acid (TFA)/$H_2O$/TIPS (triisopropylsilane)/DTT (dithiothreitol) in the following ratio: (0.93v/0.04v/0.03v/0.03w). The resin is swelled with DCM (4-5 mL, 3×30 min) and drained. The cleavage cocktail (4-5 mL) is added to the pre-swelled resin and the suspension is stirred for 2 hr at room temp. The solution is filtered then the resin is washed with a small amount of DCM and combined with the cleavage solution. The resulting solution is poured into 7-10 volumes of cold (0° C.) methyl-tert-butyl ether (MTBE). The suspension is aged for 30 min at 0° C. then the resulting precipitate is centrifuged and the clear solution is decanted. The residue is suspended in the same volume of MTBE, and the resulting suspension is again centrifuged and decanted. After decanting the clear MTBE solution of the precipitated peptide is dried in vacuo at 40° C. overnight.

Synthesis of Preparation 1

SEQ ID NO:2

The synthesis uses Fmoc-Sieber amide resin with a loading of 0.71 mmol/g. The general SPPS procedure is used with the following modifications:

| Cycle | Amino acid | SPPS conditions Solvent for couplings: DMF |
|---|---|---|
| 1 | Fmoc-L-Ser(t-Bu)-OH | 3 × 30 min De-Fmoc cycles, 6 × 2 min post-dep washes, 3.0 AA/3.3 DIC/3.0 Oxyma 4 h, rt. |
| 2 | Fmoc-L-Pro-OH | 3 × 30 min De-Fmoc cycles, 6 × 2 min post-dep washes, 3.0 AA/3.3 DIC/3.0 Oxyma 6 h, rt. |
| 3 | Fmoc-L-Pro-OH | 4 × 30 min De-Fmoc cycles, 6 × 2 min post-dep washes, 3.0 AA/3.3 DIC/3.0 Oxyma 6 h, rt. |
| 4 | Fmoc-L-Pro-OH | 4 × 30 min De-Fmoc cycles, 6 × 2 min post-dep washes, 3.0 AA/3.3 DIC/3.0 Oxyma 6 h, rt. |
| 5 | Fmoc-L-Ala-OH | 4 × 30 min De-Fmoc cycles, 6 × 2 min post-dep washes, 3.0 AA/3.3 DIC/3.0 Oxyma 4 h, rt. |
| 6 | Fmoc-Gly-OH | 3 × 30 min De-Fmoc cycles, 6 × 2 min post-dep washes, 3.0 AA/3.3 DIC/3.0 Oxyma 4 h, rt. |
| 7 | Fmoc-L-Ser(t-Bu)-OH | 3 × 30 min De-Fmoc cycles, 6 × 2 min post-dep washes, 3.0 AA/3.3 DIC/3.0 Oxyma 4 h, rt. |
| 8 | Fmoc-L-Ser(t-Bu)-OH | 3 × 30 min De-Fmoc cycles, 6 × 2 min post-dep washes, 3.0 AA/3.3 DIC/3.0 Oxyma 4 h, rt |
| 9 | Fmoc-L-Pro-OH | 3 × 30 min De-Fmoc cycles, 6 × 2 min post-dep washes, 3.0 AA/3.3 DIC/3.0 Oxyma 4 h, rt |
| 10 | Fmoc-Gly-OH | 4 × 30 min De-Fmoc cycles, 6 × 2 min post-dep washes, 3.0 AA/3.3 DIC/3.0 Oxyma 4 h, rt. |

Preparation 1 Soft cleavage: Ten identical deprotection reactions are run in parallel, each on ~0.5 mmol scale of resin bound Preparation 1 using the following protocol: 1) To a 40 mL fritted reactor, add 1.55 g (~0.5 mmol) of resin bound Preparation 1. 2) Swell with 3×15 mL of DMF (15 min each), 3) Treat with 3×15 mL (30 min each) of 20% Pip/DMF. 4) Wash with 4×15 mL of DMF followed by 4×15 mL of DCM. 5) Add 1.5 ml of TFA and 28.5 mL of DCM to each of five 40 mL reaction vials. 6) Add one-fifth of the Preparation 1 resin bound (2.75 g) to each of the TFA solution vials and cap the vials and mix on the rotary wheel for 5 minutes. 7) Filter the mixtures and wash with 100 mL of DCM, to give a total filtrate volume of 500 mL. 8) Combine the filtrates and transfer to a round bottom flask containing 1000 mL of MTBE. 9) Concentrate the resulting suspension to a light yellow oil, triturate with 200 mL of MTBE, and cool in an ice bath for 30 minutes. 10) Filter the solid, wash with 50 mL of cold MTBE, and dry in a vacuum oven at 33° C. overnight to produce 5.35 g (91% yield) of a white solid. Analysis of the isolated solid using UPLC (98.57 area %, with 0.99% of combined t-Bu de-protection byproducts).

Synthesis of Preparation 2

SEQ ID NO:3

The synthesis uses Fmoc-Gly-OH 2-CTC resin with a loading of 0.61 mmol/g. The general SPPS procedure is used with the following modifications:

| Cycle | Amino acid | SPPS conditions Solvent for couplings: DMF |
|---|---|---|
| 1 | Fmoc-L-Ala-OH | 3 × 30 min De-Fmoc cycles, 6 × 2 min post-dep washes, 3.0 AA/3.3 DIC/3.0 Oxyma 4 h, rt. |
| 2 | Fmoc-L-Ile-OH | 3 × 30 min De-Fmoc cycles, 6 × 2 min post-dep washes, 3.0 AA/3.3 DIC/3.0 Oxyma 4 h, rt. |
| 3 | Fmoc-L-Leu-OH | 4 × 30 min De-Fmoc cycles, 6 × 2 min post-dep washes, 3.0 AA/3.3 DIC/3.0 Oxyma 6 h, rt. |
| 4 | Fmoc-L-Trp(Boc)-OH | 3 × 30 min De-Fmoc cycles, 6 × 2 min post-dep washes, 3.0 AA/3.3 DIC/3.0 Oxyma 6 h, rt. |
| 5 | Fmoc-L-Gln(Trt)-OH | 3 × 30 min De-Fmoc cycles, 6 × 2 min post-dep washes, 3.0 AA/3.3 DIC/3.0 Oxyma 4 h, rt. |
| 6 | Fmoc-L-Val-OH | 4 × 30 min De-Fmoc cycles, 6 × 2 min post-dep washes, 3.0 AA/3.3 DIC/3.0 Oxyma 6 h, rt. |
| 7 | Fmoc-L-Phe-OH | 4 × 30 min De-Fmoc cycles, 6 × 2 min post-dep washes, 3.0 AA/3.3 DIC/3.0 Oxyma 8 h, rt. |
| 8 | Fmoc-L-Ala-OH | 3 × 30 min De-Fmoc cycles, 6 × 2 min post-dep washes, 3.0 AA/3.3 DIC/3.0 Oxyma 4 h, rt. |
| 9 | Fmoc-Lys(Alloc)-OH | 4 × 30 min De-Fmoc cycles, 6 × 2 min post-dep washes, 3.0 AA/3.3 DIC/3.0 Oxyma 8 h, rt. |
| 10 | Fmoc-L-Gln(Trt)-OH | 3 × 30 min De-Fmoc cycles, 6 × 2 min post-dep washes, 3.0 AA/3.3 DIC/3.0 Oxyma 4 h, rt. |
| 11 | Fmoc-L-Ala-OH | 3 × 30 min De-Fmoc cycles, 6 × 2 min post-dep washes, 3.0 AA/3.3 DIC/3.0 Oxyma 4 h, rt. |
| 12 | Fmoc-L-Ile-OH | 3 × 30 min De-Fmoc cycles, 6 × 2 min post-dep washes, 3.0 AA/3.3 DIC/3.0 Oxyma 4 h, rt. |
| 13 | Fmoc-L-Lys(Boc)-OH | 3 × 30 min De-Fmoc cycles, 6 × 2 min post-dep washes, 3.0 AA/3.3 DIC/3.0 Oxyma 4 h, rt. |
| 14 | Fmoc-L-Asp(tBu)-OH | 3 × 30 min De-Fmoc cycles, 6 × 2 min post-dep washes, 3.0 AA/3.3 DIC/3.0 Oxyma 4 h, rt. |

Preparation 2 soft cleavage: To a 40 mL glass scintillation vial, add resin bound Preparation 2 (3.06 g, 1.12 mmol) and 30 mL of 30% HFIP DCM solution where a red color change is observed. Agitate the vial by spinning on a wheel at ambient temp for 1 hr. Filter the resin off and wash with 3×10 mL DCM. Remove the solvent in vacuo to form a glassy foam (35° C. bath, 10 torr, 2.34 g) and replace with a small portion of IPA (24 mL), and then add water (24 mL) dropwise over 25 min. at room temp. Stir the resulting solution for 30 min. and then filter. Wash the cake washed 3×10 mL $H_2O$ and then dry in the vacuum oven at 25 torr and 35° C. overnight. This produces Preparation 2 as a white solid (1.81 g).

Synthesis of Preparation 4

SEQ ID NO:4

The synthesis uses Fmoc-Leu-OH 2-CTC resin with a loading of 0.68 mmol/g. The general SPPS procedure is used with the following modifications:

| Cycle | Amino acid | SPPS conditions Solvent for couplings: DMF |
|---|---|---|
| 1 | Fmoc-Aib-OH | 4 × 30 min De-Fmoc cycles, 6 × 2 min post-dep washes, 3.0 AA/3.3 DIC/3.0 Oxyma 8 h, rt. |
| 2 | Fmoc-L-Ile-OH | 4 × 30 min De-Fmoc cycles, 6 × 2 min post-dep washes, 3.0 AA/3.3 DIC/3.0 Oxyma 18 h, rt. |
| 3 | Fmoc-L-Ser(tBu)-OH | 3 × 30 min De-Fmoc cycles, 6 × 2 min post-dep washes, 3.0 AA/3.3 DIC/3.0 Oxyma 4 h, rt. |
| 4 | Fmoc-L-Tyr(tBu)-OH | 3 × 30 min De-Fmoc cycles, 6 × 2 min post-dep washes, 3.0 AA/3.3 DIC/3.0 Oxyma 4 h, rt |
| 5 | Fmoc-L-Asp(tBu)-OH | 3 × 30 min De-Fmoc cycles, 6 × 2 min post-dep washes, 3.0 AA/3.3 DIC/3.0 Oxyma 4 h, rt. |
| 6 | Fmoc-L-Ser(tBu)-OH | 3 × 30 min De-Fmoc cycles, 6 × 2 min post-dep washes, 3.0 AA/3.3 DIC/3.0 Oxyma 4 h, rt. |
| 7 | Fmoc-L-Thr(tBu)-OH | 3 × 30 min De-Fmoc cycles, 6 × 2 min post-dep washes, 3.0 AA/3.3 DIC/3.0 Oxyma 4 h, rt. |
| 8 | Fmoc-L-Phe-OH | 3 × 30 min De-Fmoc cycles, 6 × 2 min post-dep washes, 3.0 AA/3.3 DIC/3.0 Oxyma 4 h, rt |
| 9 | Fmoc-L-Thr(tBu)-OH | 3 × 30 min De-Fmoc cycles, 6 × 2 min post-dep washes, 3.0 AA/3.3 DIC/3.0 Oxyma 4 h, rt |
| 10 | Fmoc-Gly-OH | 4 × 30 min De-Fmoc cycles, 6 × 2 min post-dep washes, 3.0 AA/3.3 DIC/3.0 Oxyma 6 h, rt. |
| 11 | Fmoc-L-Glu(tBu)-OH | 4 × 30 min De-Fmoc cycles, 6 × 2 min post-dep washes, 3.0 AA/3.3 DIC/3.0 Oxyma 6 h, rt. |
| 12 | Fmoc-Aib-OH | 4 × 30 min De-Fmoc cycles, 6 × 2 min post-dep washes, 3.0 AA/3.3 DIC/3.0 Oxyma 8 h, rt. |
| 13 | Boc-L-Tyr(tBu)-OH | 4 × 30 min De-Fmoc cycles, 6 × 2 min post-dep washes, 3.0 AA/3.3 DIC/3.0 Oxyma 18 h, rt. |

Preparation 4 Soft cleavage: To a 20 mL glass scintillation vial, add resin bound Preparation 4 (2.0 g, 0.62 mmol) and 10 mL of 30% HFIP DCM solution where a red color change is observed. Agitate the vial by spinning on a wheel at ambient temperature, then filter off the resin, wash with 3×2 mL DCM, and remove the solvent in vacuo to form a glassy, sticky foam. Dissolve the foam in 5.2 mL DMSO. Add this solution with 6 mL of water at equal flow rates (T ~15° C.) over 45 min with 1 mL of water. Once the peptide solution is fully added, add an additional 6 mL of water over 45 min. White solids precipitate upon addition. Stir the resulting slurry at 15° C. for 30 min. Filter the solids, wash with 6 mL of water, and then transfer to the vacuum oven at 35° C. and 25 torr. This yields Preparation 4 (Boc-1-14-OH, 1.0763 g) as a white fluffy solid.

Synthesis of Preparation 3 by LPPS

SEQ ID NO:5

To a 20 mL glass scintillation vial, add Preparation 2 (500 mg, 0.183 mmol), Preparation 1 (179 mg, 0.175 mmol), and DMSO (10 mL). Add DIEA (46 μL, 0.265 mmol) to this solution followed by PyBOP (benzotriazol-1-yloxy)tripyrrolidinophosphonium hexafluorophosphate) (123 mg, 0.230 mmol). Stir the reaction for 2 hours then, add diethylamine (DEA) (183 microliters, 1.77 mmol) and stir the resulting solution for 2 hours. Draw the contents of the reaction into a syringe and add to a stirred 50 mL flask with simultaneous dropwise addition of water (12 mL) over 1 hour. After the additions are complete, collect the precipitated product by filtration and subsequently wash with water (2×4 mL). Dry the wetcake under vacuum at 35° C. for 18 hours to obtain Preparation 3 as a white solid (0.6003 g, 88% yield, HRMS calcd for $C_{184}H_{261}N_{31}O_{38}$ expected 3512.9444, actual 3512.9430).

Synthesis of Preparation 5 by LPPS

SEQ ID NO: 6

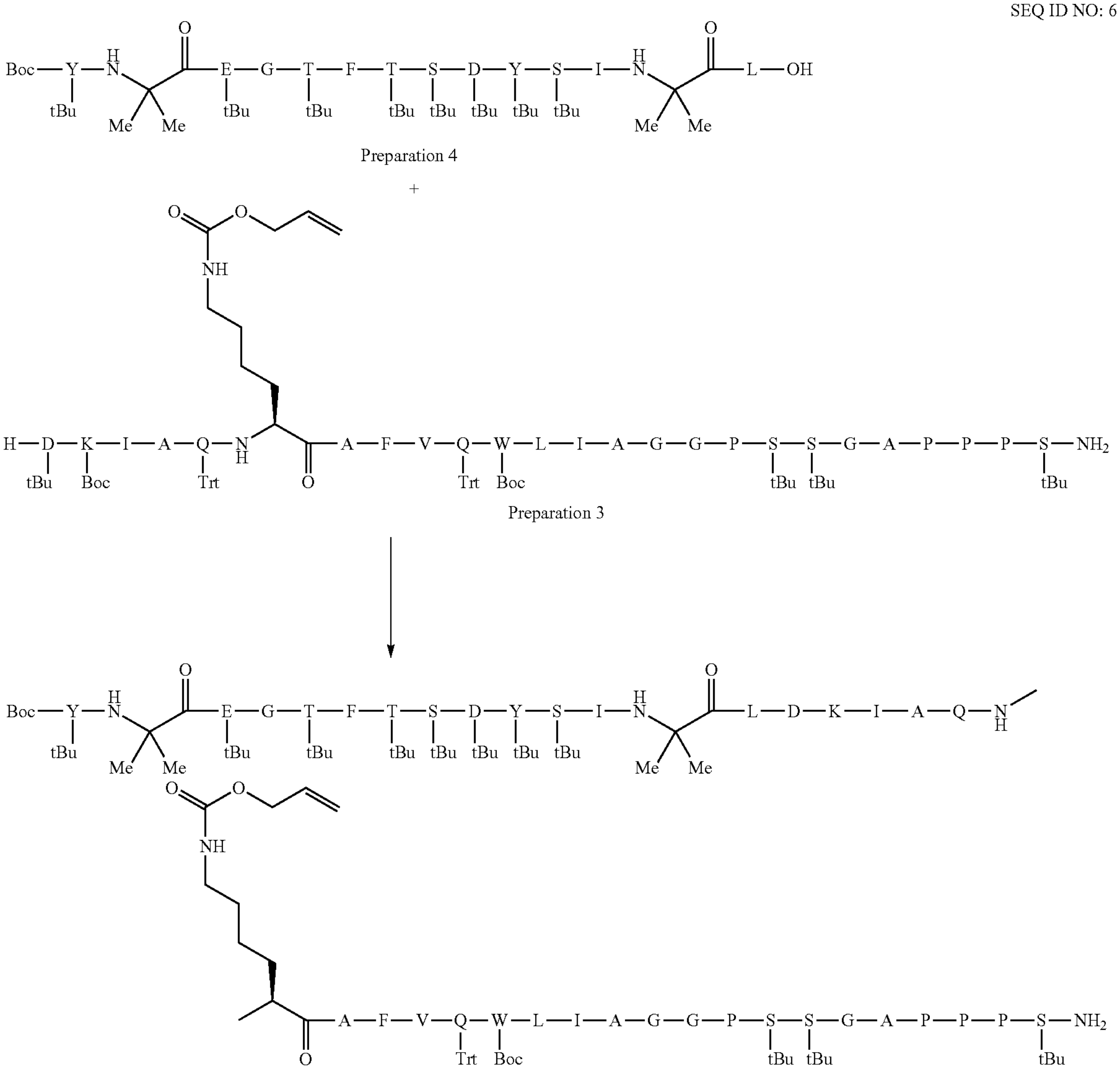

Preparation 4

+

Preparation 3

Preparation 5

To a 20 mL glass scintillation vial, add Preparation 3 (338.8 mg, 0.091 mmol), Preparation 4 (192.1 mg, 0.091 mmol) and DMSO (10 mL). To this solution, add PyBOP (63.5 mg, 0.118 mmol) followed by DIEA (79 microliters, 0.454 mmol). Stir the reaction solution for 2.5 hours. Draw the contents of the reaction into a syringe and add the contents to a stirred 50 mL flask with simultaneous dropwise addition of water (12 mL) over 1 hour. After the additions are complete, collect the precipitated product by filtration and subsequently wash with water (2×4 mL). Dry the wetcake under vacuum at 35° C. for 18 hours to obtain Preparation 5 as a white solid (0.3568 g, 70% yield, HRMS calcd for $C_{293}H_{435}N_{45}O_{64}$ expected 5608.2168, actual 5608.2066).
Preparation 6 Synthesis by Method 1 (LPPS)
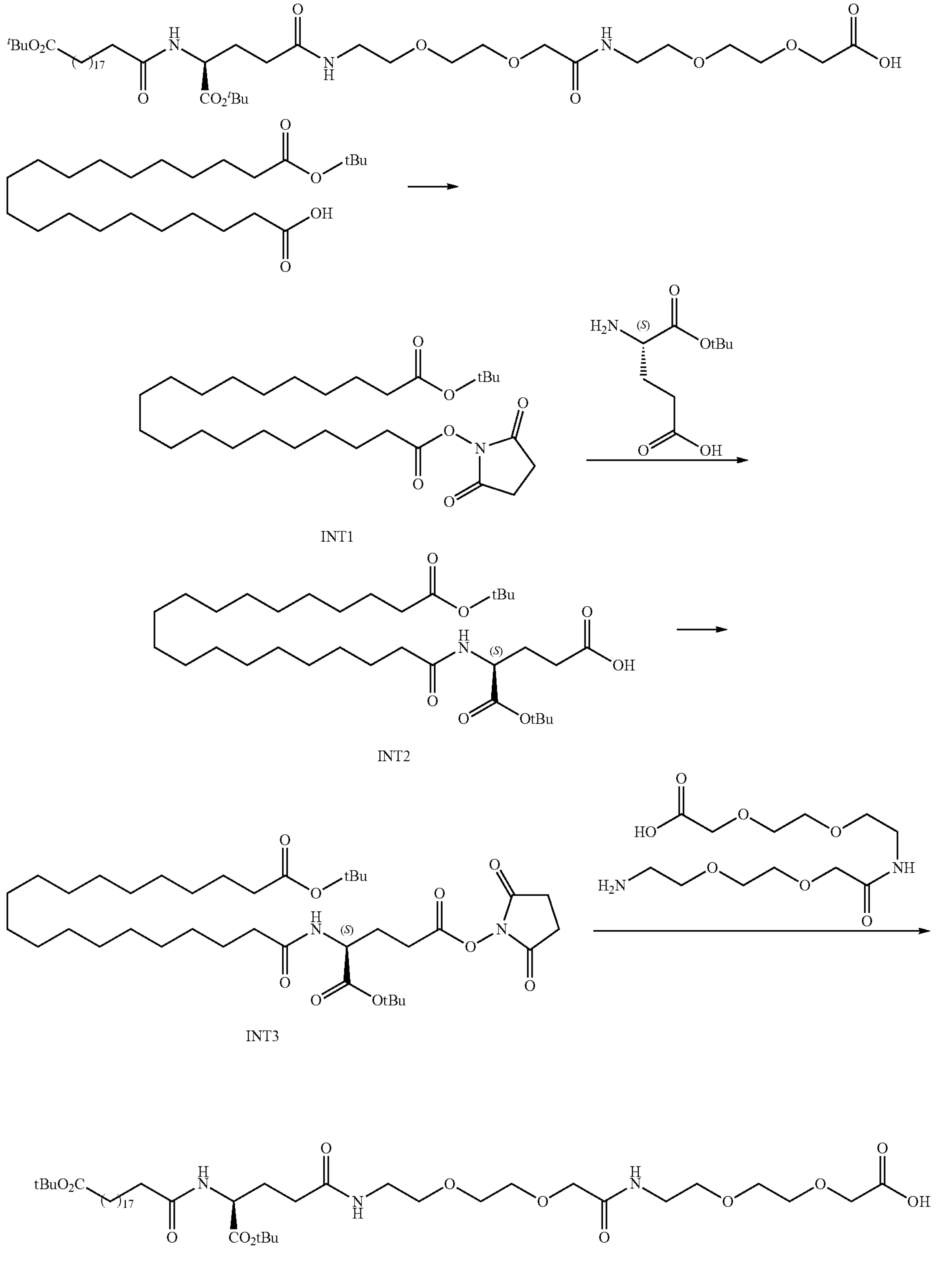
INT1
INT2
INT3
Preparation 6

Dissolve eicosanedioic acid, mono(1,1-dimethylethyl) ester (15.0 kg, limiting reagent) and N-hydroxy-succinimide (1.2 eq) in ethyl acetate at 27° C. Add a solution of DCC (1.25 eq.) in ethyl acetate and stir the reaction for 24 hr at 22° C. Filter off the resulting DCU by-product and then extract the organic phase three times with 5% NaCl aq. solution. After extraction, concentrate the organic phase, co-evaporate with isopropanol, and then crystallize by addition of heptane. After filtration rinse the filter cake with heptane and dry at 25° C. to afford 17.0 kg of INT1 in 87% yield and 99% purity.

Dissolve H-Glu-OtBu (7.7 kg, 1.1 eq) in DCM (54 L) at 20° C., then add a solution of TMSA (11.3 kg) dissolved in DCM (7 L), then stir the reaction mixture for 1 hr at 40° C. Add INT1 (17.0 kg) DCM solution at room temperature and stir 8 hr. After the reaction is complete, DCM is exchanged to ethyl acetate by distillation. Wash the organic phase three times with 2% aq. $KHSO_4$/NaCl aqueous solution then wash 4 times with 2% NaCl aqueous solution. After separation and removal of aqueous phases, concentrate the organic phase with isopropanol, dilute with isopropanol, and then crystallize by addition of water. After filtration, wash the filter cake with a mixture of water/isopropanol, and then dry at 30° C. to produce 17.3 kg of INT 2 in 86% yield and 99% purity.

Dissolve the INT 2 (17.3 kg) and N-hydroxy-succinimide (4.1 kg, 1.2 eq) in ethylacetate (336 kg) at 27° C. Add a solution of DCC (8.33 kg, 1.25 eq) in ethyl acetate and stir the reaction for 24 hr at 22° C. Filter off the resulting DCU by-product. Concentrate the organic phase, co-evaporate with isopropanol, and then crystallize by cooling the isopropanol solution (~125 L). After, rinse the filter cake with cold isopropanol and dry at 25° C. to afford 16.3 kg INT 3 with 81% yield and 96% purity.

Suspend 17-amino-10-oxo-3,6,12,15 tetraoxa-9-aza heptadecanoic acid (AEEA2) (8.1 kg, 26.3 mol) in DCM (54 L) at 22° C., add a TMSA (7.68 kg, 59.9 mol) solution in DCM (6.2 L), and then stir the reaction mixture for an hour at 40° C. Suspend INT 3 (16 kg) in DCM (31 L) at 35° C. and add to the TMS-protected (AEEA2) mixture at 22° C. Stir the reaction for 12 hr, and after reaction completion the mixture is concentrated, then exchanged to ethyl acetate. Wash the organic phase three times with a 2% aq. $KHSO_4$/NaCl aqueous solution (~200 L), and then wash 4 times with a 2% NaCl aqueous solution (~200 L) to a target pH of 4.5. Concentrate the organic phase and exchange to acetonitrile. Cool the acetonitrile solution to −20° C. and then age the resulting suspension for 15 hr at −20° C. Filter the mixture, rinse the filter cake with cold acetonitrile the dry at <0° C. to afford 18.4 kg of Preparation 6 (88% yield) with 96% purity. Overall yield=53%.

Preparation 6 Synthesis by Method 2 (SPPS)

Alternatively, Preparation 6 may be prepared using solid phase peptide synthesis using a peptide synthesizer.

Standard coupling procedures are utilized.

Standard Coupling Conditions:

0.133 M, 2.0 equiv HATU, 5.0 equiv DIEA, ambient temperature, 3 hours, deprotection for 3×15 min with 20% piperidine/DMF.

Resin Charging:

FmocNH-AEEA on 2-CTC resin (0.99 mmol/g): 1.01 g in each of the parallel reactions. An automatic program using a DMF swell, followed by Pip/DMF; DMF wash; and amino acid, DIEA, HATU mix; and DMF wash cycles followed by drying.

The resin is cleaved by stirring the combined lots in 30% HFIP/DCM (240 mL) for 1.5 hours. The resin is filtered, washed, and the solvent is removed from the filtrate in vacuo. The resulting oil is dissolved in acetonitrile and solvent is removed again. This operation provides 30.47 g (146% of theoretical yield) of a viscous yellow oil, containing 52.3 area % desired product by UPLC analysis. The crude product is purified by flash chromatography (500 grams of silica gel, eluted with 85% DCM/10% methanol/5% acetic acid, 38×100 mL fractions collected). Previously chromatographed concentrate (17.94 g) is crystallized to yield 13.4 g (74.7% yield), with a UPLC purity of 91.65 area %.

EXAMPLE 1

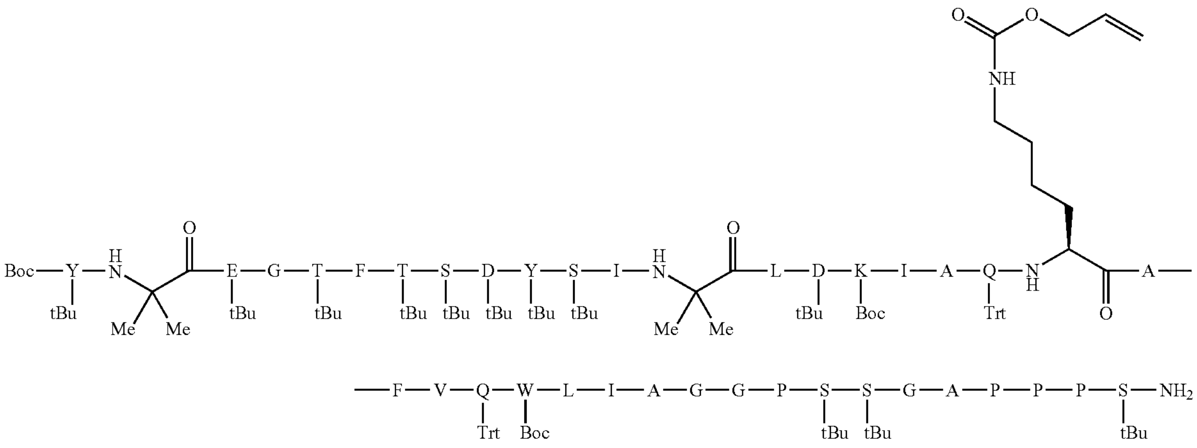

Preparation 5

-continued
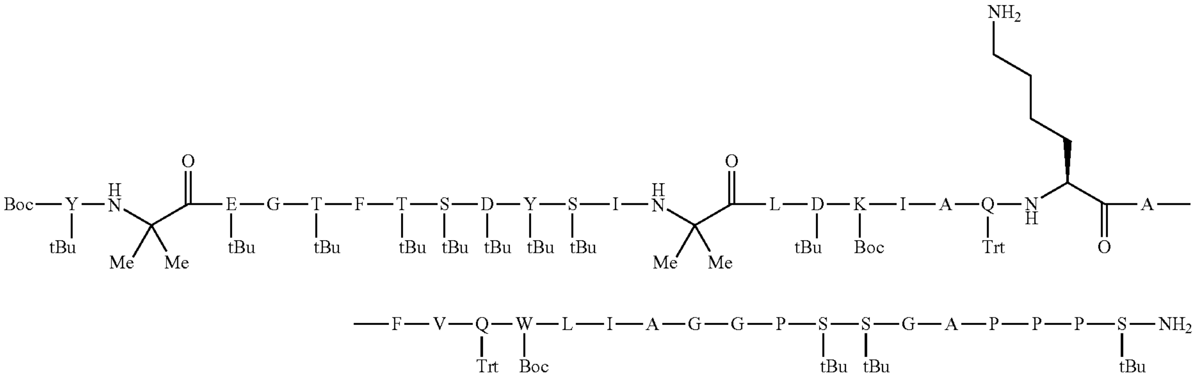
Preparation 7
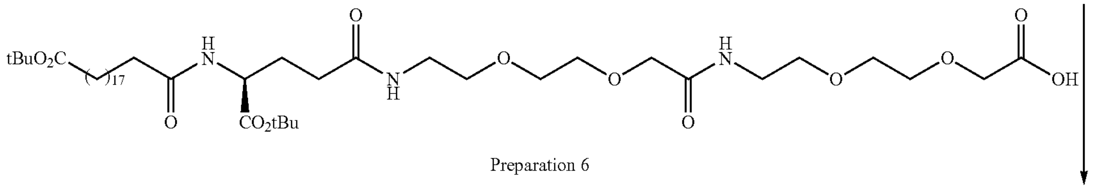
Preparation 6
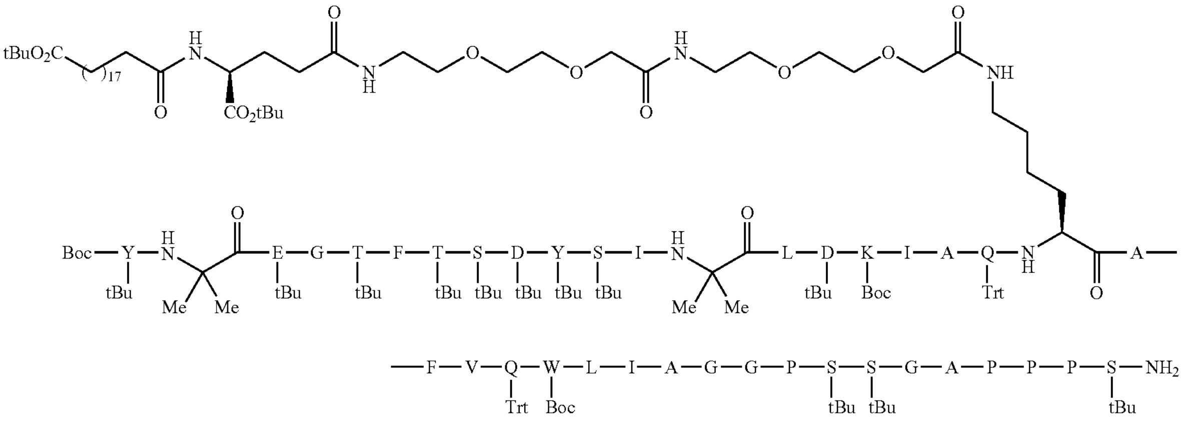
Preparation 8

-continued

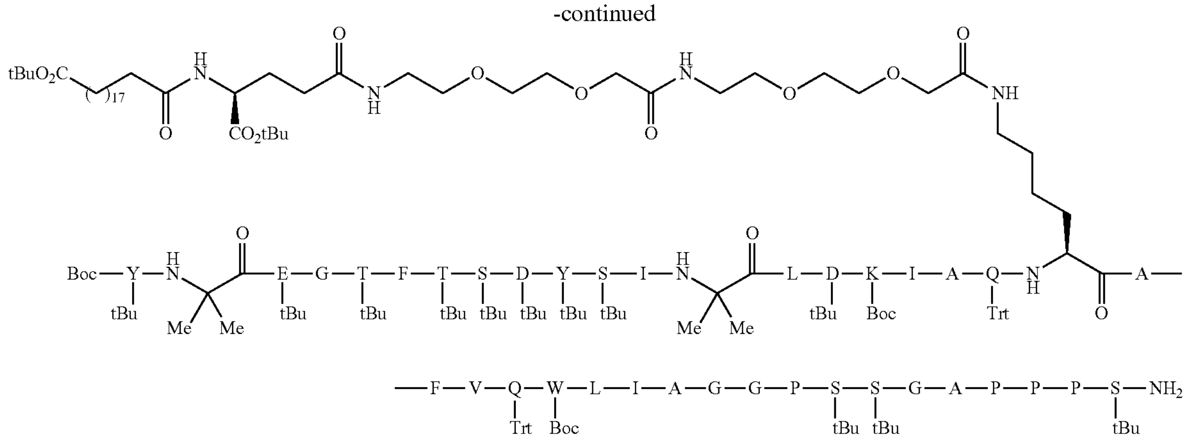

Preparation 8

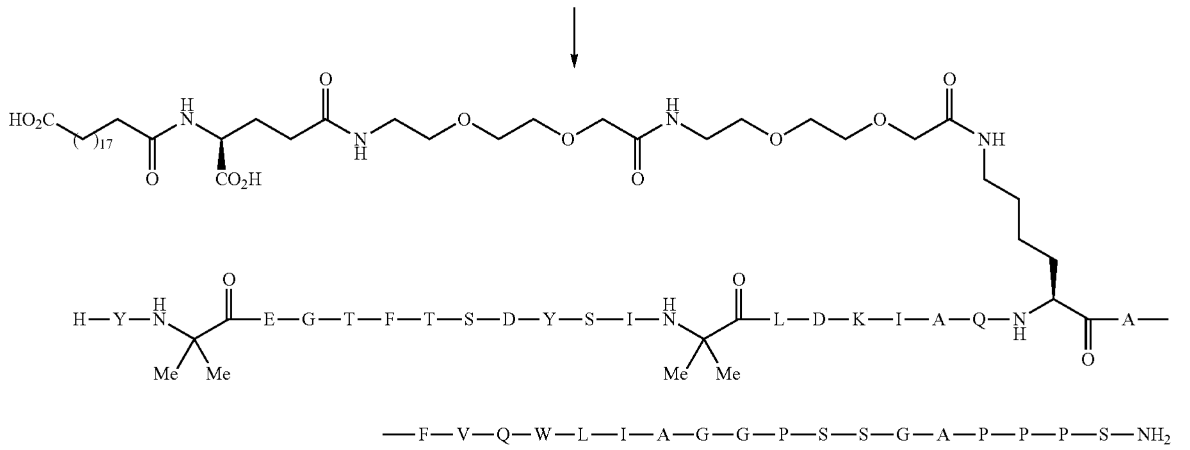

Example 1

SYNTHESIS EXAMPLE 1

SEQ ID NO:1

To a first HPLC vial, add Preparation 5 (10.5 mg, 0.00187 mmol) and DCM (200 μL, 20 L/kg). To this solution, add a solution of phenylsilane (0.81 M in DCM, 22.1 μL, 0.0178 mmol) and tetrakis(triphenylphosphine)-palladium (0) (0.8 M in DCM, 22.1 μL, 0.00064 mmol). Stir the solution at 24° C. for one hour to obtain a non-isolated solution of Preparation 7 (SEQ ID NO:7). To a second HPLC vial, add DCM (150 μL) followed by Preparation 6 (0.118 M in DCM, 16 μL, 0.00189 mmol), PyBOP (0.186 M in DCM, 16 μL, 0.00298 mmol) and DIEA (0.573 M in DCM, 5 equiv.). Add the contents of the second vial to the first vial and stir the reaction for 1 hour to obtain a non-isolated solution of Preparation 8 (SEQ ID NO:8). Concentrate the solution of Preparation 8 under vacuum and to the resulting solid, add 50 μL of a solution of trifluoroacetic acid (4.65 mL), triisopropylsilane (20 μL) and DTT (20 mg). Stir the slurry for 18 hours and monitor by HPLC to confirm the formation of Example 1 (HRMS calcd for $C_{225}H_{348}N_{48}O_{68}$ expected 4810.5249, actual 4810.5257).

Synthesis of Preparation 9

SEQ ID NO:9

Suspend Sieber amide resin (13.42 g, 0.75 mmol/g, 10.1 mmol) in DMF (130 mL, 10 vols) for about 20 min and then drain. Wash the resulting resin with DMF (80 mL, 6 vols) for about 5 min. Remove the Fmoc group by treatment of the Fmoc-amino acid resin with 5 vol % piperidine, 1.25 vol % DBU, 1.0 wt. % HOBt/DMF solution (80 mL, 6 vols) twice, 10 min and 20 min, respectively. Wash twice with DMF (80 mL, 6 vols), twice with MTBE (80 mL, 6 vols) and again twice with DMF (80 mL, 6 vols) after draining the de-Fmoc solution.

Using standard Fmoc chemistry, assemble the amino acid chain. Generally, 1.5 equiv of Fmoc-amino acid and HOBt (2.47 g, 20% water wet, 14.6 mmol, 1.46 equiv) are dissolved in DMF (60 mL, 4.5 vols) followed by addition of DIEA (1.94 mL, 11.1 mmol, 1.11 equiv). Cool the resulting solution to <5° C. with an ice bath and activate by addition of TBTU (4.83 g, 15.0 mmol, 1.5 equiv). Allow to stand for about 5 minutes at 0° C.-5° C. Add DCM (60 mL, 1.5 vol) to the resin followed by the addition of the activated Fmoc-amino acid solution. Stir the resulting mixture at about ambient temperature for 2 hours. Repeat the deFmoc procedure and coupling with the rest of the amino acids sequentially. After completing the last deFmoc procedure, wash the resin with 2-propanol (130 mL, 10 vols) for 5 min twice, followed by washing with MTBE (130 mL, 10 vols) six times. The resin is dried at 35° C. in vacuo, resulting in Preparation 9-Seiber (21.21 g, 0.435 mmol/g theory, 91.7% yield based on mass increase).

A portion of the Preparation 9-resin complex (10.15 g, 0.435 mmol/g, 4.41 mmol) is treated with 5 vol % TFA in DCM (101 mL, 10 vols) solution and DCM wash step. The cleavage fractions and washes are neutralized with DIEA (26.29 g, 35.5 mL, 1.01:1 molar ratio to TFA). The fractions are combined and concentrated under vacuum to 50% of the original volume. Wash the DCM solution with saturated aq $NaHCO_3$ (2×94 mL). Dry the resulting solution over anhydrous $MgSO_4$ and concentrate to dryness to yield a gummy solid. Reslurry this gummy solid in <5° C. MTBE (100 mL) to break up the gum, resulting in a white slurry product. Filter, wash and dry the white powder slurry resulting in Preparation 9 (3.84 g, 92.3 area %, 37.8 wt % DIEA•TFA, 57.4 wt %, 2.29 mmol, 51.9% yield, HRMS calcd for $C_{46}H_{78}N_{10}O_{12}$ expected 962.5801, actual 962.5806) as a white powder.

Synthesis of Preparation 10

SEQ ID NO:10

Suspend Fmoc-Gly-Gly-O-2CTC resin complex (18.09 g, 0.57 mmol/g, 10.3 mmol) in DMF (180 mL, 10 vols) for 20 min and then drain. Wash the resulting resin with DMF (108 mL, 6 vols) for 5 min. Remove the Fmoc group by treatment of the Fmoc-amino acid resin with 5 vol % piperidine, 1.25 vol % DBU, 1.0 wt. % HOBt/DMF solution (108 mL, 6 vols) twice, 10 min and 20 min respectively. Drain the de-Fmoc solution and wash the resin twice with DMF (110 mL, 6 vols), twice with MTBE (110 mL, 6 vols) and again twice with DMF (110 mL, 6 vols). The chain assembly is conducted with standard Fmoc chemistry.

For the coupling of the amino acids, generally 1.5 equiv of Fmoc-amino acid and HOBt (2.54 g, 20% water wet, 15.0 mmol, 1.5 equiv) are dissolved in DMF (80 mL, 4.4 vols) followed by addition of DIEA (1.94 g, 15.0 mmol, 1.5 equiv) to provide coupling of the amino acids. Cool the resulting solution to 0-5° C. with an ice bath and activate by addition of 2-(1H-benzotriazole-1-yl)-1,1,3,3-tetramethylaminium tetrafluoroborate (TBTU) (4.84 g, 15.1 mmol, 1.5 equiv). Allowed to stand for 5 min at 0-5° C. DCM (35 g, 1.5 vol) and then add to the resin followed by the addition of the activated Fmoc-amino acid solution. The resulting mixture is stirred at rt for 2 h. The peptide resin is washed after completion of the synthetic steps with 2-propanol (180 mL, 10 vols) for 5 min twice and then MTBE (180 mL, 10 vols each, 6 times) followed by drying at 35° C., resulting in Preparation 10 resin complex (25.52 g, 0.216 mmol/g, 53.6% yield).

Treat a portion of the Preparation 10 resin complex (10.075 g, 0.216 mmol/g, 2.18 mmol) three times with 1 vol % TFA in DCM (100 mL, 10 vols) solution and wash with DCM (75 mL, 7.5 vols). Neutralize the cleavage fractions and washes with pyridine (3.18 g, 1.01:1 molar ratio to TFA). Combine and concentrate the fractions under vacuum to dryness at ≤35° C. Perform the reconstitution with ethanol (40 mL, 10% vol. of the combined filtrates) followed by concentration to dryness. Finally, triturate the peptide with stirring in deionized water (150 mL, 40% vol. of the combined filtrates). Collect the solid crude peptide precipitate by centrifugation and wash with deionized water two times (150 mL each). Wash the solid with n-heptane twice (100 mL each), isolate, and dry in vacuo at 40° C. to yield Preparation 10 (SEQ ID NO:10) as a crunchy light yellow solid (4.10 g, 72.4 area %, 3.0 wt % pyridine•TFA, 70.2 wt %, 1.85 mmol, 85.1% yield, HRMS calcd for $C_{88}H_{103}N_{11}O_{15}$ expected 1553.7635, actual 1553.7656).

Synthesis of Preparation 11

SEQ ID NO:11

Suspend H-Alanine-O-2CTC resin complex (40.39 g, 0.5 mmol/g, 20.20 mmol) in DMF (400 mL, 10 vols) for about 20 minutes and then drain. Wash the resulting resin with DMF (400 mL, 10 vols) for 5 min twice. Assemble the amino acid chain using standard Fmoc chemistry. Generally, dissolve 1.5 equiv of Fmoc-amino acid and HOBt (5.51 g, 80 wt. %, 32.6 mmol, 1.6 equiv) in DMF (150 mL, 3.7 vols) followed by addition of DIEA (4.22 g, 32.7 mmol, 1.6 equiv). Cool the resulting solution to about <5° C. with an ice bath and activated by addition of TBTU (10.39 g, 32.4 mmol, 1.6 equiv). Allow to stir for about 5 minutes at 0-5° C. Add DCM (80 mL, 2 vols) to the resin followed by the addition of the activated Fmoc-amino acid solution. Stir the resulting mixture at about ambient temperature for 2 hours.

Remove the Fmoc group by treatment of the Fmoc-amino acid resin with 5 vol % piperidine, 1.25 vol % DBU, 1.0 wt % HOBt/DMF solution (240 mL, 6 vols) twice, 10 min and 20 min respectively. Drain the de-Fmoc solution, wash the resin twice with DMF (240 mL, 6 vols), twice with MTBE (240 mL, 6 vols) and again twice with DMF (240 mL, 6 vols). The peptide resin is thoroughly washed with 2-propanol (400 mL, 10 vols) twice and MTBE (400 mL, 10 vols each, 6 times) after completion of the synthetic steps followed by drying in vacuo at 35° C. to yield loaded resin less the last amino acid (74.82 g, 0.159 mmol/g, 11.90 mmol, 58.9% yield). Add the last amino acid, Fmoc-Leu-OH separately to a portion of the resin (13.61 g, 0.159 mmol/g, 2.16 mmol). Swell this resin with DMF (130 mL, 10 vols, 3 times) for >5 min each, then deprotect (130 mL deprotection mixture prepared from 5.6 g piperidine, 1.67 g DBU, 1.3 g HOBt in 120 mL DMF, 10 vols twice) at 10 min and 20 min. Wash the resin with DMF (80 mL, 6 vols, twice), followed by MTBE (80 mL, 6 vols, twice), and then DMF (80 mL, 6 vols, twice) for 5 min each. Dissolve in DMF (50 mL, 3.7 vols) followed by addition of DIEA (0.54 g, 4.2 mmol, 1.9 equiv for the coupling of the Fmoc-Leu-OH, Fmoc-Leu-OH (1.47 g, 4.16 mmol, 1.9 equiv) and HOBt (0.704 g, 80 wt. %, 4.17 mmol, 1.9 equiv)). Cool the resulting solution to <5° C. with an ice bath and activate by addition of TBTU (1.34 g, 4.17 mmol, 1.9 equiv) and allow to stir for 5 min at 0-5° C. Add DCM (20 mL, 1.5 vols) to the resin followed by the addition of the activated Fmoc-amino acid solution. Stir the resulting mixture at about ambient temperature for 2 hours. Wash this resin with DMF (180 mL, 13 vols, twice), MTBE (180 mL, 13 vols, twice), and DMF (180 mL, 13 vols, twice) for 5 min each. Wash the resin with DCM (130 mL, 10 vols, 6 times, 5 mins each), before drying the resin in vacuo at 35° C., resulting in loaded resin (12.90 g, 0.203 mmol/g, 2.62 mmol, 121% yield).

Treat a portion of the resin (7.09 g, 0.203 mmol/g, 1.44 mmol) three times with 1 vol % TFA in DCM solution (70 mL, 10 vols) for 10 mins each at about ambient temperature, followed by washing with DCM (55 mL, 7.5 vols). Neutralize the cleavage fractions and washes with pyridine (3.02 g, 1.02:1 molar ratio to TFA). Combine and concentrate the fractions under vacuum to dryness at ≤35° C. Perform the reconstitution with ethanol (28 mL, 11% vol. of the combined filtrates) followed by concentration to dryness. Finally, stir the peptide in deionized water (105 mL, 40% vol. of the combined filtrates). Collect the solid crude peptide precipitate by filtration and wash with deionized water (4×50 mL). Wash the solid with n-heptane (3×100 mL), isolate and dry in vacuo at 40° C., resulting in the Preparation 11 as a white powder (4.54 g, 87.6 area %, 44.4 wt % pyridine•TFA, 48.7 wt %, 0.936 mmol, 65.0% yield, HRMS calcd for $C_{127}H_{192}N_{14}O_{28}$ expected 2361.4031, actual 2361.4021). The overall yield for preparation of Preparation 11 on resin is 71.3%.

Synthesis of Preparation 12

SEQ ID NO:12

Suspend Fmoc-Aib-O-CTC resin complex (19.16 g, 0.54 mmol/g, 10.35 mmol) in DMF (190 mL, 10 vols) for 20 min and then drain. Wash the resulting resin with DMF (190 mL, 10 vols) for 5 min and then drain. Combine piperidine (77.82 g), DBU (23.16 g), HOBt (18.09 g, 80 wt %), and DMF (1800 mL) to provide solution of 5% piperidine, 1.25% DBU, 1.0% HOBt/DMF as a deprotection solution. Remove the Fmoc group by treatment of the Fmoc-amino acid resin with deprotection solution (190 mL, 10 vols) twice, 10 min and 20 min respectively. Drain the de-Fmoc solution, then wash the resin twice with DMF, twice with MTBE, and again twice with DMF (190 mL, 10 vols for each wash).

Add DIEA (2.62 g, 20.3 mmol, 2.0 equiv) to a solution of Fmoc-Ile-OH (7.11 g, 10.1 mmol, 2.0 equiv) in DMF (85 mL). Cool the resulting solution to 0-5° C., add 6-chloro-benzotriazole-1-yloxy-tris-pyrrolidinophosphonium hexafluorophosphate (PyClock) (11.36 g, 20.06 mmol, 2.0 equiv) and dissolve completely. Add the activated solution to the H-Aib-O-CTC resin complex pre-swollen in DCM (30 mL, 1.5 vols) after standing for 3 to 5 minutes. Allow the reaction to warm up to ambient temperature and stir for 2 hours. Unreacted material is about 18% as indicated by assay assessment. Wash with DMF twice, MTBE twice, and DMF twice (190 mL, 10 vols for each). Add a solution of Fmoc-Ile-OH (10.63 g, 30.08 mmol, 6 equiv) in DMF (165 mL) to Oxyma (50 mL, 0.6 M in DMF, 30 mmol, 6 equiv), and DIC (50 mL, 0.66 M in DMF, 33 mmol, 6.6 equiv). Stir for 5 mins at about ambient temperature, and then add to the resin and stir for 18 hours. Add a mixture of pyridine, acetic anhydride, and DMF, to the resin and stir for 0.5 hour. Wash the resin with DMF (5×140 mL, 7 vols), more DMF (2×180 mL, 9 vols), MTBE (2×180 mL, 9 vols), then DMF (2×180 mL, 9 vols).

Conduct the rest of the chain assembly with standard Fmoc chemistry sequentially for the remaining amino acids. Generally, dissolve the Fmoc-amino acid (2.0 equiv), HOBt (3.42 g, 80 wt %, 2.0 equiv) in DMF (85 mL) followed by addition of DIEA (2.64 g, 2.0 equiv). Cool the resulting solution to 0-5° C. with an ice bath and activate by addition of TBTU (6.45 g, 2.0 equiv) and allow to stand for 3-5 min at 0-5° C. Add DCM (30 mL) to the resin followed by the addition of the activated Fmoc-amino acid solution. Stir the resulting mixture at rt for 2 hours. Wash the resulting resin twice with DMF, twice with MTBE and again twice with DMF (190 mL, 10 vols for each wash). Remove the Fmoc group by treatment of the Fmoc-amino acid resin with deprotection solution (190 mL, 10 vols) twice, 10 min and 20 min respectively. Wash the resin twice with DMF, twice with MTBE, and again twice with DMF (190 mL, 10 vols for each wash) after draining of the de-Fmoc solution.

Activate the tetramer Boc-Y-Aib-E(tBu)G-$_{OH}$ (12.25 g, 2.0 equiv) in DMF (50 mL) with Oxyma (30 mL of 0.6 M in DMF, 20 mmol, 2 equiv) and DIC (33 mL of 0.66 M, 22 mmol, 2.1 equiv) for 5 min to add the last four amino acids as a tetramer. Add this mixture to the resin and couple for 18 hours. Drain the mixture at the end of 18 hours and wash the resin with DMF (190 mL for 5 min each for 5 times). Add more tetramer (6.21 g, 1.0 equiv) in DMF (40 mL), activate with PyBOP (5.77 g, 1.1 equiv) and DIEA (3.32 g, 2.6 equiv) for 5 min before adding this mixture to the resin and stir for 4 hours. Drain the mixture at the end of 4 hours, wash with DMF (190 mL, 5 min each, 5 times). Cap the resin by adding with a mixture of DMF (105 mL), pyridine (13.48 g, 17 equiv), and acetic anhydride (14.27 g, 14 equiv) to the resin and stir for 1 hr. Wash the peptide resin after completion of the chain assembly, for 5 min each, five times with DMF (190 mL each time), six times with DCM (190 mL each time) and then dry under vacuum at 35° C., resulting in Preparation 12 resin complex (31.03 g, 0.2595 g/mmol theoretical, 8.05 mmol, 77.8% yield). Treat a portion of the Preparation 12 resin complex (15.975 g, 0.2595 mmol/g, 4.146 mmol) three times with 1 vol % TFA in DCM solution (160 mL, 10 vols) for 10 min each at ambient temperature, followed by washing with DCM (120 mL, 7.5 vols). Neutralize the cleavage fractions and washes with pyridine (4.74 g, 0.94:1 molar ratio to TFA). Combine and concentrate the fractions under vacuum to dryness at <35° C. Perform the reconstitution with ethanol (30 mL, 5% vol. of the combined filtrates) followed by concentration to dryness. Stir the peptide mechanically in deionized water (242 mL, 40% vol. of the combined filtrates) for 10 minutes. Collect the solid crude peptide by filtration and wash with deionized water (4×100 mL). Wash the solid with n-heptane (4×100 mL), isolate, and dry in vacuo at 35° C., resulting in the Preparation 12 as a white powder (9.38 g, 82.2 area %, 0.2 wt % pyridine•TFA, 82.1 wt %, 3.85 mmol, 92.8% yield, HRMS calcd for $C_{103}H_{165}N_{13}O_{26}$ expected 2000.1989, actual 2000.1968).

Synthesis of Preparation 13

SEQ ID NO:13

Into a flask under $N_2$ is added Preparation 9 (2.887 g, 70.2 wt %, 1.30 mmol) Preparation 10 (3.576 g, 57.4 wt %, 2.13 mmol, 1.63 equiv), DMSO (18.1 g, 16.4 mL), DMF (15.8 g, 16.7 mL), and DIEA (655 mg, 5.07 mmol, 3.89 equiv) with stirring until a golden solution results. The solution is cooled in ice water before PyBOP (1.414 g, 2.72 mmol, 2.08 equiv) is added. Remove the ice bath and allow the mixture to warm to ambient temperature. Monitor the reaction for about 5 hours to ensure adequate conversion. An aliquot of diethylamine (2.116 g, 28.9 mmol, 22.2 equiv) is added to the ambient temperature reaction mixture. The mixture is stirred for about an hour to provide about >99% conversion to Preparation 13. The product is precipitated by adding a <4° C. mixture containing saturated aq $NaHCO_3$ (50 mL) and deionized water (50 mL) to the reaction mixture. The mixture is stirred under cold conditions for at least about 15 minutes. A muddy white slurry is filtered. The wet cake is washed with deionized water (3x50 mL), followed by MTBE (6x50 mL), and drying at 40° C. in vacuo with $N_2$ purge for about 62 h. The process results in Preparation 13 (4.45 g, 60.4 area %, 16.4 area % dibenzofulvene, 1.18 mmol, 90.5% yield, HRMS calcd for $C_{119}H_{169}N_{21}O_{24}$ expected 2276.2649, actual 2276.2550) as light yellow solid.

Synthesis of Preparation 14

SEQ ID NO:14

An aliquot of Preparation 11 (3.012 g, 48.7 wt %, 0.621 mmol, 1.00 equiv) is added to a flask under $N_2$, with Preparation 13 (3.951 g, 60.4 wt %, 1.05 mmol, 1.69 equiv), DMSO (9.8 g, 8.9 mL), DMF (52.0 g, 55.0 mL), and DIEA (372 mg, 2.88 mmol, 4.63 equiv). The mixture is stirred until a golden solution results. Ice water cools the mixture to <10° C. Add an aliquot of PyBOP (742 mg, 1.42 mmol, 2.30 equiv) to the mixture. Remove the ice bath and allow the mixture to warm to about ambient temperature. Monitor the reaction for conversion to Preparation 14 for about 22 hours.

This produces about >96% conversion. Piperidine (530 mg, 6.22 mmol, 10.0 equiv) is added to the cooled reaction mixture when the temperature is <10° C. The mixture is stirred at ambient temperature for about 2 hours to provide >about 99% conversion to Preparation 14. The reaction mixture is added to another flask containing <4° C. 0.5N aq HCl (12.72 g, 6.23 mmol, 10.0 equiv) and deionized water (16.71 g), to provide precipitation of Preparation 14. The cold slurry is stirred for about 15 minutes and the white slurry is filtered. The wet cake is washed with deionized water (2×30 mL), saturated aq $NaHCO_3$ (2×30 mL), deionized water (3×30 mL), and MTBE (4×45 mL), and dried at 40° C. in vacuo with $N_2$ purge for about 17 h. The product, Preparation 14 (5.418 g, 48.9 area %, 0.603 mmol, 97.0% yield, HRMS calcd for $C_{231}H_{349}N_{35}O_{49}$. expected 4397.5893, actual 4397.6057) is obtained as a white powder.

Synthesis of Preparation 15

SEQ ID NO:15

An aliquot of Preparation 12 (671 mg, 82.1 wt %, 0.275 mmol, 1.23 equiv), is added to a flask under $N_2$. Preparation 14 (2.009 g, 48.9 area %, 10.7 area % isomer, 0.223 mmol, 1.00 equiv), DMSO (11.1 g, 10.0 mL), DMF (19.0 g, 20.1 mL), and DIEA (76 mg, 0.588 mmol, 2.63 equiv) are added to the flask with stirring resulting in a golden color solution. Add a 0.6M HOAt (619 mg, 0.384 mmol, 1.72 equiv) aliquot prior to cooling to −5° C. Add a sample of PyClock (220 mg, 0.397 mmol, 1.78 equiv). Allow the mixture to warm to about ambient temperature to provide about 84% conversion to Preparation 15. Isolate the product by adding the reaction mixture to ice-cold deionized water (548 mL) over 10 min, resulting in the precipitation of product. Rinse the reaction flask with DMF (5 mL) and add to the slurry. The slurry stirs for about 15 minutes, allowed to warm to about ambient temperature, and filtered. The wet cake is washed with deionized water (3×80 mL), and the white waxy solid dried at 35° C. for 3.5 days in vacuo, resulting in Preparation 15, (2.506 g, 41.6 area %, 0.163 mmol, 73.1% yield, HRMS calcd for $C_{334}H_{512}N_{48}O_{74}$ expected 6379.7777, actual 6379.8652) as a white powder.

EXAMPLE 2

Synthesis of Example 2

SEQ ID NO: 1

A sample of TFA (19.656 g, 13.03 mL), is added to a flask under $N_2$ with DCM (815 mg, 0.62 mL), DTT (434 mg), and TIPS (362 mg, 0.47 mL). Cool the mixture in ice water before adding water (468 mg, 0.47 mL). A sample of Preparation 15 (1016 mg, 39.0 area %, 0.0620 mmol) is added to this mixture at 2° C. to provide a solution. Warm the mixture to about ambient temperature and stir for about 2 hours. Add the reaction mixture to −15° C. MTBE (150 mL), rinsing the reactor with MTBE (3 mL). Centrifuge the slurry after about 10 min, decanting the supernatant. The wet cake is reslurried in MTBE (3×50 mL), centrifuging for each wash and decanting the supernatant. The wet cake is dried at 35° C. in vacuo resulting in Example 2 (784 mg, 26.5 area %, 0.0432 mmol, 69.7% yield, HRMS calcd for $C_{225}H_{348}N_{48}O_{68}$ expected 4810.5249, actual 4810.5642) as a white solid.

Synthesis of Preparation 16

SEQ ID NO:16

The synthesis uses Fmoc-Gly-OH 2-chloro trityl resin with a loading of 0.61 mmol/g. The general SPPS procedure is substantially as described herein. Preparation 16 results from soft cleavage of the peptide on resin as described herein using methods known to the artisan. Reconstitution of the concentrated material is performed with ethanol (5% vol. of the combined filtrates) and concentration to dryness. The peptide is triturated with stirring in water (40% vol. of the combined filtrates). The solid is isolated and dried under vacuum at 40° C. to a constant weight to yield 5.24 g (99%) of the Preparation 16 as a white powder.

Synthesis of Preparation 18

SEQ ID NO:17

The synthesis uses Fmoc-Ala-OH 2-chloro trityl resin with a loading of 0.50 mmol/g. The general SPPS procedure is used substantially as described herein with the following modifications:

| Cycle | Amino acid | SPPS conditions Solvent for couplings: DMF | Comments |
|---|---|---|---|
| 1 | (52S)-52-((((9H-fluoren-9-yl)methoxy)carbonyl)amino)-25-(tert-butoxycarbonyl)-2,2-dimethyl-4,23,28,37,46-pentaoxo-3,32,35,41,44-pentaoxa-24,29,38,47-tetraazatripentacontan-53-oic acid | 10 and 20 min De-Fmoc cycles with DBU/HOBt, 6 × 2 min post-dep washes, 1.7 AA/3.0 HOBt/3.0 TBTU/3.0 DIEA 2 h, rt. | Preparation 17 |
| 2 | Fmoc-L-Gln(Trt)-OH | 10 and 20 min De-Fmoc cycles, 6 × 2 min post-dep washes, 1. 3.0 AA/3.0 HOBt/3.0 TBTU/3.0 DIEA, 2 h, rt. 2. Recouple 1.5 AA/1.5 HOBt/1.5 TBTU/1.5 DIEA, 4 h, rt. | Capping performed at the end using: $Ac_2O$/Pyr mixture at rt, |
| 3 | Fmoc-L-Ala-OH | 10 and 20 min De-Fmoc cycles, 6 × 2 min post-dep washes, 2.0 AA/2.0 HOBt/2.0 TBTU/2.0 DIEA, 2 h, rt. | |
| 4 | Fmoc-L-Ile-OH | 10 and 20 min De-Fmoc cycles, 6 × 2 min post-dep washes, 2.0 AA/2.0 HOBt/2.0 TBTU/2.0 DIEA, 2 h, rt. | |
| 5 | Fmoc-L-Lys(Boc)-OH | 10 and 20 min De-Fmoc cycles, 6 × 2 min post-dep washes, 2.0 AA/2.0 HOBt/2.0 TBTU/2.0 DIEA, 2 h, rt. | |
| 6 | Fmoc-L-Asp(tBu)-OH | 10 and 20 min De-Fmoc cycles, 6 × 2 min post-dep washes, 2.0 AA/2.0 HOBt/2.0 TBTU/2.0 DIEA, 2 h, rt. | |

Preparation 18 Soft Cleavage:

A 42.13 g sample of peptide on resin intermediate is placed in a flask and treated 3 times with 10 volumes (400 mL) of 1% TFA/DCM for 10 min each followed by washing with DCM. Each treatment is quenched by addition of 4.4 mL of pyridine. The resulting solutions are combined concentrated in vacuo. The reconstitution is performed with ethanol (25 mL) followed by concentration to dryness to provide 56.6 g of foamy semisolid. A 400 mL volume of water is added 10 times to provide a slurry. The slurry is filtered and washed with water. The solid is isolated and dried under vacuum at 40° C. to a constant weight to yield 23.3 g of Preparation 18 as a white powder.

Synthesis of Preparation 17

((52S)-52-((((9H-fluoren-9-yl)methoxy)carbonyl) amino)-25-(tert-butoxycarbonyl)-2,2-dimethyl-4,23, 28,37,46-pentaoxo-3,32,35,41,44-pentaoxa-24,29, 38,47-tetraazatripentacontan-53-oic Acid)

Preparation 6 (80 g, 92 mmol), DIEA (17.53 mL, 101 mmol), TSTU (30.3 g, 101 mmol) and acetonitrile (1 L) are charge to a vessel and stirred at 23° C. for 17 h. The solution is concentrated, then the resulting orange residue is re-dissolved in EtOAC (1.6 L) then washed with 0.1 M HCl (2×1 L). The organic layer is washed with water (2×1 L) then dried over $MgSO_4$, filtered, and concentrated in vacuo to leave an orange oil (83 g). A second batch is run on the same scale and combined to deliver 123 g of crude oil. The intermediate ester (123 g, 110 g active, 113 mmol) is dissolved in EtOH (700 mL) then Fmoc-lysine (45.9 g, 125 mmol) and DIEA (21.70 mL, 125 mmol) are added and the reaction stirred 17 hr. After reaction completion, EtOH is removed in vacuo to leave an orange oil (201 g). The residue is dissolved in EtOAc (1.1 L) and washed with 0.1M HCl solution (3×400 mL), then aqueous $NaHCO_3$ (400 mL). The layers are separated then the organic layer is washed with saturated aqueous sodium chloride solution (1×400 mL). The organics are concentrated to produce an orange oil (~190 g). Acetone (400 ml) is added then the resulting suspension is filtered to remove inorganics. The mixture is concentrated then purified by normal phase chromatography (1.1 kg silica prepped with 60/40 heptane/acetone) and eluted with increasing polarity eluent (collecting ~3 L fractions). Fractions of at least 95 HPLC area % are combined and concentrated to provide thick yellow oil (70 g) of Preparation 17.

Synthesis of Preparation 19A

SEQ ID NO: 18

The synthesis uses Fmoc-Leu-OH 2-chloro trityl resin with a loading of 0.65 mmol/g. The general SPPS procedure is used with the following modifications:

| Cycle | Amino Acid | SPPS conditions Solvent for couplings: DMF |
|---|---|---|
| 1 | Fmoc-Aib-OH | 4 × 30 min De-Fmoc cycles, 6 × 2 min post-dep washes, 3.0 AA/3.3 DIC/3.0 Oxyma 8 h, rt. |
| 2 | Fmoc-L-Ile-OH | 4 × 30 min De-Fmoc cycles, 6 × 2 min post-dep washes, 3.0 AA/3.3 DIC/3.0 Oxyma 18 h, rt. |
| 3 | Fmoc-L-Ser(tBu)-OH | 3 × 30 min De-Fmoc cycles, 6 × 2 min post-dep washes, 3.0 AA/3.3 DIC/3.0 Oxyma 4 h, rt. |
| 4 | Fmoc-L-Tyr(tBu)-OH | 3 × 30 min De-Fmoc cycles, 6 × 2 min post-dep washes, 3.0 AA/3.3 DIC/3.0 Oxyma 4 h, rt |
| 5 | Fmoc-L-Asp(tBu)-OH | 3 × 30 min De-Fmoc cycles, 6 × 2 min post-dep washes, 3.0 AA/3.3 DIC/3.0 Oxyma 4 h, rt. |
| 6 | Fmoc-L-Ser(tBu)-OH | 3 × 30 min De-Fmoc cycles, 6 × 2 min post-dep washes, 3.0 AA/3.3 DIC/3.0 Oxyma 4 h, rt. |
| 7 | Fmoc-L-Thr(tBu)-OH | 3 × 30 min De-Fmoc cycles, 6 × 2 min post-dep washes, 3.0 AA/3.3 DIC/3.0 Oxyma 4 h, rt. |
| 8 | Fmoc-L-Phe-OH | 3 × 30 min De-Fmoc cycles, 6 × 2 min post-dep washes, 3.0 AA/3.3 DIC/3.0 Oxyma 4 h, rt |
| 9 | Fmoc-Gly-Thr ($\psi^{Me,Me}$Pro)-OH | 4 × 30 min De-Fmoc cycles, 6 × 2 min post-dep washes, 3.0 AA/3.3 DIC/3.0 Oxyma 18 h, rt. |
| 10 | Fmoc-L-Glu(tBu)-OH | 4 × 30 min De-Fmoc cycles, 6 × 2 min post-dep washes, 3.0 AA/3.3 DIC/3.0 Oxyma 8 h, rt. |
| 11 | Fmoc-Aib-OH | 4 × 30 min De-Fmoc cycles, 6 × 2 min post-dep washes, 3.0 AA/3.3 DIC/3.0 Oxyma 18 h, rt. |
| 12 | Boc-L-Tyr(tBu)-OH | 4 × 30 min De-Fmoc cycles, 6 × 2 min post-dep washes, 3.0 AA/3.3 DIC/3.0 Oxyma 18 h, rt. |

The pseudoproline derived Preparation 19A can be processed to Example 3 in analogous manner as Preparation 19B, as described herein.

Synthesis of Preparation 19B

SEQ ID NO: 19

The synthesis uses Fmoc-Leu-OH 2-chloro trityl resin with a loading of 0.65 mmol/g. Preparation 19B is prepared using the SPPS procedure substantially as described herein.

| Cycle | Amino acid | SPPS conditions Solvent for couplings: DMF | Comments |
|---|---|---|---|
| 1 | Fmoc-Aib-OH | 4 × 30 min De-Fmoc cycles, 6 × 2 min post-dep washes, 3.0 AA/3.3 DIC/3.0 Oxyma 8 h, rt. | |
| 2 | Fmoc-L-Ile-OH | 4 × 30 min De-Fmoc cycles, 6 × 2 min post-dep washes, 3.0 AA/3.3 DIC/3.0 Oxyma 18 h, rt. | |
| 3 | Fmoc-L-Ser(tBu)-OH | 3 × 30 min De-Fmoc cycles, 6 × 2 min post-dep washes, 3.0 AA/3.3 DIC/3.0 Oxyma 4 h, rt. | |
| 4 | Fmoc-L-Tyr(tBu)-OH | 3 × 30 min De-Fmoc cycles, 6 × 2 min post-dep washes, 3.0 AA/3.3 DIC/3.0 Oxyma 4 h, rt | |
| 5 | Fmoc-L-Asp(tBu)-OH | 3 × 30 min De-Fmoc cycles, 6 × 2 min post-dep washes, 3.0 AA/3.3 DIC/3.0 Oxyma 4 h, rt. | |
| 6 | Fmoc-L-Ser(tBu)-OH | 3 × 30 min De-Fmoc cycles, 6 × 2 min post-dep washes, 3.0 AA/3.3 DIC/3.0 Oxyma 4 h, rt. | |
| 7 | Fmoc-L-Thr(tBu)-OH | 3 × 30 min De-Fmoc cycles, 6 × 2 min post-dep washes, 3.0 AA/3.3 DIC/3.0 Oxyma 4 h, rt. | |
| 8 | Fmoc-L-Phe-OH | 3 × 30 min De-Fmoc cycles, 6 × 2 min post-dep washes, 3.0 AA/3.3 DIC/3.0 Oxyma 4 h, rt | |

-continued

| Cycle | Amino acid | SPPS conditions Solvent for couplings: DMF | Comments |
| --- | --- | --- | --- |
| 9 | Fmoc-L-Thr(tBu)-OH | 3 × 30 min De-Fmoc cycles, 6 × 2 min post-dep washes, 3.0 AA/3.3 DIC/3.0 Oxyma 4 h, rt | |
| 10 | Boc-Tyr(tBu)-Aib-Glu(tBu)-Gly-OH | 4 × 30 min De-Fmoc cycles, 6 × 2 min post-dep washes, 1.2.0 AA/2.2 DIC/2.0 Oxyma 6 h, rt. 2. recouple, 1.0 AA/1.1 PyBOP/ 2.5 DIPEA, 4 h, rt | Capping performed at the end using: $Ac_2O$/Pyr mixture |

Preparation 19B Soft Cleavage:

Preparation 19B is prepared using soft cleavage of the resin bound 19B substantially as described herein using methods known to the artisan. See for example, the method of Preparation 18. The resulting solid is isolated and dried under vacuum at 30-40° C. to a constant weight to yield 2.94 g of the product as a light yellow powder.

Synthesis of Preparation 20

SEQ ID NO:20

To a solution of Preparation 1 (4.25 g, 4.166 mmol) and Preparation 16 (5.00 g, 3.340 mmol) in DMSO/DMF (1:1, 200 mL) is added PyBOP (2.60 g, 5.00 mmol) and DIEA (1.75 mL, 10.0 mmol) at ambient temperatures. The solution is stirred for 18 hours and then quenched by the addition of an excess of diethylamine (10.0 mL). The quenched solution is stirred for 2 hours and then slowly added to a solution of saturated aqueous sodium bicarbonate/water (1:1, 300 mL) at 0° C. The resulting precipitate is stirred for 10 minutes and then collected by filtration. The filtrate is washed successively with water (3×150 mL) followed by methyl tert-butyl ether (3×150 mL). The solid is dried under vacuum at 40° C. to afford Preparation 20 as a white solid (5.30 g, 69% yield, HRMS calcd for $C_{119}H_{169}N_{21}O_{24}$ expected 2276.2649, actual 2276.2652).

Synthesis of Preparation 21

SEQ ID NO:21

To a solution of Preparation 20 (1.00 g, 0.44 mmol) and Preparation 18 (0.90 g, 0.40 mmol) in DMSO/DMF (1:1, 20 mL) is added PyBOP (314 mg, 0.30 mmol) and DIEA (0.21 mL, 1.20 mmol) at ambient temperatures. The solution is stirred for 18 hours and then quenched with piperidine (0.79 mL, 4.00 mmol). The quenched solution is stirred for 2 hours and then cooled to 0° C. and quenched with a dilute solution of HCl (50 mL). The resulting slurry is stirred for 10 minutes and the solid is collected by filtration. The filtrate is washed successively with saturated aqueous sodium bicarbonate (2×50 mL), water (3×50 mL) followed by methyl tert-butyl ether (3×50 mL). The solid is dried under vacuum at 40° C. for 18 hours to afford Preparation 21 as a white solid (1.80 g, 106% yield, HRMS calcd for $C_{225}H_{338}N_{34}O_{48}$ expected 4284.5053, actual 4284.5062).

Synthesis of Preparation 22

SEQ ID NO:22

To a solution of Preparation 21 (214 mg, 0.05 mmol) and Preparation 19B (116 mg, 0.055 mmol) in DMSO/DMF (1:1, 3 mL) is added PyBOP (57 mg, 0.11 mmol) and DIEA (58 μL, 0.33 mmol) at ambient temperatures. The solution is stirred for 18 hours and then quenched with a 1:1 mixture of saturated aqueous sodium bicarbonate and water (10 mL). The resulting slurry is stirred for 10 minutes and the resulting solid is collected by filtration. The solid is washed with water (3×10 mL) and the solid is dried under vacuum at 40° C. to afford Preparation 22 (285 mg, 89% yield, HRMS calcd for $C_{334}H_{512}N_{48}O_{74}$ expected 6379.7777, actual 6379.7730).

EXAMPLE 3

Synthesis of Example 3

SEQ ID NO: 1

A solution of TFA (2.3 mL), water (0.1 mL), triisopropylsilane (0.1 mL) and DTT (75 mg) is cooled to 0° C. To the solution is charged Preparation 22 (100 mg, 0.015 mmol) and the reaction mixture is allowed to warm to ambient temperatures and stirred for 2 hours. The resulting mixture is poured into a precooled (−20° C.) solution of methyl tert-butyl ether (25 mL). The resulting precipitate is maintained for 15 minutes at −20° C. for 15 minutes and the slurry is centrifuged and washed with methyl tert-butyl ether (2×25 mL). The solid is dried under vacuum at 35° C. for 18 hours to obtain Example 3 as a white solid (71 mg, 93% yield, HRMS calcd for $C_{225}H_{348}N_{46}O_{68}$ expected 4810.5249, actual 4810.5036).

Step 1

Step 1: A feed solution of Preparation 25 (1.05 equiv) is prepared in 5 vols of DMSO/ACN (90:10 vol/vol). A second feed solution of Preparation 26 is prepared in 20 vol of DMSO/ACN (90:10 vol/vol). A third feed solution is prepared of PyOxim (1.5 equiv) in 3 vols ACN. A fourth stream of DIEA (4 equiv) in ACN is prepared. The first three streams are pumped into a mixer and at the outlet of the mixer the DIEA is combined and the mixture is pumped through another mixer and through a plug flow reactor for a 2 h residence time in a 20° C. constant temperature bath. At the outlet of the reactor, acetic acid may be added to consume the remaining PyOxim (1-Cyano-2-ethoxy-2-oxoethylideneaminooxy-tris-pyrrolidino-phosphonium hexafluorophosphate). After >2 h, neat diethylamine (10 equiv) is added and mixed through a mixer. This stream progressed into a second plug flow reactor with a 1 h residence time in a 20° C. constant temperature bath. The product solution of Preparation 27 is collected and sent through a nanofiltration with 70/30 DMSO/ACN solution to remove reagents for 10-20 diavolumes. A feed solution of Preparation 25, 2.40 kg, 96.7 wt. %, 2.274 mol) is prepared by dissolving the solid in DMSO (13.88 kg, 12.62 L) and diluting the solution with ACN (1.09 kg, 1.39 L), creating a solution of Preparation 25 (114.3 mg/mL, 0.112 M) in 90:10 DMSO:ACN vol/vol. A second feed solution of Preparation 26 (SEQ ID NO:26, 2.79 kg, 98.6 wt. %, 1.836 mol) is prepared by dissolving the solid in DMSO (54.8 kg, 49.8 L) and diluting with ACN (4.3 kg, 5.47 L), creating a solution of Preparation 26 (45.5 mg/mL, 0.030 M) in 90:10 DMSO: ACN vol/vol. A third feed solution is prepared of PyOxim (4.5 kg, 8.53 mol) in ACN (47.33 kg, 60.22 L) creating a solution of 0.132 M. DIEA is added as a neat liquid. The solution of Preparation 25 (14.91 L, 1.704 kg, 1.670 mol, 0.95 equiv, 5.9 g/min) and Preparation 26 (58.46 L, 2.660 kg, 1.750 mol, 1.00 equiv, 22.5 g/min) and PyOxim (1.4 equiv, 5.4 g/min) streams are pumped into a mixer combined with neat DIEA (4.0 equiv, 0.446 mL/min) at 20° C. The mixture is pumped through another mixer and through a plug flow reactor for a 3 h residence time in a 20° C. temperature bath and collected over 42.9 h, resulting in 88.6 kg of product solution.

Nanofiltration is a membrane-based filtration process that is used to separate chemical species based on their size and molecular weight differences. The product solution of Preparation 27 contains reagents (diethylamine, PyOxim, DIEA, etc.) and unwanted by-products (e.g. dibenzofulvene) that are desired to be removed prior to proceeding to the next step. Nanofiltration is applied to remove undesired species (molecular weight <500 Da).

The product solution of Preparation 27 is charged to a NF feed tank and pumped around in a recirculation loop through a heat exchanger and a nanofiltration unit containing a suitable membrane (ceramic or polymeric) to cause the desired separation. The undesired species are removed in the permeate and collected separately or discarded to waste. In order to maintain a constant volume in the NF tank, fresh solvent, i.e. 70:30 vol/vol DMSO/ACN, is continuously pumped in to match the permeate rate drawn out. Preparation 27 product solution is purified through nanofiltration is carried directly into Step 2.

Fmoc protected Preparation 27 solution in DMSO/ACN (88.6 kg) and diethylamine (1.34 kg) is added to a reactor. The mixture is stirred at 20° C. for 2 h, resulting in Preparation 27 (87.6 L, 38.45 mg/mL, 3.37 kg, 1.48 mol). The product solution of Preparation 27 is charged to a nanofiltration feed tank and then is pumped around in a recirculation loop through a heat exchanger and a nanofiltration unit containing a suitable membrane (ceramic or polymeric) to cause the desired separation. The undesired species are removed in the permeate side and collected separately or discarded to waste. The operation is continued until sufficient removal of undesired impurities is obtained. In order to maintain a constant volume in the nanofiltration tank, fresh 70:30 vol/vol DMSO/ACN is continuously pumped in to match the permeate rate drawn out. This results in Preparation 27 in DMSO/ACN (72.4 L, 40.8 mg/mL, 2.95 kg, 1.30 mol, 78.1% yield across the coupling, deFmoc, and nanofiltration).

Step 1 Exemplification—Analytical Results.

HPLC confirms conversion of Preparation 25 and Preparation 26 to form Preparation 27. The method of analysis uses a phenyl hexyl stationary phase column at 65° C. (2.1 mm i.d.×150 mm×1.7-micron particle size) with a 2-98% B gradient of 0.1% TFA in water and acetonitrile over 12 minutes. UV detection at 214 nm is used for this material.

Table A.1 shows high resolution mass spectrometry data collected for the product of the Step 1 coupling reaction (Fmoc-protected Preparation 27) and the product of the Step 1 deprotection reaction (Preparation 27). Mass accuracy is the metric used to confirm the match of the measured species to the predicted species.

TABLE A.1

Confirmation of measured Fmoc-protected Preparation 27 and Preparation 27 via mass accuracy calculated using high resolution mass spectrometry data.

| Compound | Chemical Formula | Theoretical Monoisotropic Mass (neutral) | Observed Ion m/z | Charge State | Calculated Monoisotropic Mass (neutral) | Mass Accuracy (ppm) |
|---|---|---|---|---|---|---|
| Fmoc Protected Preparation 27 | $C_{134}H_{179}N_{21}O_{26}$ | 2498.333 | 2499.3402 | 1 | 2498.3329 | 0.05 |
| Preparation 27 | $C_{119}H_{169}N_{21}O_{24}$ | 2276.2649 | 2277.2743 | 1 | 2276.267 | 0.9 |

Step 2

SEQ ID NO: 28 + SEQ ID NO: 27

SEQ ID NO: 29

Schematic A.2 Synthesis of Preparation 29 (SEQ ID NO: 29) from Fragments Preparation 27 (SEQ ID NO:27) and Preparation 28 (SEQ ID NO:28)

Step 2

Step 2 Chemistry:

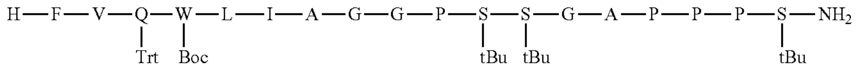

Preparation 27

-continued

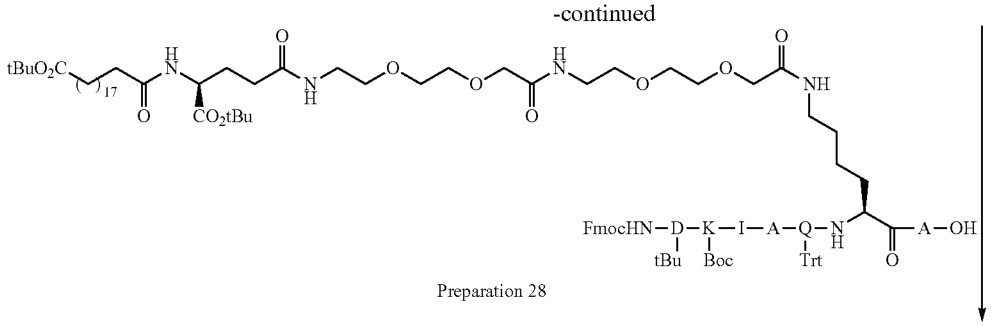

Preparation 28

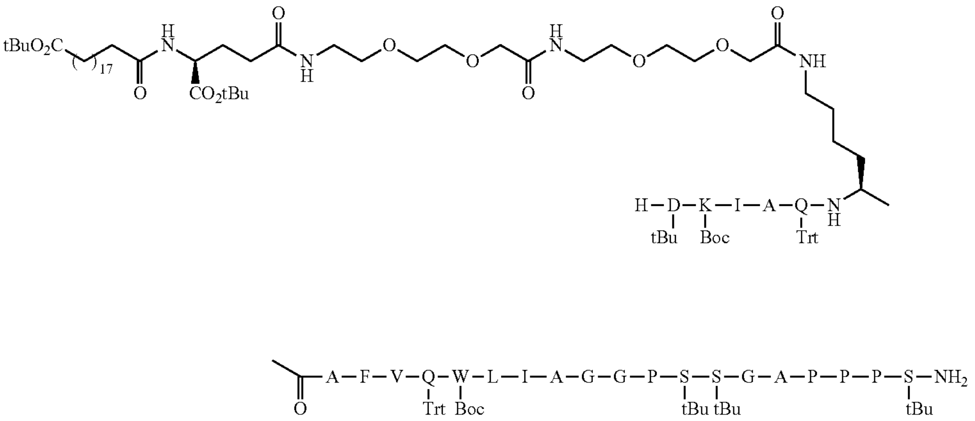

Preparation 29

Step 2: A feed solution of Preparation 28 (1.15 equiv) is prepared in 10 vol of DMSO/ACN (90:10 vol/vol). A second feed solution is prepared of PyOxim (2 equiv) in 1 vol ACN. A third stream of DIEA (3 equiv) in ACN is prepared (5 wt % solution). The solution of Preparation 27 from Step 1 and the Preparation 28 and PyOxim streams are pumped into a mixer and at the outlet of the mixer the DIEA is combined and the mixture is pumped through another mixer and through a plug flow reactor for a 2 h residence time in a 20° C. constant temperature bath. At the outlet of the reactor, acetic acid may be added to consume the residual PyOxim. After >2 h, neat diethylamine (10 equiv) is added and mixed through a mixer. This stream progresses into a second plug flow reactor with a 1 h residence time in a 20° C. constant temperature bath. The product solution of Preparation 29 is collected and sent through a nanofiltration with DMF solution as a diafiltrant to remove reagents for 10-20 diavolumes.

A feed solution of Preparation 28 (4.68 kg, 98.9 wt. %, 2.058 mol) is prepared by dissolving the solid in DMSO (41.75 kg, 37.95 L) and diluting the solution with ACN (3.3 kg, 4.20 L), creating a solution of Preparation 28 (94.7 mg/mL, 0.0421 M) in 90:10 DMSO:ACN vol/vol. A second feed solution is prepared of PyOxim (3.0 kg, 5.69 mol) in ACN (11.81 kg, 15.03 L) creating a solution of 0.327 M. DIEA is added as a neat liquid. The solution of Preparation 27 from Step 1 (73.86 L, 41.2 mg/mL, 3.04 kg, 1.336 mol, 0.0181 M, 1.0 equiv, 29.9 g/min) and Preparation 28 (1.3 equiv, 17.7 g/min) and PyOxim (2.1 equiv, 2.9 g/min) streams are pumped into a mixer and at the outlet of the mixer the stream is adjusted to 20° C. and combined with neat DIEA (4.0 equiv, 0.374 mL/min) at 20° C. The mixture is pumped through another mixer and through a plug flow reactor for a 3 h residence time in a 20° C. temperature bath and collected over 43.2 h, resulting in 129.35 kg of Preparation 29 product solution.

A nanofiltration process substantially as described herein above, uses the product solution of Preparation 29 instead of the product solution of Preparation 27.

A nanofiltration process using Fmoc-protected Preparation 29 solution in DMSO/ACN is conducted substantially as described herein. Fmoc-protected Preparation 29 (129.35 kg) and diethylamine (2.0 kg) is added to a reactor for nanofiltration. Nanofiltration process results in Preparation 29 in DMF (98.85 L, 42.24 mg/mL, 4.18 kg, 0.974 mol, 73.1% yield across the coupling, deFmoc, and nanofiltration).

HPLC confirms the synthesis of Preparation 29 from Preparation 28 and Preparation 27. The method of analysis uses a C4 stationary phase column at 65° C. (2.1 mm i.d.×150 mm×1.7-micron particle size) with a 25-98% B gradient of 0.1% TFA in water and acetonitrile over 12 minutes. UV detection at 214 nm is used for this material.

Table A.3 shows high resolution mass spectrometry data collected for the product of the Step 2 coupling reaction (Fmoc protected Preparation 29) and the product of the Step 2 deprotection reaction (Preparation 29). Mass accuracy confirms the measured species product. monoisotopic mass of the neutral species.

TABLE A.3

Confirmation of measured Fmoc-protected Preparation 29 and Preparation 29 via mass accuracy calculated using high resolution mass spectrometry data.

| Compound | Chemical Formula | Theoretical Monoisotropic Mass (neutral) | Observed Ion m/z | Charge State | Calculated Monoisotropic Mass (neutral) | Mass Accuracy (ppm) |
|---|---|---|---|---|---|---|
| Fmoc Protected Preparation 29 | $C_{240}H_{348}N_{34}O_{50}$ | 4506.5734 | 2254.294 | 2 | 4506.5735 | 0.02 |
| Preparation 29 | $C_{225}H_{338}N_{34}O_{48}$ | 4284.5053 | 2143.2596 | 2 | 4284.5046 | 0.17 |

Step 3

Schematic A.3 Synthesis of Preparation 31 (SEQ ID NO:31) from Fragments Preparation 30 (SEQ ID NO:30) and Preparation 29 (SEQ ID NO:29)

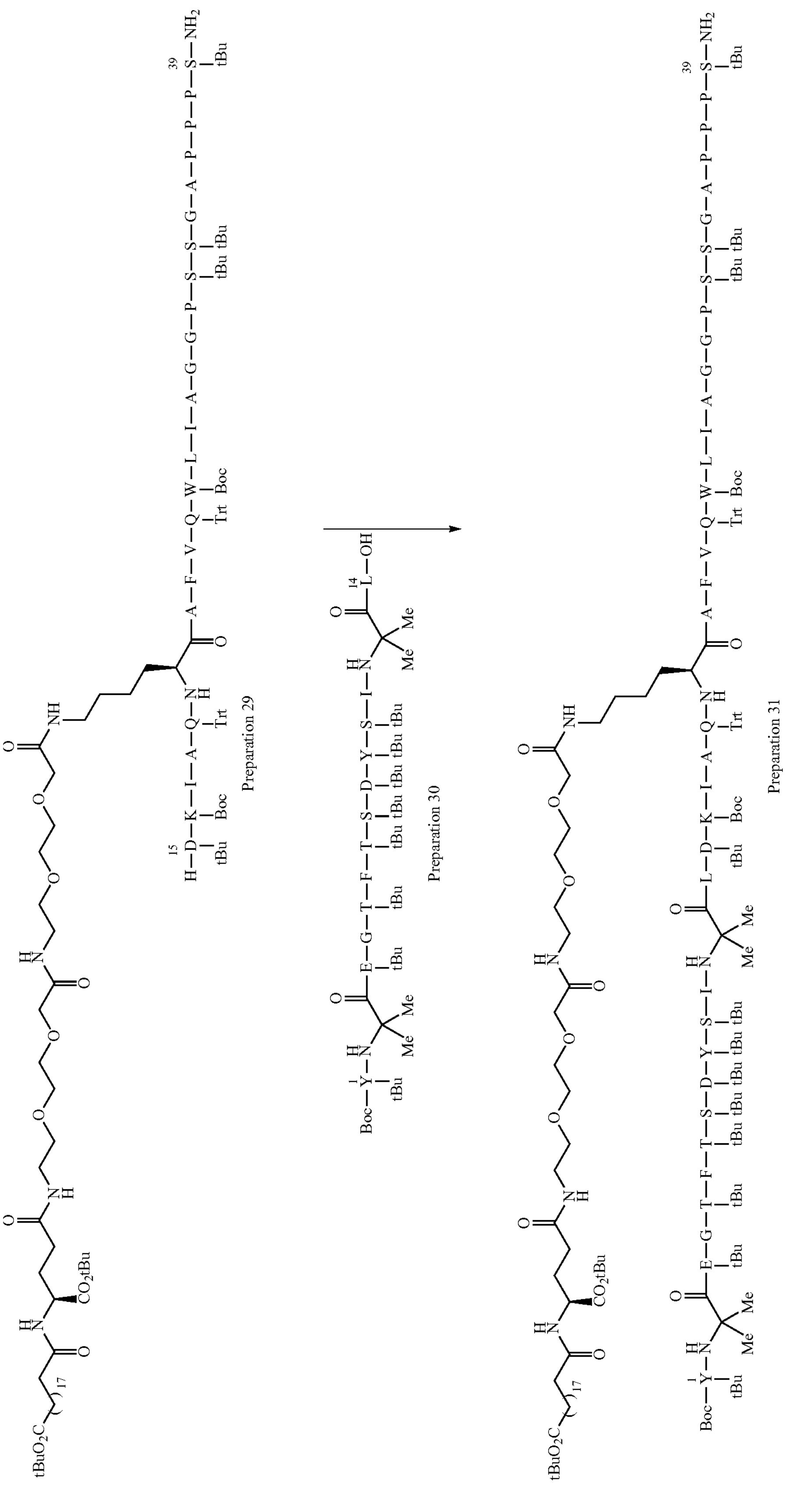
Preparation 29
Preparation 30
Preparation 31

Step 3 Batch Process Description: To a nanofiltered DMF solution of Preparation 29 (2.249 g, 46.5 mg/g, 104.6 bmg, 0.0244 mmol) and Preparation 30 (71.5 mg, 90.6 area %, 0.0306 mmol) in DMF (0.3068 g, 0.325 mL) at −5° C. is added a 5.0 wt % DIEA solution in DMF (114.0 mg, 5.70 mg DIEA, 0.0441 mmol, 1.8 equivalents) and a 10.1 wt % solution of (1-[bis(dimethylamino)methylene]-1H-1,2,3-triazolo[4,5-b]pyridinium 3-oxide hexafluorophosphate (HATU) in DMF (154.9 mg, 15.59 mg HATU, 0.0410 mmol, 1.7 equivalents). The solution is stirred for 4 hours at −5° C. and then quenched with 5 wt % aqueous sodium bicarbonate (5.295 g, 4.8 mL) at ambient temperature, which is added over 15 minutes. The resulting slurry is stirred at 0° C. for 15 minutes, and the resulting solid is collected by filtration. The solid is washed with water (4×2 mL) and then washed with MTBE (4×2 mL). The gummy solid is dried under vacuum at 35° C. to afford Preparation 31 (219.7 mg, 47.6 area %, 0.0164 mmol, 67.1% yield).

A feed solution of Preparation 30 is prepared in 10 vols of DMF. A second feed solution is prepared of HATU (1.8 equiv) in at 10 wt. % solution with ACN. A third stream of DIEA (2.5 equiv) in DMF is prepared (5 wt. % solution). The solution of Preparation 29 from Step 2 and the Preparation 30 and DIEA streams are pumped into a mixer and at the outlet of the mixer the stream is cooled and combined with cooled HATU solution. The mixture is pumped through another mixer and through a plug flow reactor for a 3 h residence time in a −5° C. constant temperature bath and collected. A solution of brine/bicarb (aqueous solution of 17 wt. % aq sodium chloride, 0.5 wt. % aq sodium bicarbonate) 19% salt load by weight is prepared. The product solution of Preparation 31 in DMF is then pumped into a mixed product mixed suspension reactor (MSMPR) along with the salt solution to form a precipitation. The tau in the mixed product mixed suspension reactor is 1 hour. The second MSMPR is run colder for a 1 h tau and this slurry is charged to a filter intermittently. The slurry is washed with water and dried under vacuum at 35° C.

A feed solution of Preparation 30 (9.42 kg, 83.6 wt. %, 3.72 mol) is prepared in DMF (54.12 kg), creating a feed of 0.0563 M. A second feed solution is prepared of HATU (1.15 kg, 3.02 mol) in ACN (10.4 kg), creating a feed of 0.215 M. DIEA is added as a neat liquid. The solution of Preparation 29 from Step 2 (98.85 L, 42.24 mg/mL, 4.18 kg, 0.975 mol, 0.0099 M, 1.0 equiv, 40.2 g/min) and the Preparation 30 (1.3 equiv, 9.2 g/min) and DIEA (2.1 equiv, 0.152 mL/min) streams are pumped into a mixer. At the outlet of the mixer, the stream is cooled to 0° C. and combined with cooled HATU solution (2.0 equiv, 3.2 g/min) at 0° C. The mixture is pumped through another mixer and through a plug flow reactor for a 4 h residence time in a 0° C. temperature bath and collected over 42 h, resulting in 131.8 kg of product solution. The product solution is precipitated in two sections. A solution of 17 wt. % aq NaCl/0.5 wt. % aq $NaHCO_3$ (29 kg) is combined with DMF (13.2 kg) in an inerted reactor and cooled to not more than 20° C. The product solution in DMF (66.6 kg) is then co-added with 17 wt. % aq NaCl/0.5 wt. % aq $NaHCO_3$ (34.4 kg) to the reactor over 1 h, maintaining 20° C., resulting in the precipitation of product, Preparation 31. The slurry is cooled to 5° C. over 1 h, before water (32.2 kg total) is added in two portions. The 5° C. slurry is stirred for 0.5 h, before the slurry is filtered. The wet cake is reslurried in water (63.9 kg) for 0.5 h and filtered. The second section of the product solution is precipitated in a comparable fashion. A solution of 17 wt. % aq NaCl/0.5 wt. % aq $NaHCO_3$ (29 kg) and DMF (13.55 kg) are combined in a reactor and cooled to not more than 20° C. The second section of the product solution in DMF (65.2 kg) is co-added with 17 wt. % aq NaCl/0.5 wt. % aq $NaHCO_3$ (36.8 kg) to the reactor over 1 h, maintaining 20° C., resulting in the precipitation of product, Preparation 31. The slurry is cooled to 5° C. over 1.25 h, before water (32.1 kg total) is added in two portions. The slurry is stirred for 0.5 h, before the slurry is filtered on top of the first wet cake. The combined wet cake is reslurried with water twice (64 kg each) for 0.5 h each and filtered. This is followed by two displacement washes with water (64 kg each). The combined washed wet cake is blown with $N_2$ and then dried under vacuum at 38° C. until the K.F. is <4 wt. %, resulting in Preparation 31 (10.34 kg, assumed 60% potency, 0.972 mol, assumed 100% yield).

EXAMPLE 3

Tirzepatide (SEQ ID NO:1)

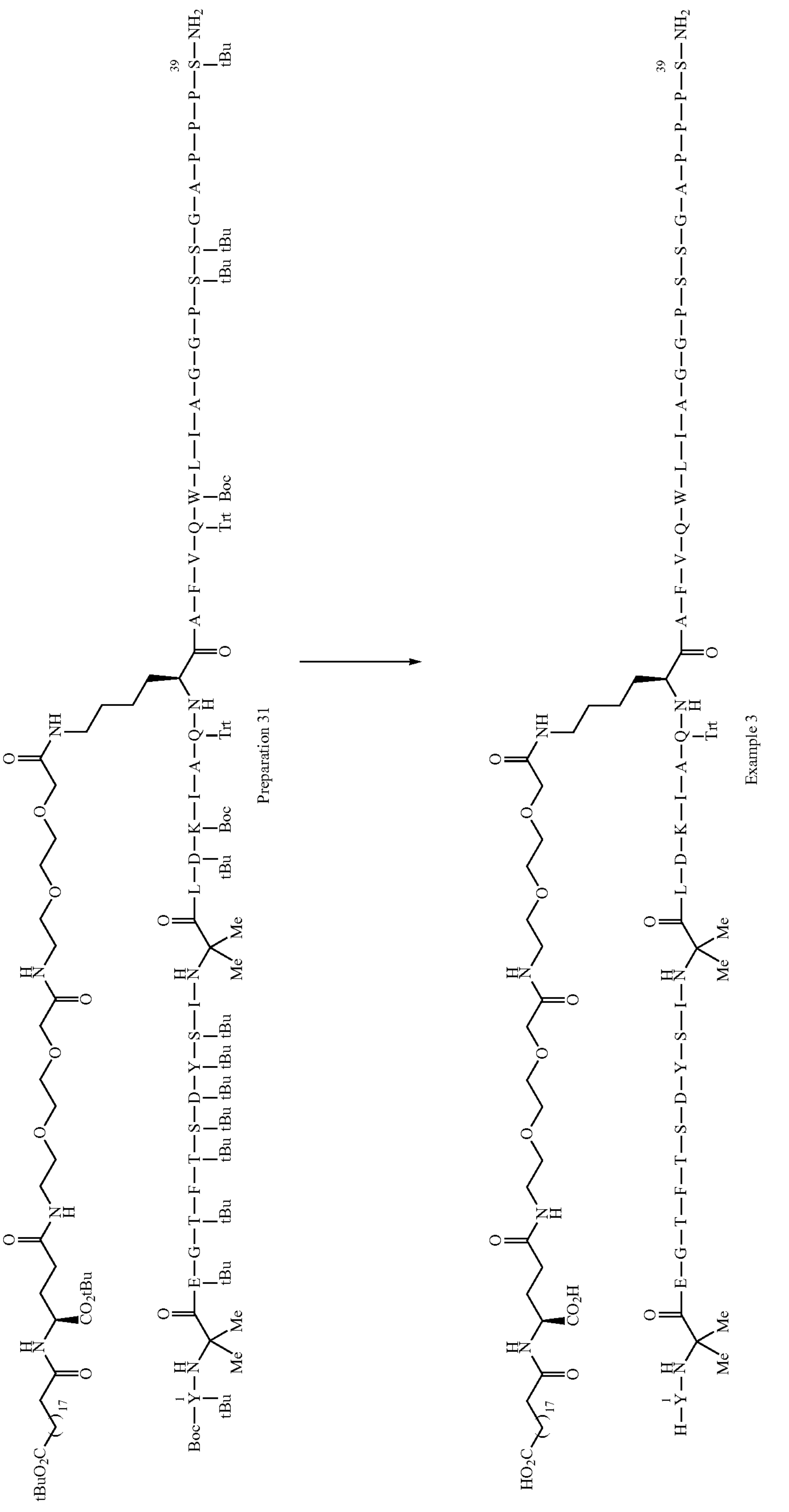
Preparation 31
Example 3

A solution of TFA (2.3 mL), water (0.1 mL), triisopropylsilane (TIPS, 0.1 mL) and Dithiothreitol (DTT, 75 mg) is cooled to 0° C. To the solution is charged Preparation 31 (100 mg, 0.015 mmol) and the reaction mixture is allowed to warm to ambient temperature and stirred for 2 hours. The resulting mixture is poured into a precooled (−20° C.) solution of MTBE (25 mL). The resulting precipitate is maintained for 15 minutes at −20° C. for 15 minutes and the slurry is centrifuged and washed with MTBE (2×25 mL). The solid is dried under vacuum at 35° C. for 18 hours to obtain Example 3 as a white solid (71 mg, 93% yield, HRMS calcd for $C_{225}H_{348}N_{46}O_{68}$ expected 4810.5249, actual 4810.5036).

To an inerted reactor at 15° C. is added DCM (27.3 kg, 20.6 L), water (4.1 kg), Preparation 31 (10.34 kg, assumed 60% potency, 0.972 mol), and DTT (3.10 kg). In a separate inerted reactor is added TFA (154.1 kg, 103.4 L) and TIPS (3.2 kg, 4.2 L). The TFA/TIPS solution is added to the slurry of Preparation 31, DCM, water, and DTT within 0.25 h, forming a colorless solution, and warmed and held at 20° C. for 3 h. After 3 h at 20° C., the reactor is cooled to −10° C. In a separate reactor MTBE (382.4 kg, 516.8 L) is added, which is cooled to −20° C. A portion of this cold MTBE (91.8 kg, 124.1 L) is added to the cold reaction solution over 2 h, maintaining −5° C. to −18° C. The remaining cold MTBE (294.3 kg, 397.7 L) is added over 1.5 h maintaining −5° C. to −18° C., resulting in precipitation of Example 3. The slurry is adjusted to 0° C. and held for >0.5 h, before it is filtered in three sections. The combined wet cake is reslurried with MTBE (114.7 kg, 155 L) two times and filtered before a final MTBE displacement wash (114.7 kg, 155 L). The wet cake is dried at 28° C. until <4.5 wt. % MTBE is measured. This resulted in Example 3 (7.77 kg, 46.8 wt. %, 0.755 mol, 77.7% yield).

EXAMPLE 4A (LINEAR SPPS)

Tirzepatide (SEQ ID NO:1)

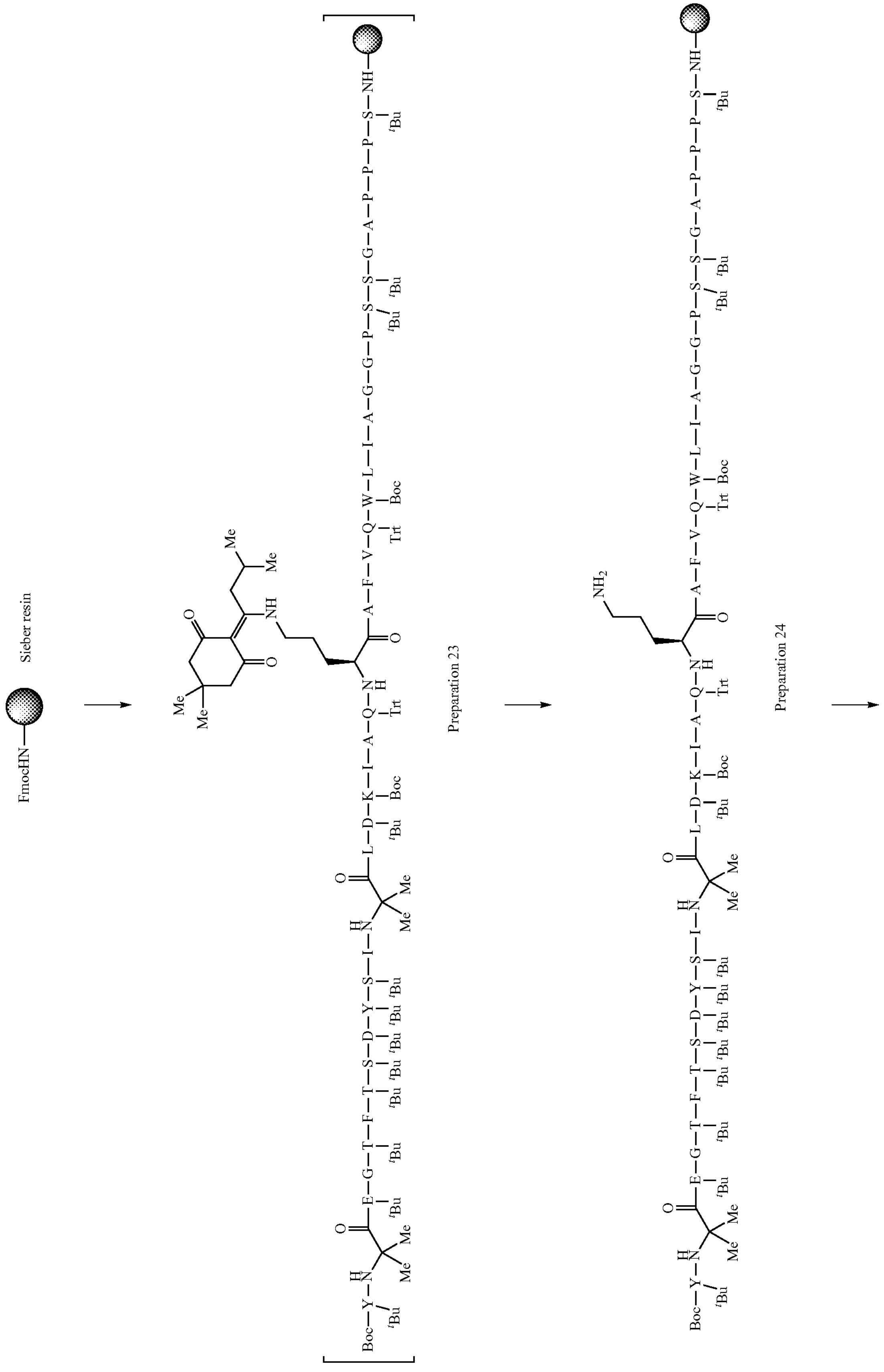
Sieber resin
Preparation 23
Preparation 24

-continued
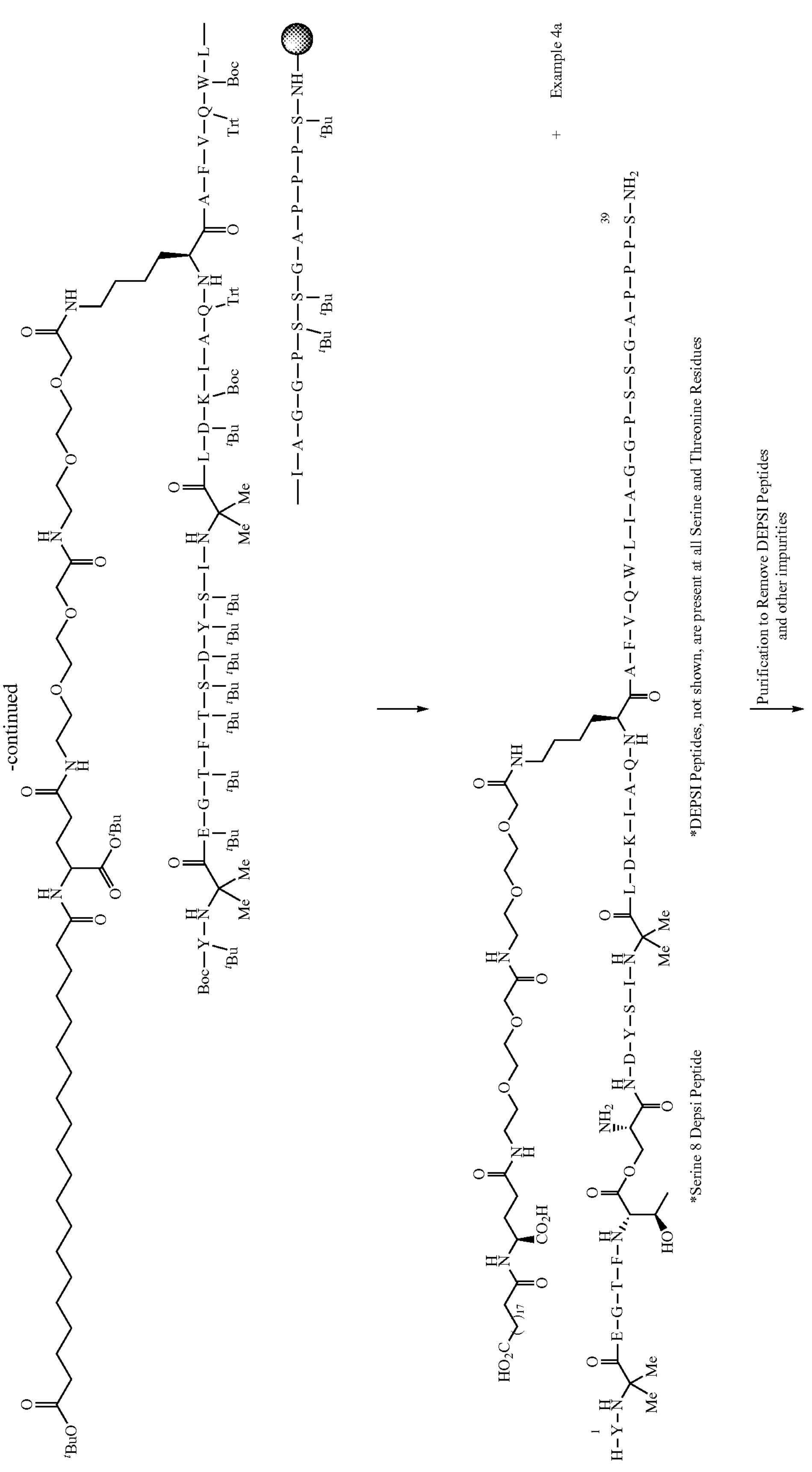

-continued
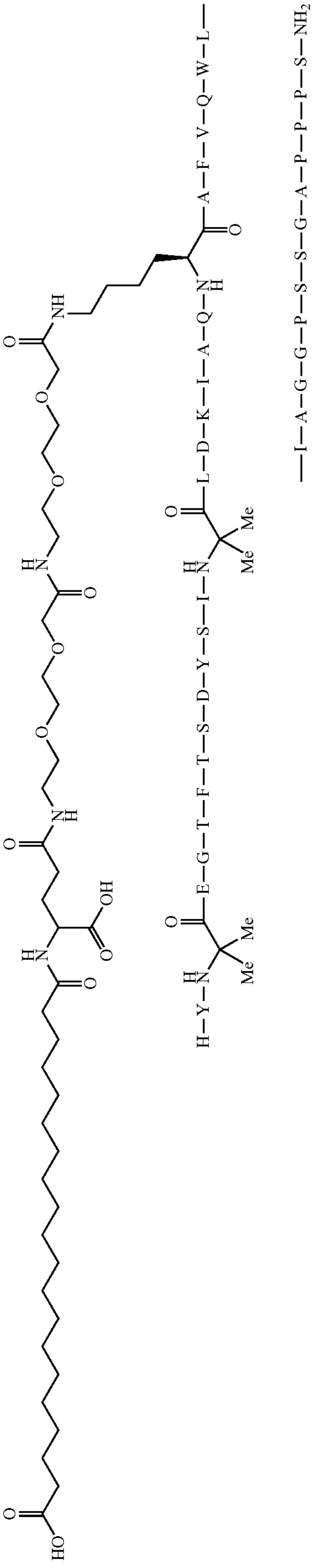
Example 4A

Fmoc Sieber resin (17 kg, 0.76 mmol/g) is charged to a reactor. The resin is swelled with DMF, stirred for 2 hours, then DMF filtered off from the resin. The resin is then washed with DMF for a total of two times. The Fmoc-protected resin is then de-protected using 20% PIP/NMP treatments. Sampling to verify Fmoc removal is performed after the last PIP/NMP treatment to confirm >99% Fmoc removal via UV analysis (IPC target <1% Fmoc remaining). After the final 20% w/w PIP/NMP treatment, the resin bed is washed multiple times with DMF. The peptide backbone is then built out using the following general conditions for each amino acid coupling and deprotection:

| Process step | Solvent/Reagent | Volume | Equivalence |
|---|---|---|---|
| Fmoc de-protection | 20% (v/v) piperidine/NMP | 9 ml/g resin | |
| Post de-protection washes | DMF | 9 ml/g resin | |
| Coupling reaction solution | NMP | 7.25 ml/g resin | |
| | Amino Acid | | 3.0 equiv |
| | Oxyma Pure | | 3.0 equiv |
| | DIC | | 3.3 equiv |
| Post coupling washes | DMF | 9 ml/g resin | |
| ivDde removal | 8% hydrazine/DMF | 9 ml/g resin | |
| Post ivDde removal washes | DMF | 9 ml/g resin | |
| Post build de-swelling washes | IPA | 1.8 mL/g resin | |

Fmoc Deprotection: Resin in the peptide reactor is treated with either three or four charges of the 20% v/v PIP/NMP solution. Each treatment is stirred on the resin for 30 min followed by filtration to complete Fmoc protecting group removal. After the final 20% v/v PIP/NMP treatment, the resin bed is washed a minimum of six times with DMF at the pre-specified DMF volume charge.

Amino Acid Activation: A pre-prepared solution of 12% w/w Oxyma Pure/NMP is charged to a reactor. The selected Fmoc amino acid is then added. The mixture is stirred at 20±5° C. until the Fmoc amino acid has completely dissolved. The Fmoc-AA/Oxyma Pure/NMP solutions are then cooled to 15±3° C. prior to activation to ensure the minor exothermic activation reaction is controlled and the resulting solution temperature is maintained in the range specified of 20±5° C. The amino acid solution is then activated by DIC addition. The activated ester solution is then stirred for 20-30 min. prior to transfer of the solution to the reactor containing the peptide on resin intermediate.

Coupling: Upon completion of the pre-activation step, the activated ester solution is transferred to the reactor containing deprotected peptide on resin to initiate the coupling reaction. The peptide coupling reaction is stirred at 20±5° C. for at least 4 hours. After the required stir time, the resin slurry is sampled for coupling completion (IPC). Sampling is repeated at specific intervals as needed until a passing IPC result is obtained. Re-coupling operations are performed, if necessary. When the coupling is complete, the peptide reactor solution contents are filtered then the peptide on resin intermediate s are washed several times with DMF to prepare for the next coupling.

Ile (12) to Aib (13) Coupling: The Fmoc-Ile (12) to Aib (13) coupling is performed using a symmetric anhydride approach utilizing six equivalents of the Fmoc-AA, three equivalents DIC. Activation time is extended to 40-60 min for this sequence to ensure formation of the activated symmetric anhydride species. An extended coupling stir time (18 h) is required to achieve reaction completion (<1% uncoupled) as determined by HPLC analysis.

Lys (20) ivDe De-protection (Preparation 23): A selective de-protection of the Lys (20) ivDde group of the 39 amino acid full protected on resin Boc-Tyr (1)-Ser (39) peptide backbone is performed. De-protection is achieved using 8% w/w hydrazine hydrate in DMF solution with stirring for 4 h at ambient temperature. The de-protection reaction is monitored by HPLC targeting an IPC limit of <1% of the Lys (ivDde) component remaining after de-protection. The resulting peptide fragment (Preparation 23), is repetitively washed (8×) with DMF to completely remove residual hydrazine. The fully built Preparation 23 fragment is washed four times with IPA then dried at ≤40° C. until LOD of ≤1% is achieved). Preparation 23 is packaged and stored cold (−20° C.) prior to coupling with Preparation 6.

Coupling of Preparation 6 to Preparation 23: Preparation 6 (1.5 equiv) and PyBOP (1.5 equiv) solids are charged to a reactor followed by DMF and the mixture is stirred until dissolution occurs. Collidine is then charged to initiate formation of the active ester species. The activated ester solution is stirred for 60 min prior to transfer to the reactor containing the Preparation 23 intermediate. The reaction slurry is stirred for 18 h at 25° C. The slurry is sampled for coupling completion (IPC) and sampling is repeated, if necessary, at specific intervals as needed to achieve passing IPC (<1% preparation 23) results. When the coupling is complete, the solution contents are filtered to waste. The fully built preparation 24 intermediate is washed multiple times with DMF, then IPA. Preparation 24 is dried at ≤40° C. until LOD≤1% is achieved. Preparation 24 is packaged and stored cold (−20° C.) prior to cleavage from resin.

Resin Cleavage and Example 4A Crude Isolation: A cleavage cocktail is prepared consisting of trifluoroacetic acid (TFA), triisopropylsilane (TIPS), dithiotheritol (DTT), DCM and water. The cleavage cocktail is cooled to 15±5° C. Reagent charges are shown in the following Table:

| Process step | Solvent/ Reagent | Volume (per Resin Bound charged) |
|---|---|---|
| Cleavage cocktail | TFA | 7.16 mL/g |
| | water | 0.34 mL/g |
| | TIPS | 0.24 mL/g |
| | DTT | 0.24 g/g |
| | DCM | 0.75 mL/g |
| Net cocktail charge | n/a | ~8.50 mL/g |
| Spent resin wash | DCM | 3 mL/g |
| Anti-solvent | MTBE | 14 g/g |
| Vessel and cake washes | MTBE | 3 g/g |

Preparation 24 is charged to a reactor followed by the cleavage cocktail. The mixture is stirred and maintained at 23° C. for 3 h. The mixture is filtered then the spent resin is washed with DCM. The DCM wash filtrate is combined with the bulk de-protection solution and the contents cooled to ≤−10° C. MTBE is cooled to ≤−13° C. then cold MTBE is fed to the cold filtrate in two portions. The MTBE feed rate is controlled to maintain the crude solution internal temperature at ≤5° C. The initial MTBE charge constituted ~45% of the total MTBE charge. A soft precipitate forms near the end of the MTBE addition but readily re-dissolved into solution. The precipitation solution is then re-cooled to an internal temperature of −15±5° C. The second MTBE addition is fed at a rate approximately 5-10 times the initial MTBE feed rate and constituted ~55% of the total MTBE charge. The precipitation slurry internal temperature is maintained at ≤0° C. during the addition. The resulting slurry is aged at −8±3° C. for a minimum of 6 h followed then warmed to 0±3° C. and aging for an additional 2 h prior to isolation.

The cold crude peptide slurry is filtered then the resulting wet cake washed with MTBE. The Example 4A Crude wet cake is then dried to an IPC target LOD value of <1%. Example 4A Crude product is packaged and stored. The Crude intermediate is stored cold (−20° C.) until purification. Overall, 45.39 kg crude Example 4A is produced with 45 wt % and 64% HPLC area percent purity. Contained yield based on Sieber resin=47%.

EXAMPLE 4A PURIFICATION

Mobile Phases:
Mobile Phase A (MPA)
90% Water, 0.1% TFA, and 10% ACN
Mobile Phase B (MPB)
10% Water, 0.1% TFA, and 90% ACN Reverse Phase Purification 1 (RP1): The Example 4A Crude is dissolved in 90 wt % MPA and 10 wt % MPB. The solution is stirred at least 7 h to complete tryptophan decarboxylation. The aged crude solution is filtered and loaded onto pre-equilibrated Kromasil 100-10-C8 packed column. The column is washed with a mixture of A (90% water, 0.1% TFA, and 10% ACN) and B (10% water, 0.1% TFA, and 90% ACN) buffers resulting in 30% ACN for two column volumes and prepared for elution by increasing the mixed concentration of ACN from 30% to 35% over one column volume. Tirezepatide is eluted from the column using a 1.5% ACN increase per column volume until elution is complete. The Eluent is fractionated and assayed for purity using RP-HPLC. The column is regenerated by increasing the ACN from 47% to 65% over one column volume and by continuing to flow 65% ACN for three column volumes. The column is re-equilibrated using 30% ACN for two column volumes prior to the next injection sequence.

Fractions that qualify for mainstream inclusion are pooled. Fractions that do not meet the purity criteria but have greater than 50% purity may be combined for recycle injections after all of the primary injections are complete. Recycle fractions are separated into frontside fractions and backside fractions, diluted with Buffer A and stored cold. Recycle injections are processed and pooled using the primary injection criteria; however, only main peak fractions are forward processed and no further recycling is performed. Upon completion of mainstream pooling, the intermediate is assayed for concentration and purity. The material is diluted and pH adjusted to pH8 prior to RP2 processing. The RP1 process yields 37 kg crude product, and 14277 g contained product with an average pool purity of 90.9%.

Reversed Phase Purification 2: The Example 4A RP1 Solution is loaded onto a pre-equilibrated Kromasil 100-10-C8 packed column The column is washed with a mixture of Buffer C (90% aqueous $NH_4OAc$ pH 8.0, 10% ACN) and Buffer D (10% aqueous $NH_4OAc$ pH 8.0, 90% ACN) that results in a 20% ACN solution for two column volumes. Tirzepatide is eluted from the column using a 3.5% ACN increase per column until elution is complete. The eluent is fractionated and assayed for purity using RP-HPLC. Following elution, the column is regenerated by increasing the ACN to 80% over one column volume and continuing to flow 80% ACN for three column volumes. The column is re-equilibrated using 20% ACN for two column volumes prior to the next injection sequence.

Fractions that qualify for mainstream inclusion are pooled. Fractions that do not meet the purity criteria but have greater than 60% purity may be combined for recycle injections after all of the primary injections are complete. Recycle fractions are separated into frontside pools and backside pools, diluted with Buffer C and stored cold. Recycle injections are processed and pooled using the primary injection criteria; however, only main peak fractions will be forward processed and no further recycling will be performed. Upon completion of mainstream pooling, the intermediate is assayed for concentration and purity. The material may be pH adjusted to 8.0 in preparation for the TFF step. The RP2 process, starting with 14.2 kg yields 10.9 kg contained product at a yield of 76.7%.

Ion Exchange Chromatography (IEX): The Example 4A RP2 solution is filtered and loaded to an Amberchrom CG-300M column. Two fractions are eluted using Mobile Phase E (10% aqueous ammonium acetate, 5% IPA, pH8) and Mobile Phase F (isopropanol). Fractions are analyzed for peptide content and those <3 mg/mL are discarded. The concentrate pooled fractions are stored at 20° C. prior to precipitation. The IEX process starts with 10.9 kg of RP2 to yield 14.3 kg contained Example 4A material with purity of 97.8% pool purity.

Precipitation: Example 4A IEX solution (333 kg) is filtered and then isopropanol (850 L) is charged to reduce the water content to <10% w/w water. The diluted solution is cooled to 0±3° C. in preparation for MTBE charging and precipitation. MTBE (2304 L, 1708 kg) is cooled to 0±3° C. The cold MTBE is fed to the IEX solution at a ~0.69 kg/min rate through the first ~37% of the MTBE charge. The feed rate is then increased to an average of ~2.3 kg/min to complete the remaining ~63% of the MTBE charge. Temperature during feed is maintained at <5° C. The resulting precipitation slurry is filtered cold (≤−10° C.). then the filter cake washed with MTBE. The filter cake is dried to an LOD <2%.

Humidification 4A: Example 4A is humidified by passing wet nitrogen through into the filter drier. The humidity of the exiting gas stream from the outlet of the filter is monitored every 60 min. Humidification is continued until <0.5% MTBE and <0.2% IPA remain in the wetcake. After completion of the humidification process, nitrogen flow is switched to flow dry nitrogen through the Example 4A Pure product cake. The material is sampled for water and residual solvents against specific IPC targets and drying using dry nitrogen is continued until the desired target water content of 5-7% w/w is met. A total of 12.9 kg Example 4A isolated with >95% purity in peptide content. Overall yield based on Sieber resin loading=31%.

EXAMPLE 4B (LINEAR SPPS)

Tirzepatide (SEQ ID NO:1)

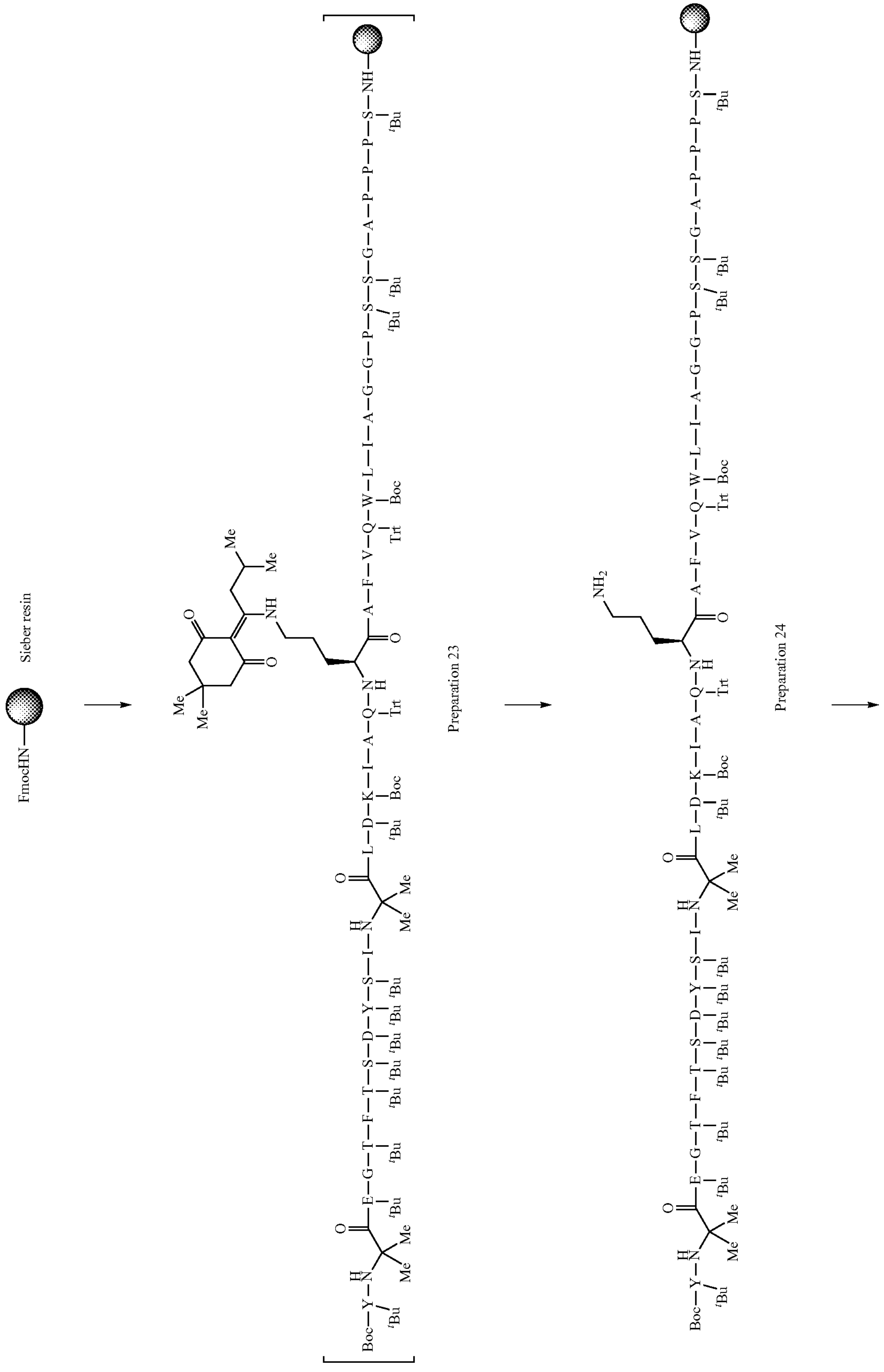
Sieber resin
Preparation 23
Preparation 24

-continued
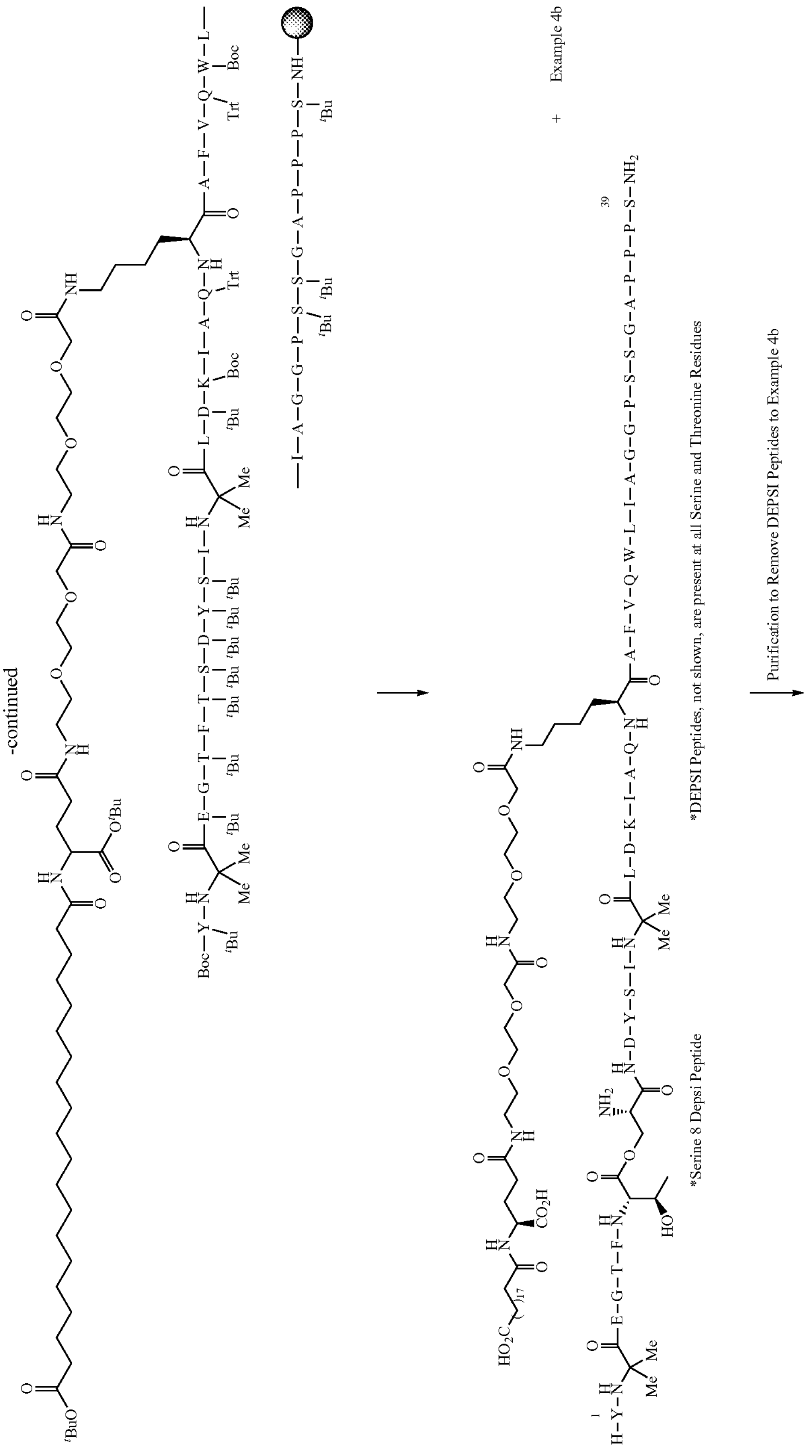

-continued
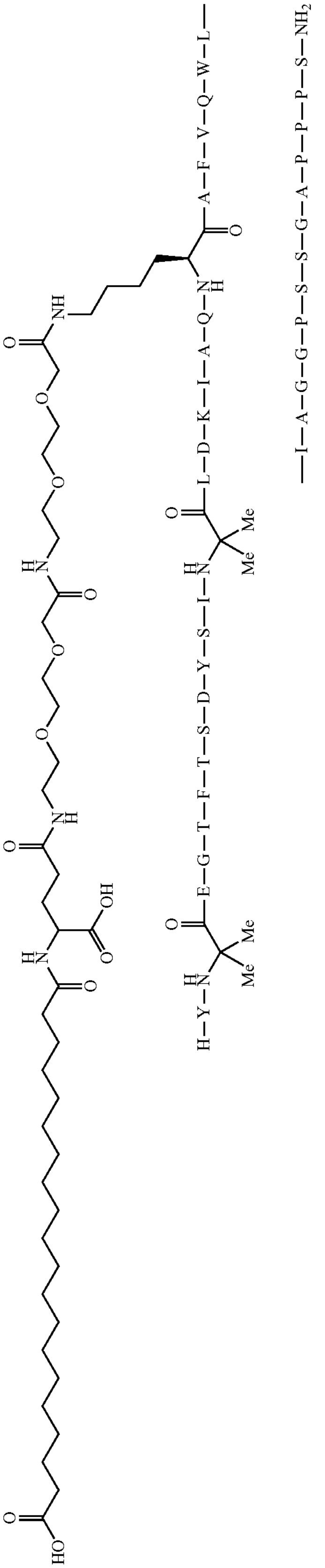
Example 4B

Preparation 23

The process to produce Preparation 23 is substantially as set forth by Example 4A except NMP is globally replaced with DMF for all couplings and deprotections. In addition, the stoichiometry of amino acid: Oxyma to DIC is reduced to 2.5:2.5:2.7 molar equivalents based on Siber resin. The single exception related to DMF usage is the Ile 12 to Aib 13 coupling where NMP is retained. In this exemplification 17.6 kg Sieber Resin in processes to 92.2 kg preparation 23 peptide on resin intermediate.

Preparation 24

The process substantially as set forth by Example 4A prepares 92.1 kg Preparation 23; further processed to 97.3 kg preparation 24 peptide on resin intermediate. Preparation 24 is packaged and stored cold (−20° C.) prior to cleavage from resin.

Resin Cleavage and Example 4B Crude Isolation: Two batches are run on 32 kg scale Preparation 24 using the conditions substantially as described in Example 4A to deliver 24.4 kg Example 4B, 69.5% HPLC Purity and 52.6% yield and 21.3 kg Example 4B, 88.3% HPLC Purity and 45.2% yield. The crude intermediate is stored cold (−20° C.) until purification.

Example 4B Purification: Crude Dissolution: Tirzepatide Example 4B Crude is charged to a dissolution vessel and dissolved in a 1:1 acetonitrile: water solution to a final concentration of 25 g solid/L of solution. The resulting solution is pH adjusted to 8.5-9.5 with ammonium hydroxide to initiate the conversion of Depsi peptide isomers (10-15%) to Tirzepatide Example 4B. The pH adjusted mixture is stirred for at least one hour to allow the Depsi conversion to occur. The pH is then adjusted to 1.5-2.5 by addition of trifluoroacetic acid and diluted to 30% acetonitrile content in preparation for chromatography. In total, the crude solution is stirred at least 7 hours to convert Trp $CO_2$ salt to Tirzepatide Example 4B.

Conversion of Tirzepatide (TZP) to Depsipeptide:

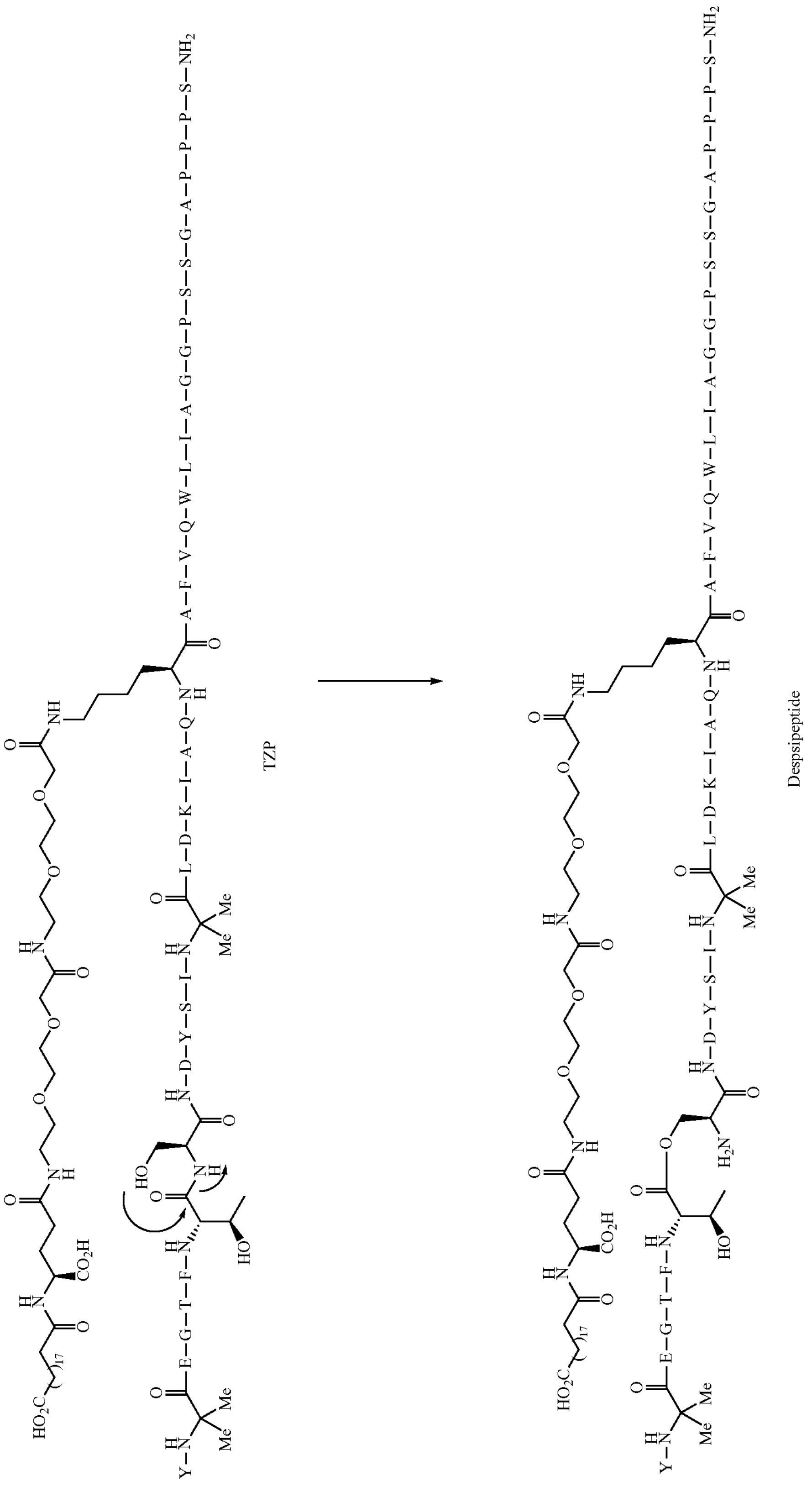
TZP
Despsipeptide

Depsi Peptide Conversion to API:

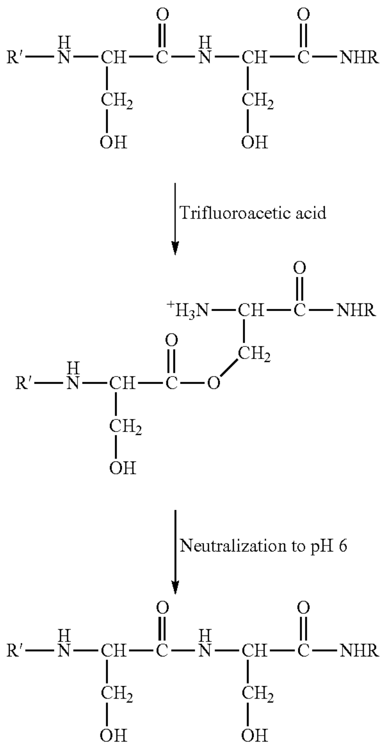

Reverse Phase Purification 1 (RP1): The RP1 process substantially as presented by Example 4A, may be used to convert Depsi peptide to API. The RP1 purification process is substantially the same as what is described in Example 4A; however, the Crude Dissolution step described above enhances the capability of the RP1 chromatographic step. This enables a higher g Tirzepatide per L resin load and decreases the number of injections required to purify crude Tirzepatide under the conditions described in Example 4. In this exemplification 23.7 kg content corrected crude Example 4B generates 25.4 kg of Example 4B (107%) after RP1. Total solution volume=2910 L@8.72 g/L and once all of the pool fractions are collected, the mixture is stirred, sampled and held prior Reverse Phase Purification 2 (RP2).

Reverse Phase Purification 2 (RP2): Substantially the same purification process as described in Example 4A, and using methods known to the skilled artisan, is used for Reverse Phase Purification 2 (RP2). In this exemplification 15.2 kg contained Example 4B from RP1 is purified after RP2 to 13.8 kg Example 4B in ~98% purity. Total solution volume=808 L@17.0 g/L. The mixture is stored prior to Tangential Flow Filtration.

Tangential Flow Filtration (TFF): TFF membranes are installed and flushed with water. Ammonium acetate buffer is prepared using Low Endotoxin Purified Water, acetic acid and ammonium hydroxide. Isopropanol is then charged to deliver a 5:95 100 mM $NH_4OAc$ pH 8.0: IPA buffer. The 17 g/L RP2 solution of Example 4B is concentrated through the TFF to ~125 g/L. The RP2 solution is recirculated allowing the solvent to permeate through the membrane while retaining the peptide solution on the retentate side of the membrane, in solution. Following concentration, the diafiltration buffer is fed to the retentate holding tank while permeate is continuously collected. The exchange of buffer is continued until the desired solvent composition and peptide concentration are met. The solution is emptied from the system, and the resulting polarization layer is rinsed from the membrane and pooled with the peptide concentrate. Two sections of RP2 solution (403.9 L@17 g/L, 9.87 kg API) were processed through TFF.

Co-Feed Precipitation: The TFF sections are combined (138.2 kg, 78.3 g/L) and KF measured (8.9%) to verify <10% water. MTBE (243 kg) is charged to a separate vessel and cooled to 0° C. IPA (48 kg), water (6 kg) and MTBE (100 kg) are added to the precipitation vessel and the solution cooled to 0° C. The TFF and MTBE process streams are co-fed to the precipitation vessel at rates of 1.6-1.8 and 2.9-3.1 kg/min, respectively. The resulting slurry is aged for an additional 0.7 hr at 0° C. then warmed to 15° C. The slurry is aged at 15° C. for 1 hr followed by the addition of MTBE (118 kg). The slurry is aged at 15° C. for 1 hr and then cooled to 2.5° C. The slurry is filtered cold and the filter cake washed with MTBE (573 kg). The filter cake is dried to LOD <2%.

Humidification: Humidification substantially as set forth by Example 4A, and using methods known to the skilled artisan, is applied to Example 4B material. A total of 14.5 kg Example 4B (SEQ ID NO:1) is isolated with >97.7% HPLC purity and 88.4% peptide content. Overall yield based on Sieber resin loading=46%.

EXAMPLE 5

Continuous Synthesis of Preparation 31 Using Convergent Chemistry in Flow

Synthesis of Preparation 31 from peptide fragments is carried out using both batch approaches to the chemistry as well as sequential addition of fragments in a tubular flow reactor. The generalized approach to the synthesis involves coupling of the two fragments by blending two solutions, along with coupling agent into a tube reactor, which is then followed with a base addition, and additional residence time in a tube reactor to perform the removal of the FMOC protecting group. This prepares the coupled species for the addition of the next fragment. Excess reagents, base, and solvent are removed between consecutive coupling reactions using a nanofilter with a membrane that is sized to retain the peptide and permeate lower molecular weight impurities. Diafiltration is used to fully remove lower molecular weight impurities prior to the subsequent coupling steps. A description and analytical results from the exemplification of these transformations are included below.

HPLC is used to confirm the synthesis of Preparation 31 from Preparation 29 and Preparation 30. The method of analysis uses a C4 stationary phase column at 65° C. (2.1 mm i.d.×150 mm×1.7-micron particle size) with a 60-98% B gradient of 0.1% TFA in water and acetonitrile over 12 minutes. UV detection at 214 nm is used for this material. Table A.5 shows high resolution mass spectrometry data collected for the product of the Step 3 coupling reaction (Preparation 31) made in flow. Mass accuracy confirms the desired species.

TABLE A.5

Confirmation of measured Preparation 31 via mass accuracy calculated using high resolution mass spectrometry data.

| Compound | Chemical Formula | Theoretical Monoisotropic Mass (neutral) | Observed Ion m/z | Charge State | Calculated Monoisotropic Mass (neutral) | Mass Accuracy (ppm) |
|---|---|---|---|---|---|---|
| Preparation 31 | $C_{334}H_{512}N_{48}O_{74}$ | 6379.7777 | 1595.9512 | 4 | 6379.775694 | 0.3 |

Native chemical ligation is a process useful for preparing full length peptides comprising a cysteine or an alanine in the sequence. The process employs a chemoselective reaction of two unprotected peptide segments to produce a transient thioester-linked intermediate. The thioester-linked intermediate rearranges to provide a full length ligation product having a native peptide bond at the ligation site. The artisan will appreciate that the technique of native chemical ligation can be useful in the chemical synthesis of full length peptides containing cysteine or alanine.

EXAMPLE 6

Native Chemical Ligation Process

Tirzepatide (SEQ ID NO:1)

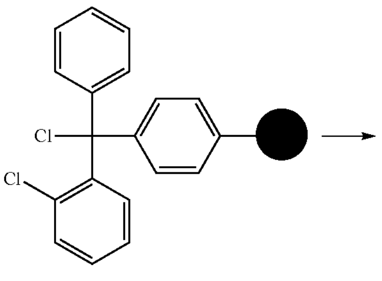

2-Chlorotrityl chloride (2-CTC) resin

-continued

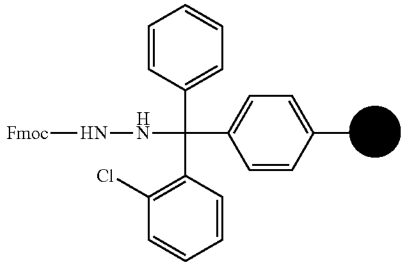

Preparation 32

Synthesis of Fmoc-Hydrazine-CTC Resin (Preparation 32)

2-CTC resin (10.7 g, 17.7 mmol) is swollen in 100 mL DCM for 20 min at 0° C. 9-fluorenylmethyl carbazate (15.6 g, 61.4 mmol, 3.5 equiv) is dissolved in 210 mL of 2:1 DMF:DCM. DIEA (31 mL, 178 mmol, 10.1 equiv) is added to the 9-fluorenylmethyl carbazate solution. This solution is then slowly added to the resin at 0° C. It is stirred at 0° C. for about an hour and allowed to warm up to the room temperature. The reaction mixture is stirred over 16 hours at the room temperature. Methanol (10 mL) is then added to quench the remaining 2-CTC resin and stirred for 15 min. The resin is rinsed with 200 mL DMF, followed by DMF (2×100 mL), water (3×100 mL), DMF (3×100 mL), methanol (3×100 mL), and finally with DCM (3×100 mL). The resin is dried in a vacuum oven at 27° C. for 16 hours. The resin loading is measured to be 0.74 mmol/g by quantitative NMR.

Preparation 33

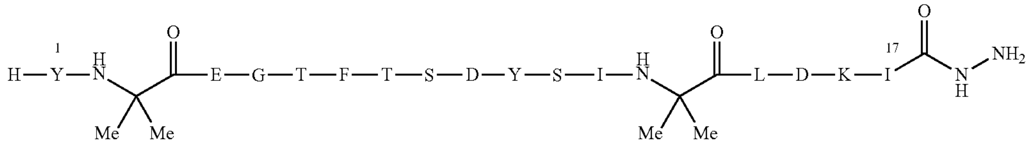

Synthesis of Peptide Hydrazide (17-Mer) (Preparation 33

SEQ ID NO: 32

Hydrazine-CTC resin (1.01 g, loading value: 0.65 mmol/g) is taken in a 40 mL reactor vessel and swollen with 3×4 mL DCM (30 s each) followed by 2×10 mL DMF (20 min each) on a peptide synthesizer. Fmoc-Ile-OH (0.919 g, 2.60 mmol, 4 equiv) and HBTU (0.99 g, 2.61 mmol, 4 equiv) are dissolved in 7 mL of DMF. DIPEA (0.91 mL, 5.22 mmol, 8 equiv) is added to the amino acid solution and the volume is made up to 10 mL with DMF. The activated amino acid solution is added to the resin. The slurry is allowed to mix with nitrogen for 8 hours. After 8 hours, the resin is washed with 5×10 mL DMF, 5×10 mL DCM and dried for 12 hours. The loading of the resulting resin is measured to be 0.54 mmol/g by quantitative NMR. 0.91 g of this resin is used for the Preparation 33 (SEQ ID NO:32) synthesis.

Deprotection: 4×9 mL of 20% v/v piperidine in DMF, 30 minutes each. Couplings: 3 equivalents of amino acid, 3 equivalents of OXYMA and 3.3 equivalents of DIC are used for amino acid coupling. The resin is washed with 5×9 mL DMF with 1 min $N_2$ mix after each coupling and the final iteration of deprotection. At the end of the peptide hydrazide synthesis, the resin is washed with DCM with $N_2$ mixing. The resin is dried on the synthesizer.

Deprotection and Cleavage: 25 mL of the cleavage cocktail made with 5% w/v dithiothreitol (DTT), 2.5% v/v water, 2.5% v/v triisopropylsilane (TIPS) and 90% trifluoroacetic acid (TFA) is added to the dried resin (2.37 g) and mixed for 3 hours on a rotary mixer. The resin is filtered and washed with 2×2.5 mL TFA. The filtrate is poured into 175 mL cold MTBE and the peptide precipitated out immediately. The filtration flask is washed with 2×2.0 mL TFA and poured into the cold MTBE. It is cooled down to −20° C. for half an hour and then centrifuged. The peptide precipitate is then washed twice with 150 mL MTBE and centrifuged. The peptide precipitate is dried in a vacuum oven at 27° C. for 16 hours. A 1.25 g sample of the crude Preparation 33 is obtained after drying [Expected (mass+$2H^+$)/2=968.4883, observed (mass+$2H^+$)/2=968.4879].

ethoxy]acetyl]amino]ethoxy]ethoxy]acetic acid (1094.4 mg, 1.252 mmol, 2 equiv) is dissolved in 10 mL of anhydrous DMF. TNTU (506.9 mg, 1.360 mmol, 2.2 equiv) and DIEA (0.24 mL, 1.4 mmol, 2.2 equiv) are added to it. The volume is made up to 15 mL with anhydrous DMF. It is allowed to mix for 30 min on a rotary mixer. The activated ester of Preparation 6 is then added to the resin and allowed to mix for 12 hours with nitrogen stream. After 12 hours, the solution is drained and the resin is washed with 5×10 mL DMF and 7×10 mL DCM with 1 min $N_2$ mix. The resin is dried for 8 hours on the synthesizer.

Deprotection and Cleavage: 20 mL of the cleavage cocktail made with 5% w/v dithiothreitol (DTT), 2.5% v/v water, 2.5% v/v triisopropylsilane (TIPS) and 90% trifluoroacetic acid (TFA) is added to the dried resin (2.42 g) and mixed for 3 hours on a rotary mixer. The resin is filtered and washed with 2×2.0 mL TFA. The filtrate is poured into 200 mL cold MTBE and peptide precipitated out immediately. The filtration flask is washed with 2×2 mL TFA and is poured into the cold MTBE. It is cooled down to −20° C. for 30 min and then centrifuged. The peptide precipitate is washed twice with 240 mL MTBE and centrifuged. The peptide precipitate is dried in a vacuum oven at 27° C. for 14 hours. 1.853 g of the crude Preparation 34 is obtained after drying. It is purified by RP-HPLC on a Kromasil 100-10-C8 10 μm column (30 mm×250 mm) at ambient temperature with a linear gradient of 30-55% acetonitrile in water over 25 min after 15% acetonitrile in water for the first 5 min and a constant 0.1% TFA over 30 min. 1.28 g of the purified Preparation 34 (SEQ ID NO:33) is obtained [Expected (mass+2H)/2=1470.7929, observed (mass+2H)/2=1470.7885].

Thioester synthesis (conversion of Preparation 33 to Preparation 35

Crude peptide hydrazide (Preparation 33, 2.422 g, 1.251 mmol) is dissolved in 50 mL of the ligation buffer (6M Preparation 34

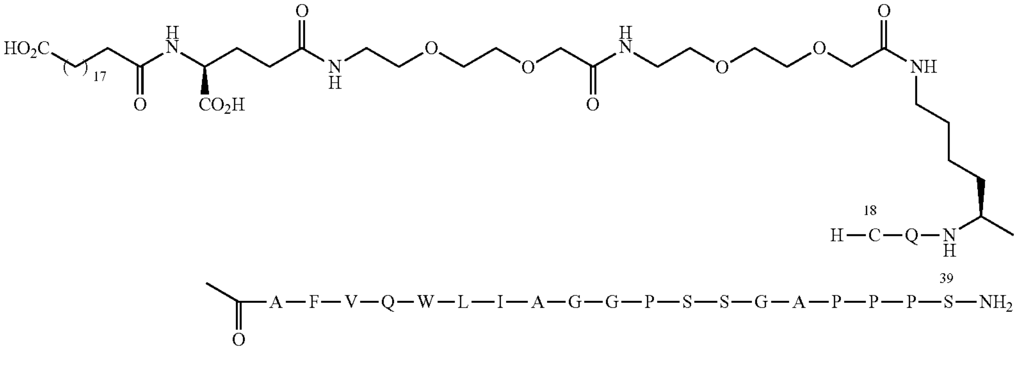

About 0.62 mmol of Preparation 34 is synthesized on Sieber amide resin by standard SPPS protocols. Fmoc-Lys (ivDde)-OH is used for orthogonal deprotection and lysine acylation.

Deprotection of ivDde: Hydrazine monohydrate (64% w/w) (1.98 g, 25.3 mmol) is diluted to 24.4 g with DMF and 20 g is added to the resin. The slurry is allowed to stir with nitrogen stream. Washed with 5×9 mL DMF after about two hours. It is repeated once more.

2-[2-[[2-[2-[2-[2-[[(4S)-5-tert-butoxy-4-[(20-tert-butoxy-20-oxo-icosanoyl)amino]-5-oxo-pentanoyl]amino]ethoxy]

guanidine hydrochloride and 0.2M sodium hydrogen phosphate monobasic, pH 3.35) and cooled to −15° C. in an acetone-ice bath. 9.4 mL of 1M sodium nitrite solution (9.4 mmol, 7.5 equiv.) is added to the peptide hydrazide solution and allowed to stir for 20 min at −15° C. Meanwhile, 1 mL of 2,2,2-trifluoroethanethiol (TFET) is made up to 10 mL with ligation buffer (6M guanidine hydrochloride and 0.2M sodium hydrogen phosphate monobasic, pH 7.0). After 20 min, 10 mL of the TFET mixture is added to the peptide hydrazide solution to cause in-situ thiolysis of the peptidyl azide generated from Preparation 33.

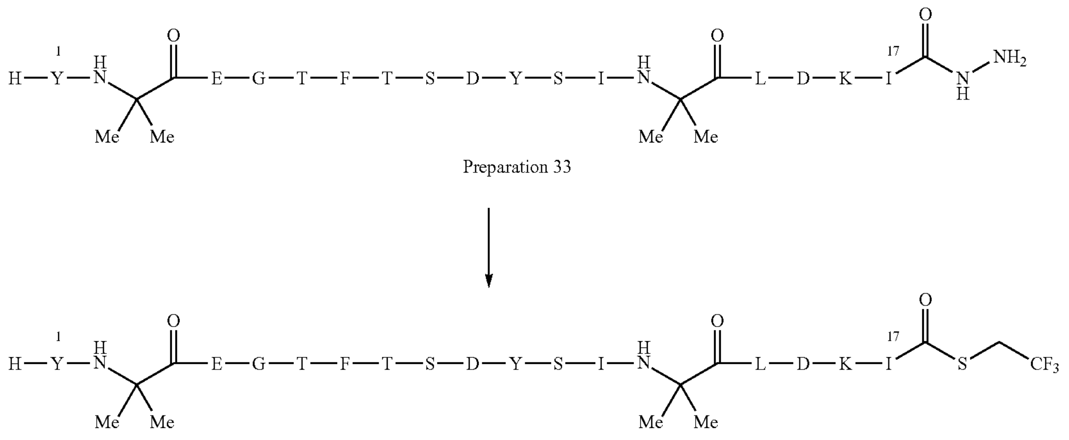

Preparation 33

Preparation 35

The pH of the reaction mixture is adjusted to about 6.95 with 5N sodium hydroxide solution. Thiolysis of the peptidyl azide is allowed to run for 45 min and the volume is made up to 100 mL with the ligation buffer (pH 7.0). The crude thioester mixture is purified by RP-HPLC on a Waters X-Bridge C18 10 μm column (10 mm×250 mm) at ambient temperature with a linear gradient of 25-42% acetonitrile in water over 25 min after 10% acetonitrile in water for the first 2.8 min and a constant 0.1% TFA for the 28 min of purification. This yields 1.03 g of the TFET thioester (Preparation 35 (SEQ ID NO: 34)) [Expected (mass+2H$^+$)/2=1010.4650, observed (mass+2H$^+$)/2=1010.4620].

Native Chemical Ligation: Aqueous solution of 6M guanidine hydrochloride and 0.3 M sodium hydrogen phosphate monobasic (pH 7.0) is the ligation buffer used in native chemical ligation. All solutions are made in this ligation buffer. Dissolved 350.4 mg (0.174 mmol) of the peptide thioester Preparation 35 (SEQ ID NO:34) in 50 mL of the ligation buffer. An 8.0 mL portion of 0.5M 4-mercaptophenylacetic acid (MPAA) solution is added to the peptide thioester solution. N-terminal cysteine containing peptide (Preparation 34 (SEQ ID NO:33), 524.6 mg, 0.178 mmol, 1.03 equiv) is dissolved in 48 mL of the ligation buffer in a 50 mL centrifuge tube. The solution of Preparation 34 is added to the thioester solution. The tube is rinsed with 2×8 mL of the ligation buffer (about pH 7.0) and added to the reaction mixture. The pH of the reaction mixture is adjusted to about 7 with 5N NaOH solution. An 8.0 mL portion of tris(2-carboxyethyl) phosphine (TCEP, 0.5 M, pH 7.0) is added to the reaction mixture and the pH is adjusted again to 7.0 with 0.2 mL of 5N sodium hydroxide solution. The reaction is allowed to stir at room temperature for 24 hours and then stored in a freezer. Additional 3 mL of 0.5M TCEP solution is added before purification. Preparation 36 (SEQ ID NO:35) is purified by RP-HPLC on a Kromasil C18 10 μm column (10 mm×250 mm) at ambient temperature with a linear gradient of 20-50% acetonitrile in water (0.1% acetic acid and titrated to pH 9.0) over 23 min after 10% acetonitrile in water for the first 4 min during the 28 min of purification. About 372 mg (44.3%) of the tirzepatide cysteine analogue Preparation 36 is obtained after purification [Expected (mass+3H$^+$)/3=1615.17263, observed (mass+3H$^+$)/3=1615.1686].

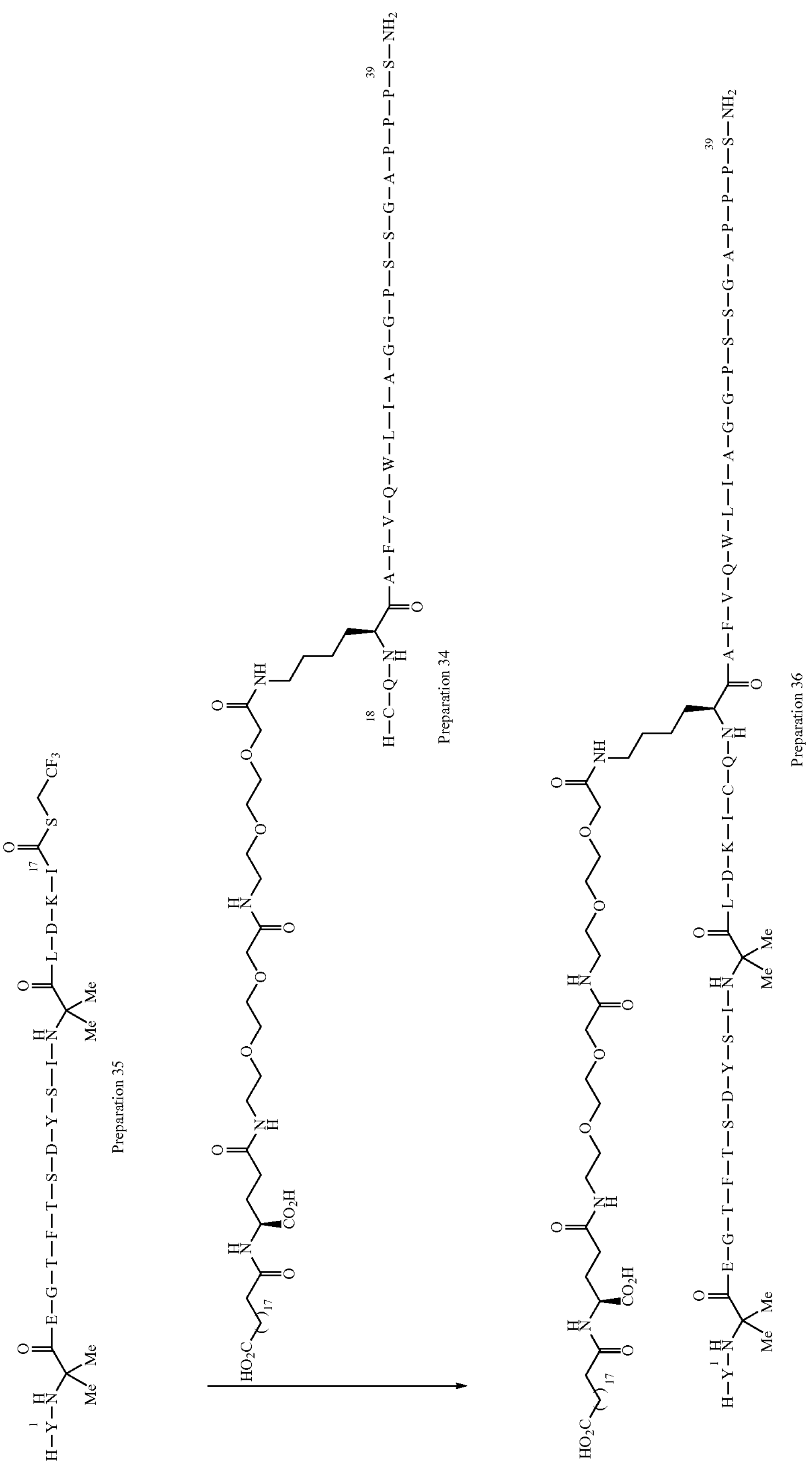
Preparation 35
Preparation 34
Preparation 36

Desulfurization: Aqueous solution of 6 guanidine hydrochloride and 0.3M sodium hydrogen phosphate monobasic (pH 7.0) is the buffer used in desulfurization. All solutions were made in this buffer. 2,2'-Azobis[2-(2-imidazolin-2-yl) propane]dihydrochloride (Preparation 37, 808.2 mg, 2.5 mmol) is dissolved in 10 mL of the buffer and the pH is adjusted to about 7.0 with 5N NaOH. The volume is made up to 15 mL with the buffer. Tirzepatide cysteine analogue Preparation 36 (105.2 mg, 0.022 mmol) is dissolved in 30 mL of the buffer and 6 mL of the Preparation 37 solution is added to it. Five mL of 0.3M L-glutathione reduced solution (L-GSH, pH 7.0) and 7.5 mL of 0.5 M TCEP solution (pH 7.0) are added to it. The solution is heated at 44° C. for 4.5 hours, whereby the reaction is found to be complete by UPLC analysis [Expected (mass+3$H^+$)/3=1604.5153, observed (mass+3$H^+$)/3=1604.5122]. The desulfurization yield is calculated by UPLC using a tirzepatide (SEQ ID NO:1) reference standard. The yield is estimated to be 47%.

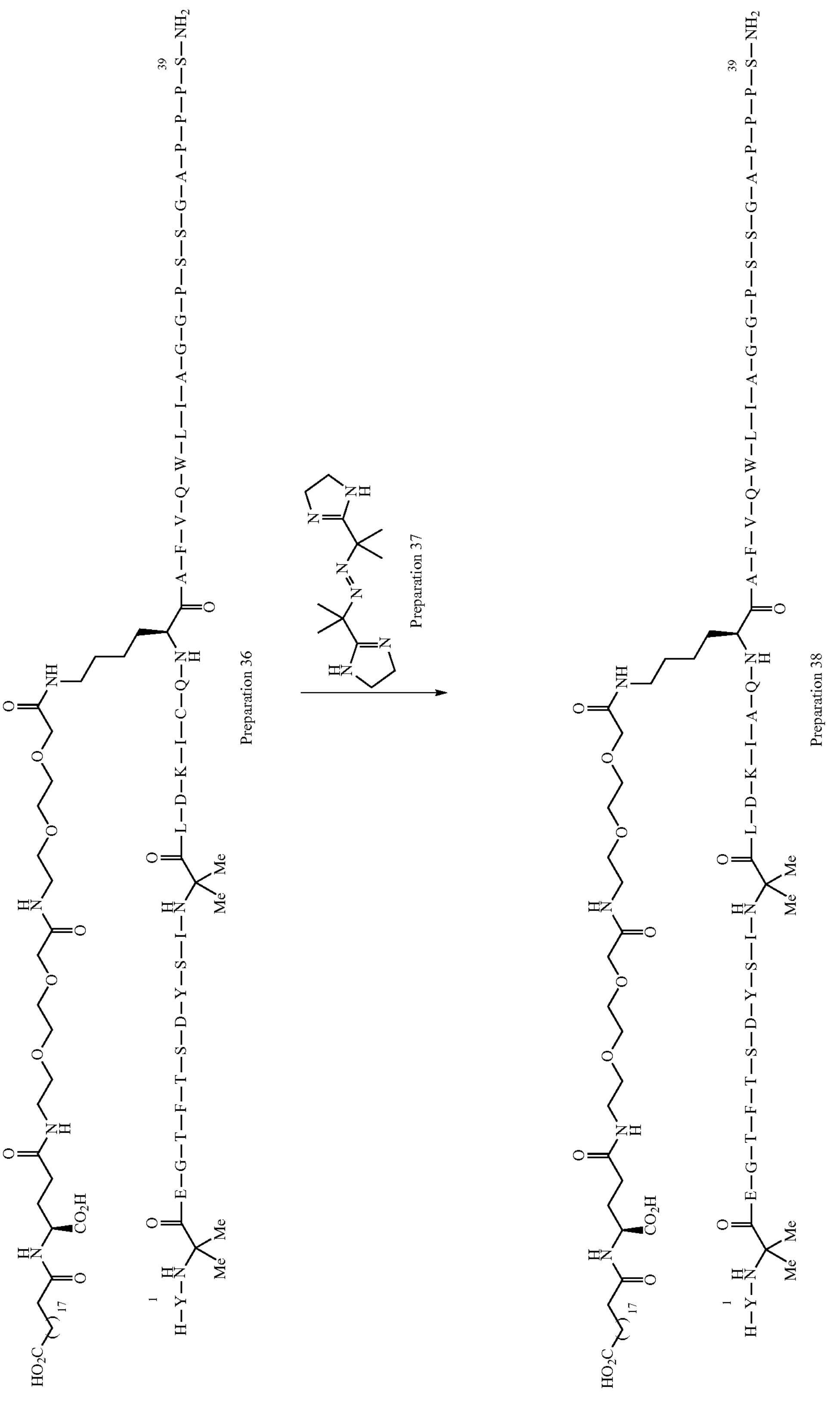
Preparation 36
Preparation 38

Native Chemical Ligation (Approach 2): Synthesis of Peptide Hydrazide Preparation 39

SEQ ID NO:36

Hydrazine-CTC resin (2.03 g, 1.32 mmol, loading value: 0.65 mmol/g) is taken in a 40 mL reactor vessel and swollen with 3×10 mL DCM (30 s each) followed by 2×10 mL DMF (20 min each) on a Symphony synthesizer. HBTU (1.48 g, 3.90 mmol, 3.0 equiv) is dissolved in 13.1 mL of (25S,52S)-52-((((9H-fluoren-9-yl) methoxy) carbonyl)amino)-25-(tert-butoxycarbonyl)-2,2-dimethyl-4,23,28,37,46-pentaoxo-3,32,35,41,44-pentaoxa-24,29,38,47-tetraazatripentacontan-53-oic acid (Preparation 17, 365 mg/mL in DMF) solution (3.91 mmol, 3.0 equiv). DIPEA (1.4 mL, 8.04 mmol, 6.1 equiv) is added to the above solution and the volume is made up to 19 mL with DMF. The solution is allowed to mix at room temperature on a rotary mixer for 30 min. The activated ester solution of Preparation 17 is added to the resin. The slurry is allowed to mix with nitrogen for 8 hours. After 8 hours, the resin is washed with 5×10 mL DMF, 5×10 mL DCM and dried for 12 hours. The loading of the resulting resin is measured to be 0.26 mmol/g by quantitative NMR. 1.82 g of this resin is used for the peptide hydrazide Preparation 39 (SEQ ID NO:36) synthesis.

Deprotection: 4×9 mL of 20% v/v piperidine in DMF, 30 minutes each.

Couplings: 3 equivalents of amino acid, 3 equivalents of OXYMA and 3.3 equivalents of DIC are used for amino acid coupling.

The resin is washed with 5×9 mL DMF with 1 min $N_2$ mix after each coupling and the final iteration of deprotection. At the end of the peptide hydrazide synthesis, the resin is washed with 7×10 mL DCM with 1 min $N_2$ mixing. The resin is then dried for about 12 hours on the synthesizer.

Deprotection and Cleavage: 25 mL of the cleavage cocktail made with 5% w/v dithiothreitol (DTT), 2.5% v/v water, 2.5% v/v triisopropylsilane (TIPS) and 90% trifluoroacetic acid (TFA) is added to the dried resin and mixed on a rotary mixer. The resin is filtered, washed with TFA (2×2.5 mL), and the filtrate is poured into 175 mL of cold MTBE. The filtration flask is washed with TFA (2×2.5 mL) and washings are poured into the cold MTBE. It is cooled down to −20° C. for 30 min and then centrifuged. The peptide precipitate is then washed twice with 150 mL MTBE and centrifuged. The peptide precipitate is dried in a vacuum oven at 27° C. for 16 hours. 1.70 g of the crude peptide hydrazide Preparation 39 (SEQ ID NO:36) is obtained after drying. Crude peptide hydrazide, Preparation 39 is purified by RP-HPLC on Waters XSelectCSH C18 10 μm column (10 mm×250 mm) at ambient temperature with a linear gradient of 20-55% acetonitrile in water over 23 min after 10% acetonitrile in water for the first 3 min and a constant 0.1% TFA for the 28 min of purification. About 110 mg of the partially purified hydrazide Preparation 39 is obtained.

Deprotection and Cleavage: 25 mL of the cleavage cocktail made with 5% w/v dithiothreitol (DTT), 2.5% v/v water, 2.5% v/v triisopropylsilane (TIPS) and 90% trifluoroacetic acid (TFA) is added to the dried resin (2.92 g) and mixed on a rotary mixer. The resin is filtered and washed with 2×2.5 mL TFA. The filtrate is poured into 200 mL cold MTBE and the peptide precipitated out immediately. The filtration flask is then washed with 2×2 mL TFA and the washings are poured into the cold MTBE. It is cooled down to −20° C. for 30 min and then centrifuged. The peptide precipitate is then washed twice with 240 mL MTBE and centrifuged. The peptide precipitate is then dried in a vacuum oven at 27° C. for 16 hours. About 1.7 g of the crude 19-mer Preparation 40 (SEQ ID NO:37) is obtained.

Native Chemical Ligation: Aqueous solution of 6M guanidine hydrochloride and 0.3 M sodium hydrogen phosphate monobasic (pH 7.0) is the ligation buffer used in native chemical ligation. All solutions are made in this ligation buffer. Partially purified peptide hydrazide (Preparation 39, 56 mg, 0.019 mmol) is dissolved in 5 mL of the ligation buffer (6M guanidine hydrochloride and 0.3 M sodium hydrogen phosphate monobasic, pH 3.35) and cooled to −15° C. in an acetone-ice bath. 0.25 mL of 1M sodium nitrite solution (0.25 mmol, 13.2 equiv) is added to the peptide hydrazide solution and allowed to stir for 10 min at −15° C. After 10 min, 0.8 mL of 0.5M 4-mercaptophenylacetic acid (MPAA) solution is added to the peptide hydrazide solution to cause in-situ thiolysis of the peptidyl azide generated from Preparation 39. The pH of the reaction mixture is adjusted to about 7.0 with 5N sodium hydroxide solution. Thiolysis of the peptidyl azide is allowed to run for 30 min.

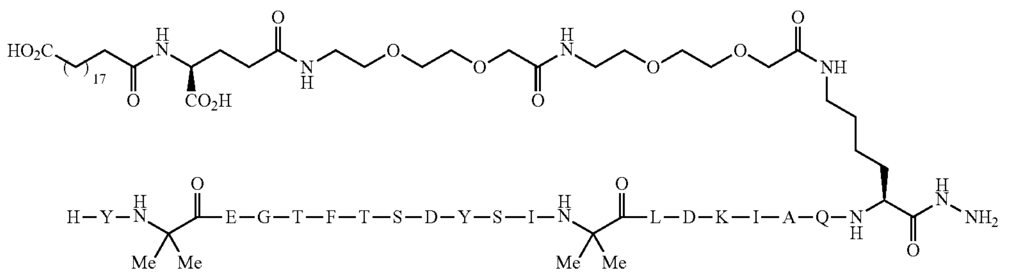

Preparation 39

-continued

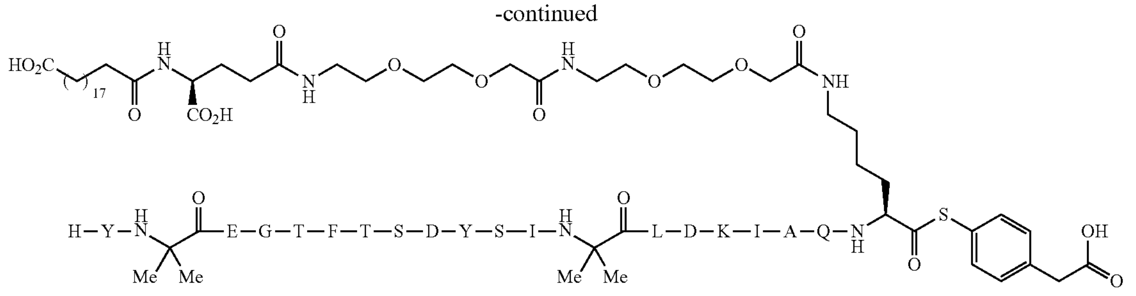

Preparation 41

About 0.62 mmol of Preparation 40 (SEQ ID NO: 37) is synthesized on Sieber amide resin using standard SPPS protocols. N-terminal cysteine containing Preparation 40 (26.1 mg, 0.014 mmol, 0.74 quiv) is dissolved in 1 mL of the ligation buffer. The solution of Preparation 40 is added to the thioester solution. The vial containing Preparation 40 is rinsed with 1 mL of the ligation buffer (pH 7.0) and added to the reaction mixture. After 15 min, 1.0 mL of tris(2-carboxyethyl) phosphine (TCEP, 0.5 M, pH 7.0) is added to the reaction mixture and the pH is adjusted to 7.0 with 5N sodium hydroxide solution. The reaction is allowed to stir at room temperature for an hour. Tirzepatide cysteine analogue Preparation 42 is observed in the reaction mixture.

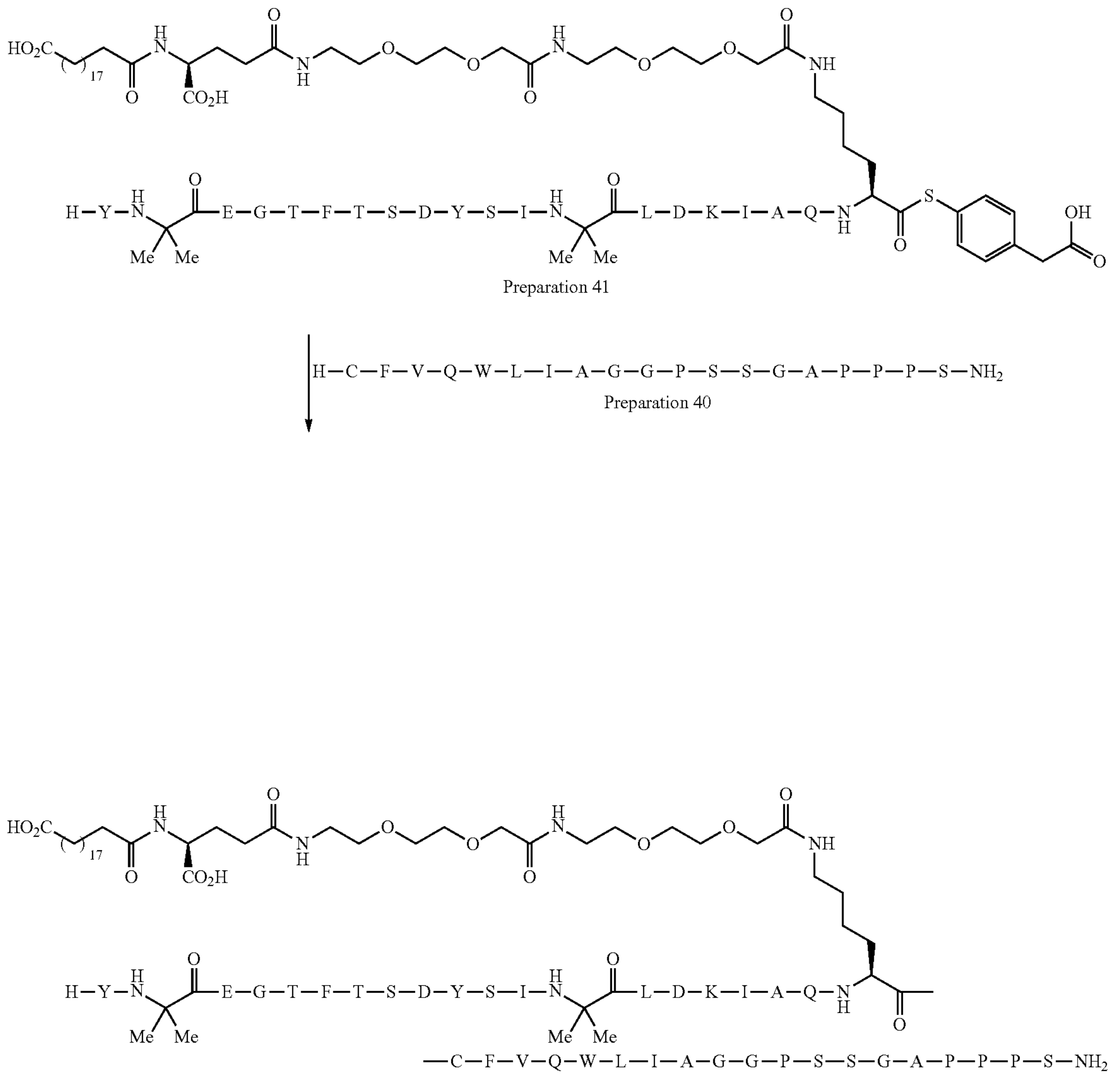

Preparation 42

Sequences

```
Tirzepatide
                                           SEQ ID NO: 1
YX1EGTFTSDYSIX2LDKIAQKAFVQWLIAGGPSSGAPPPS
```

wherein $X_1$ is Aib; $X_2$ is Aib; K at position 20 is chemically modified through conjugation to the epsilon-amino group of the K side-chain with (2-[2-(2-Amino-ethoxy)-ethoxy]-acetyl)$_2$-($\gamma$Glu)$_1$-CO—$(CH_2)_{18}$—$CO_2H$; and the C-terminal amino acid is amidated as a C-terminal primary amide

SEQ ID NO: 2

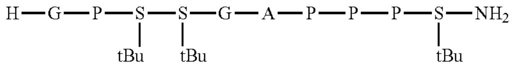

SEQ ID NO: 3

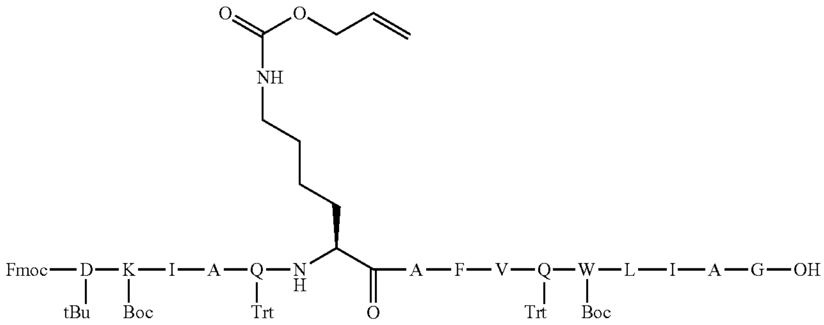

SEQ ID NO: 4

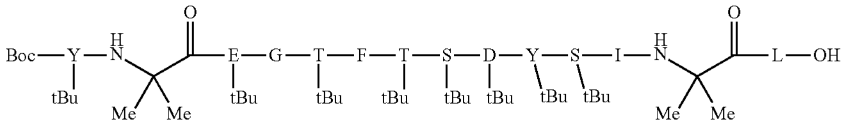

SEQ ID NO: 5

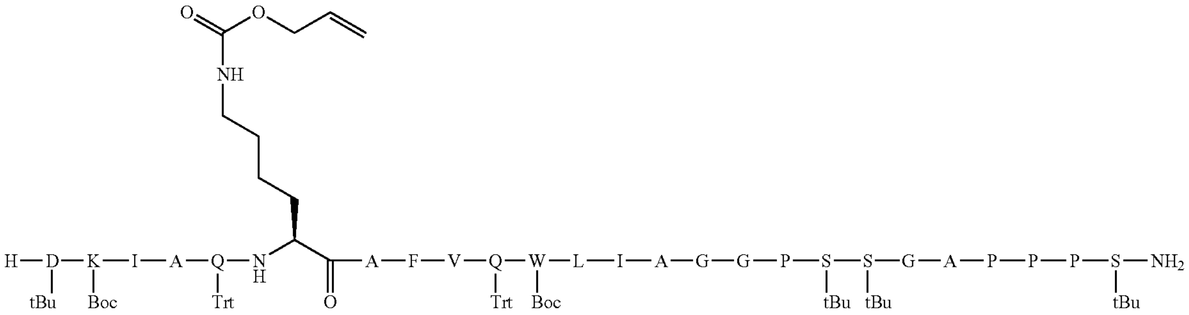

SEQ ID NO: 6

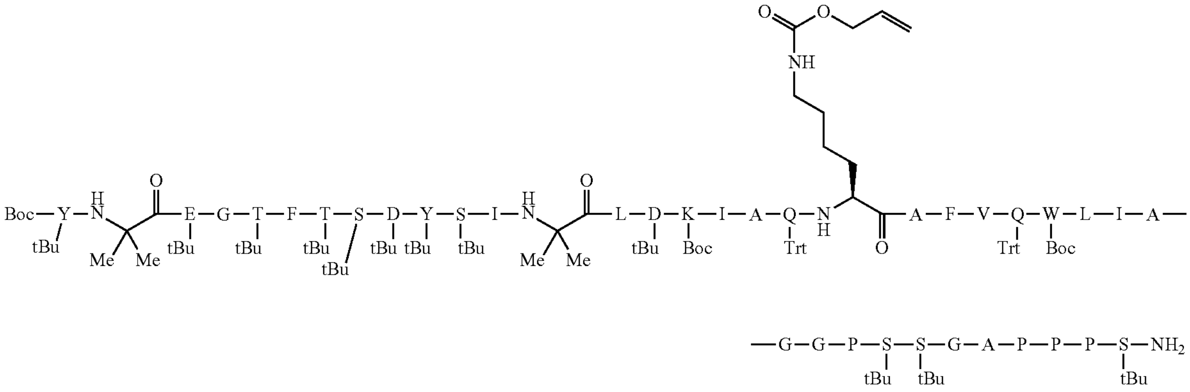

-continued
SEQ ID NO: 7
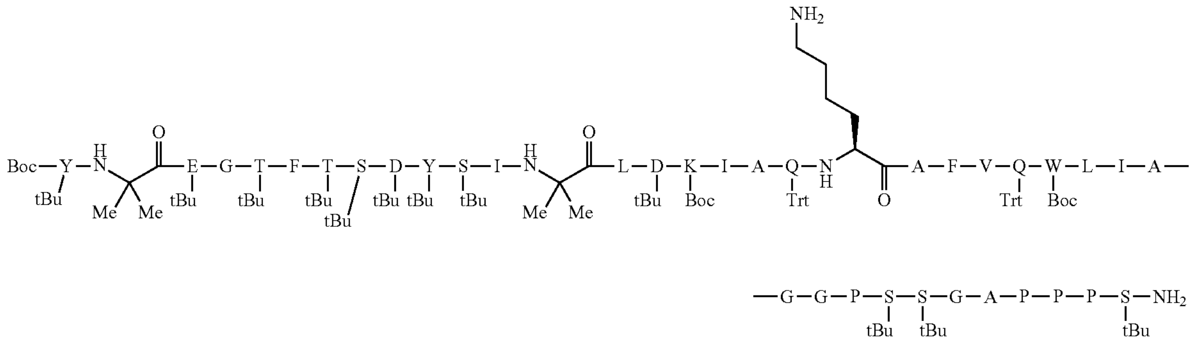
SEQ ID NO: 8
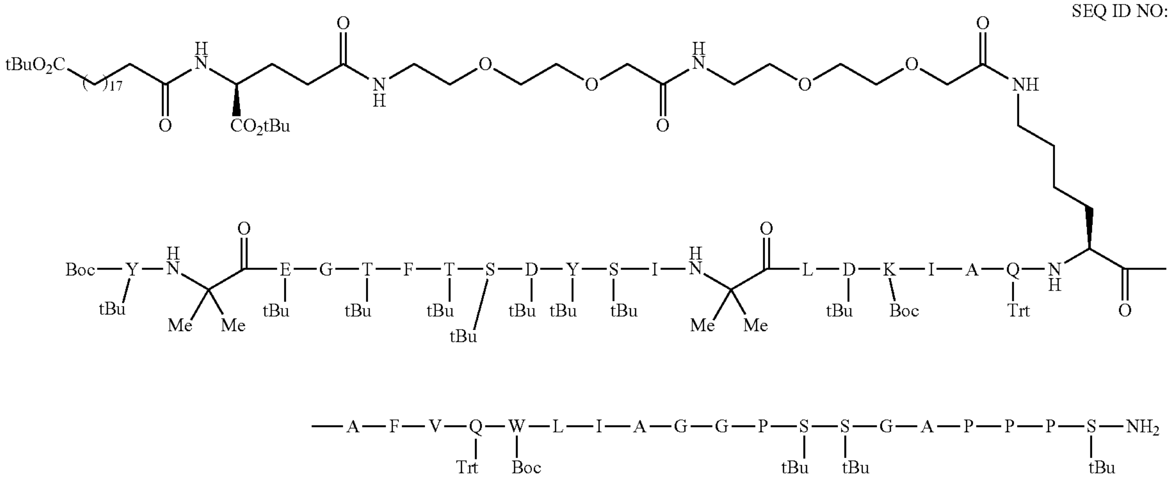
SEQ ID NO: 9
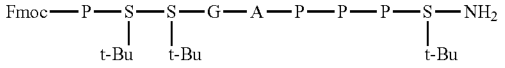
SEQ ID NO: 10
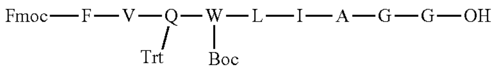
SEQ ID NO: 11
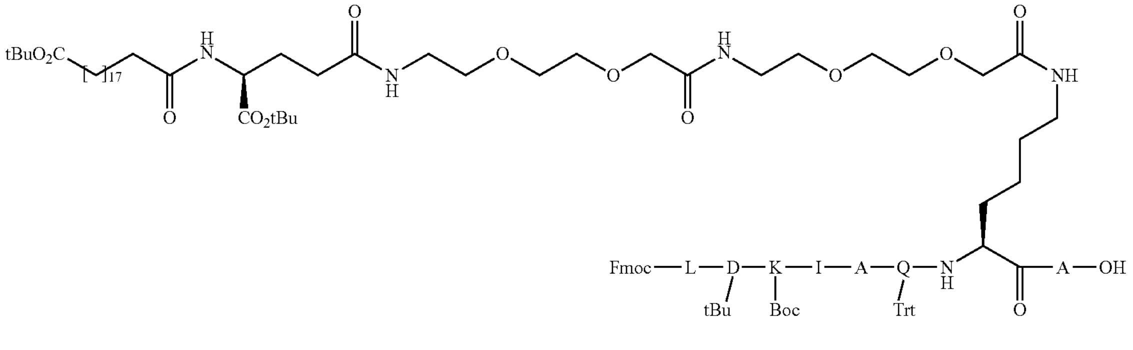
SEQ ID NO: 12
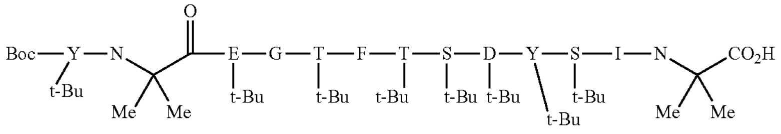
SEQ ID NO: 13
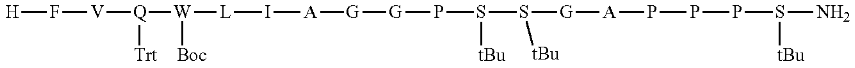

-continued
SEQ ID NO: 14
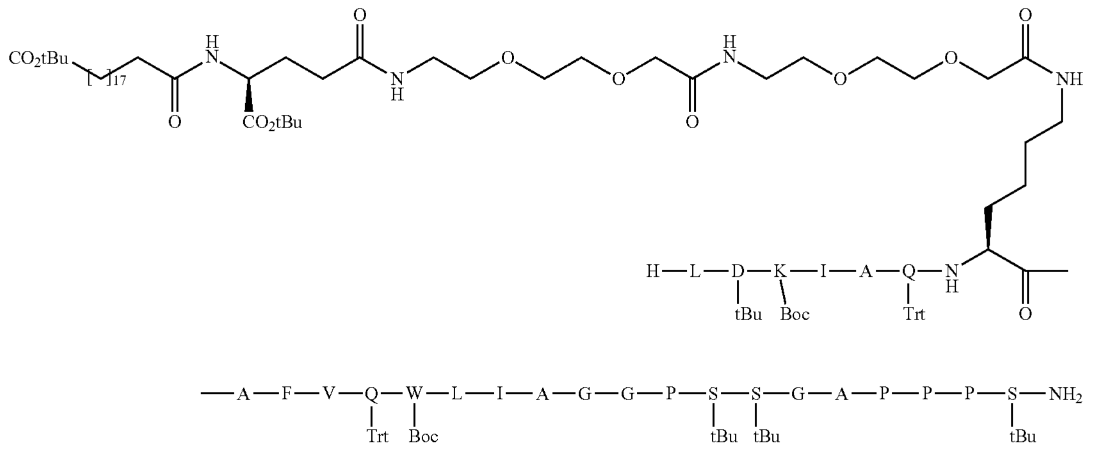
SEQ ID NO: 15
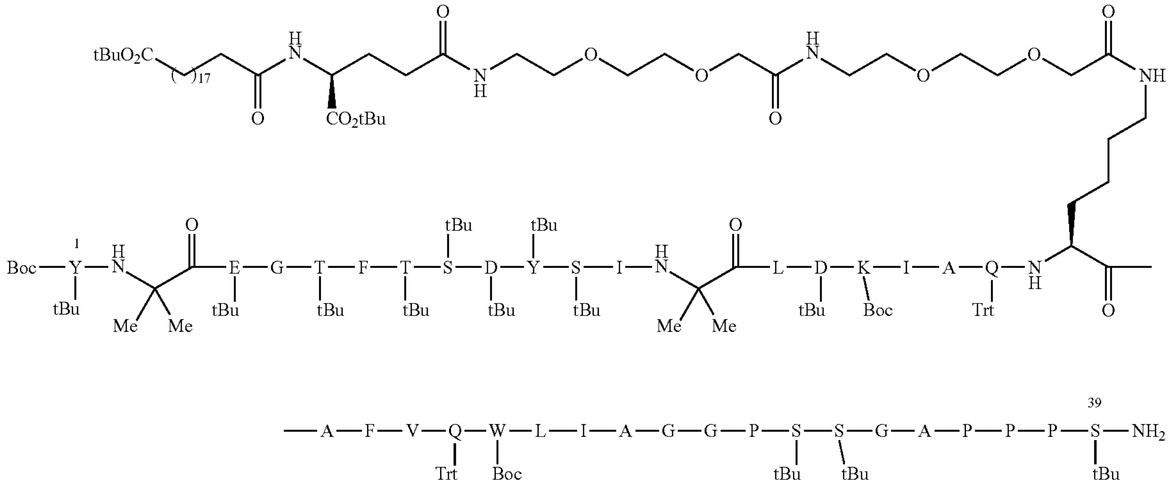
SEQ ID NO: 16
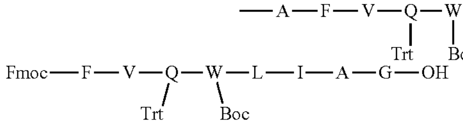
SEQ ID NO: 17
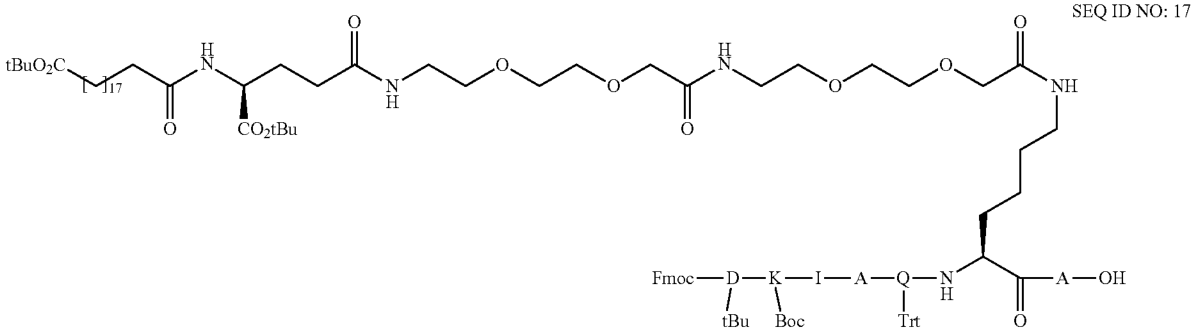
SEQ ID NO: 18
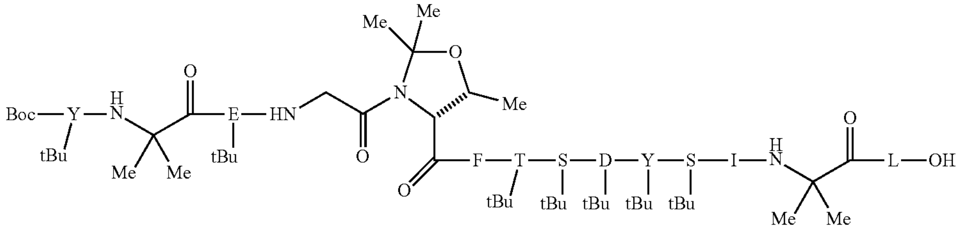
Gly-Thr($\Psi^{Me,Me}$Pro)
Preparation 19A -continued
SEQ ID NO: 19
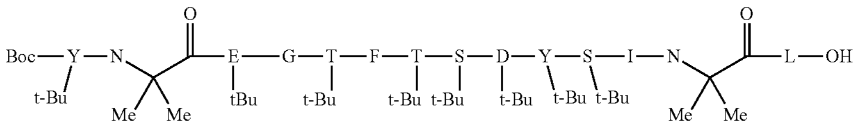
SEQ ID NO: 20
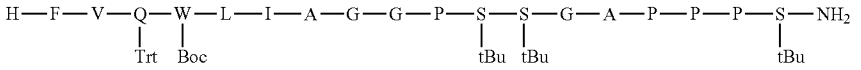
SEQ ID NO: 21
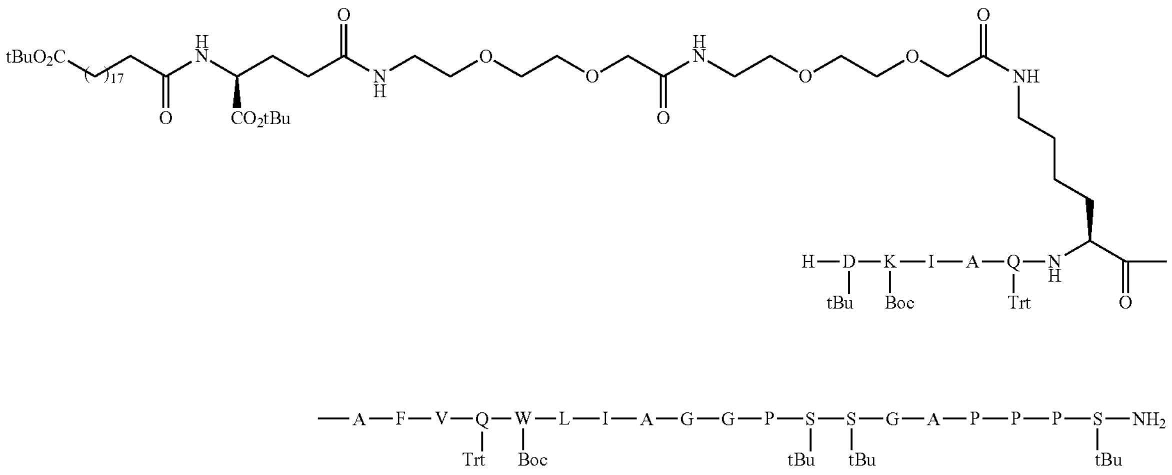
SEQ ID NO: 22
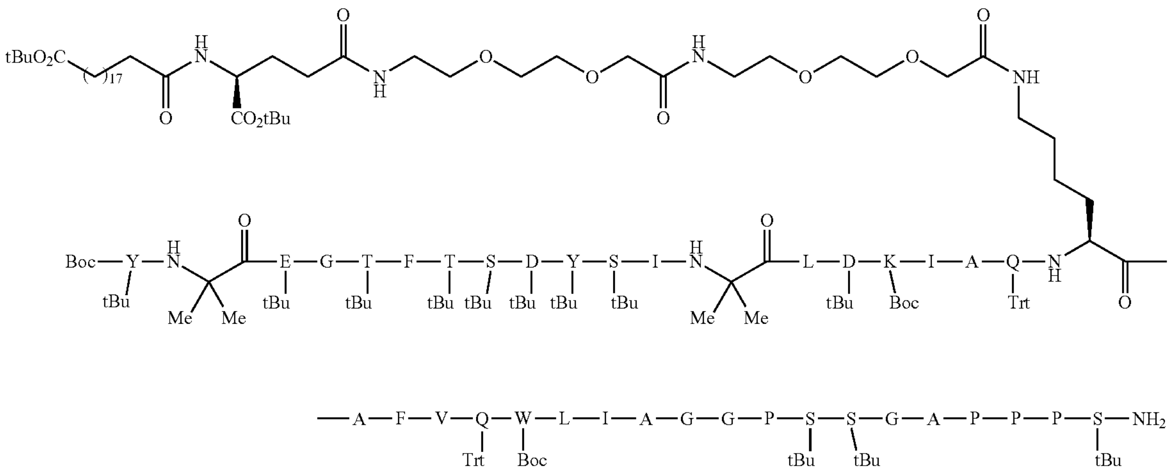

-continued
SEQ ID NO: 23
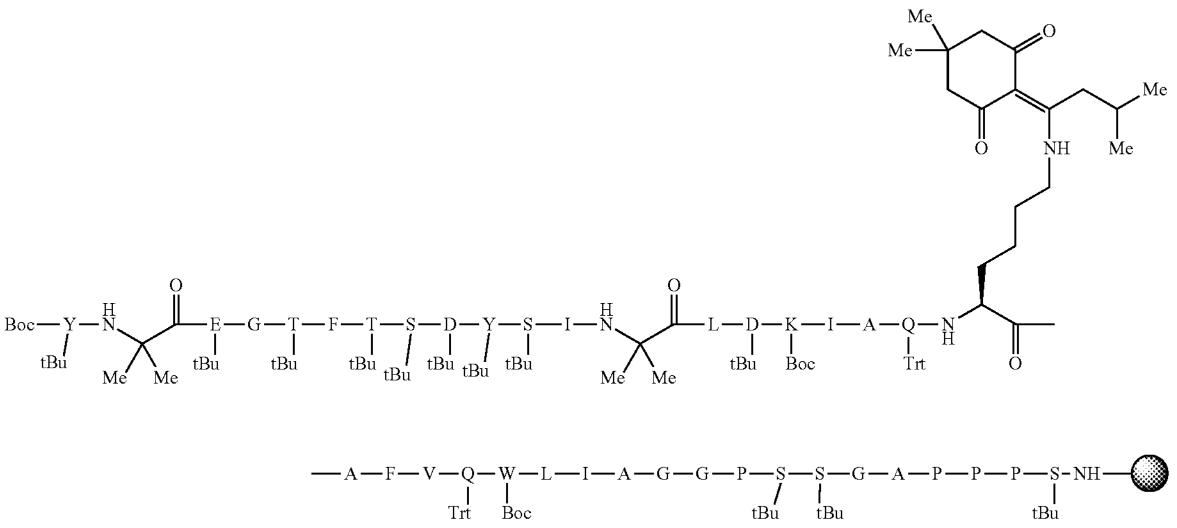
SEQ ID NO: 24
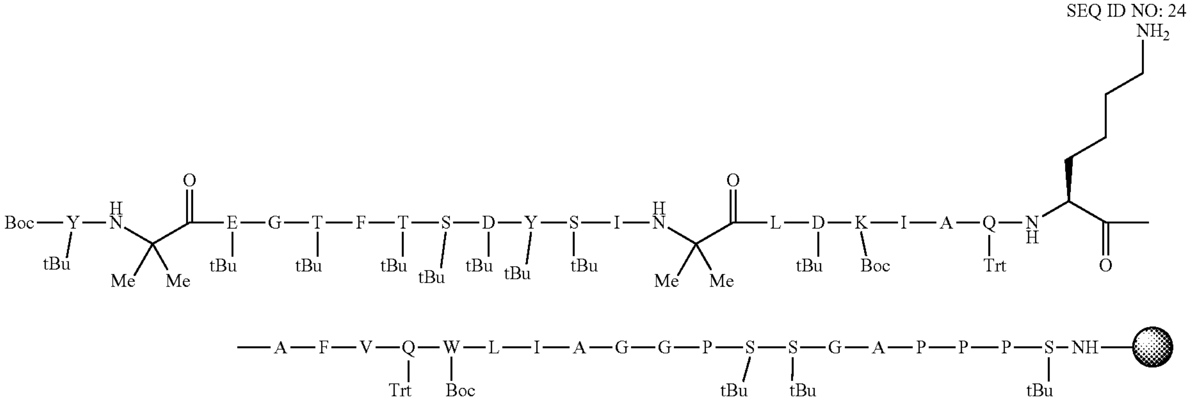
SEQ ID NO: 25
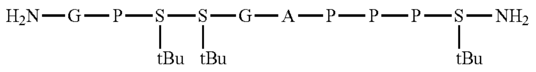
SEQ ID NO: 26
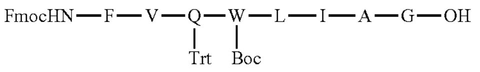
SEQ ID NO: 27
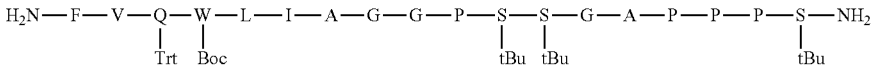
SEQ ID NO: 28
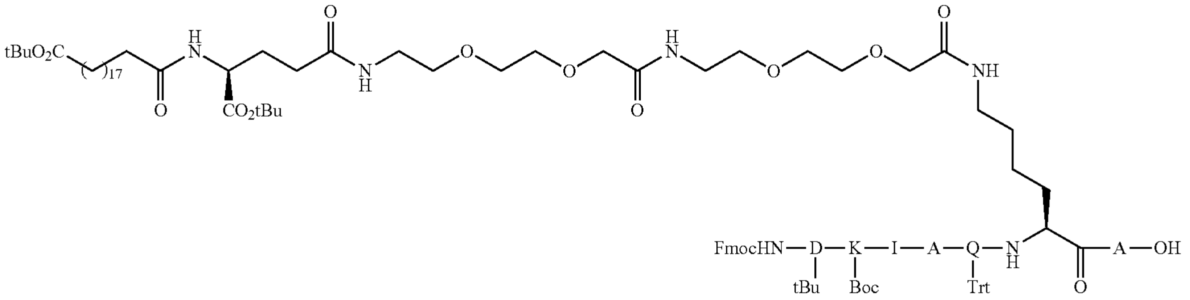

-continued
SEQ ID NO: 29
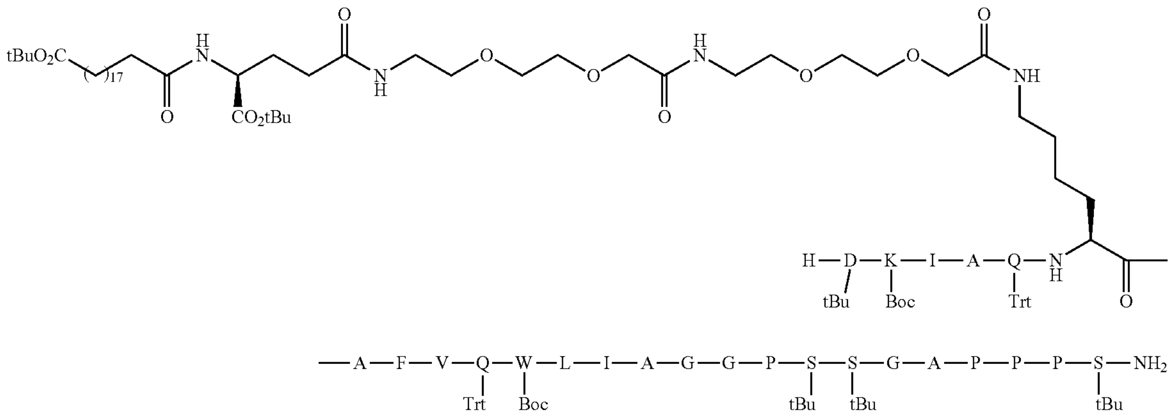
SEQ ID NO: 30
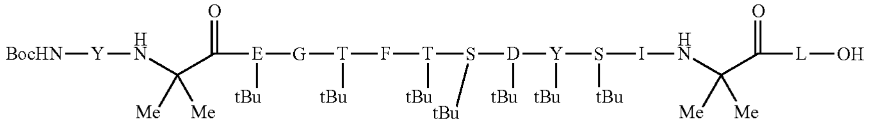
SEQ ID NO: 31
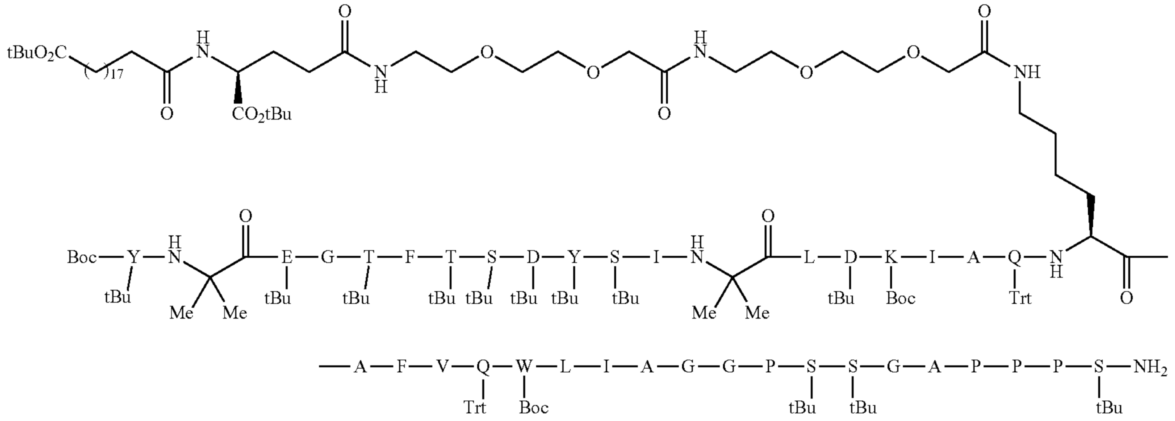
SEQ ID NO: 32
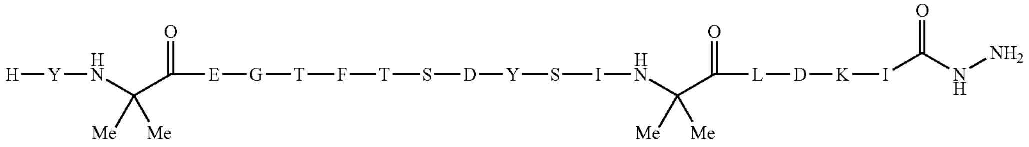
SEQ ID NO: 33
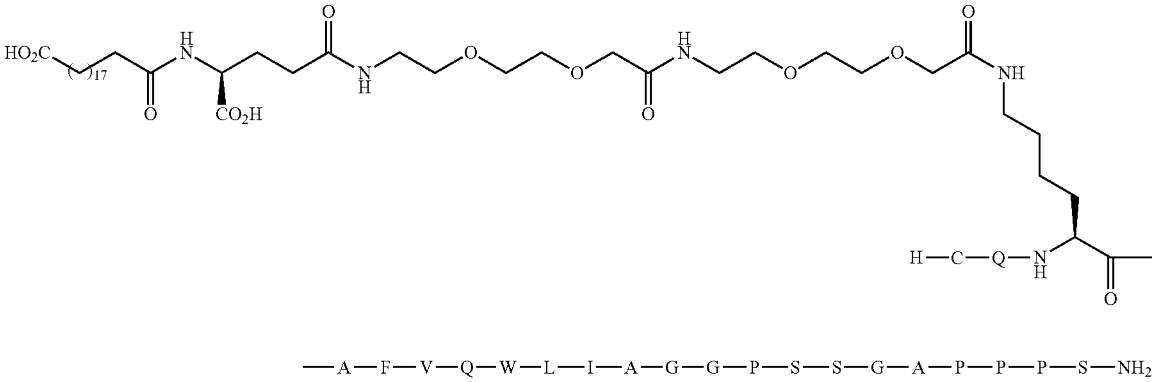

-continued
SEQ ID NO: 34
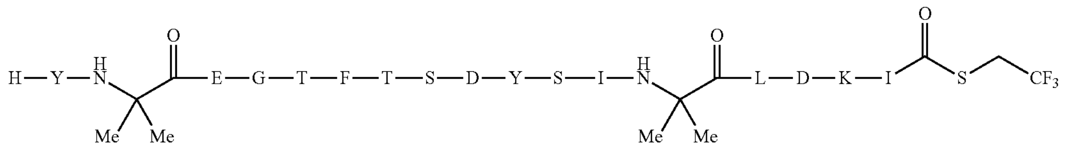
SEQ ID NO: 35
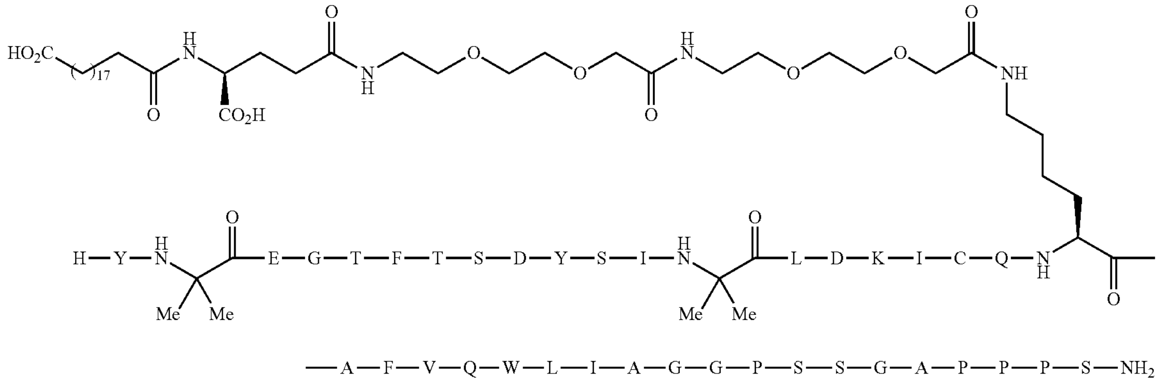
SEQ ID NO: 36
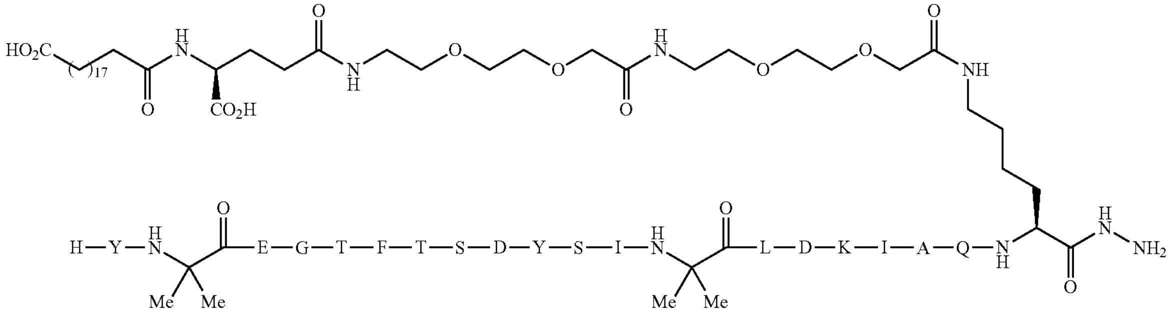
SEQ ID NO: 37
H—C—F—V—Q—W—L—I—A—G—G—P—S—S—G—A—P—P—P—S—$NH_2$
SEQ ID NO: 38
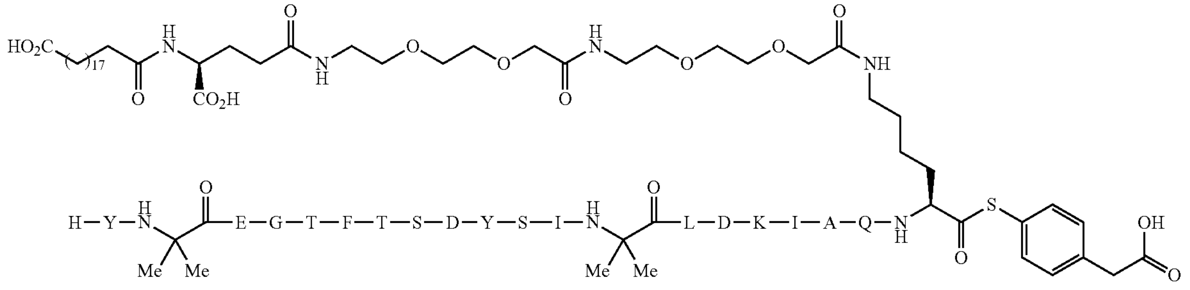

-continued

SEQ ID NO: 39

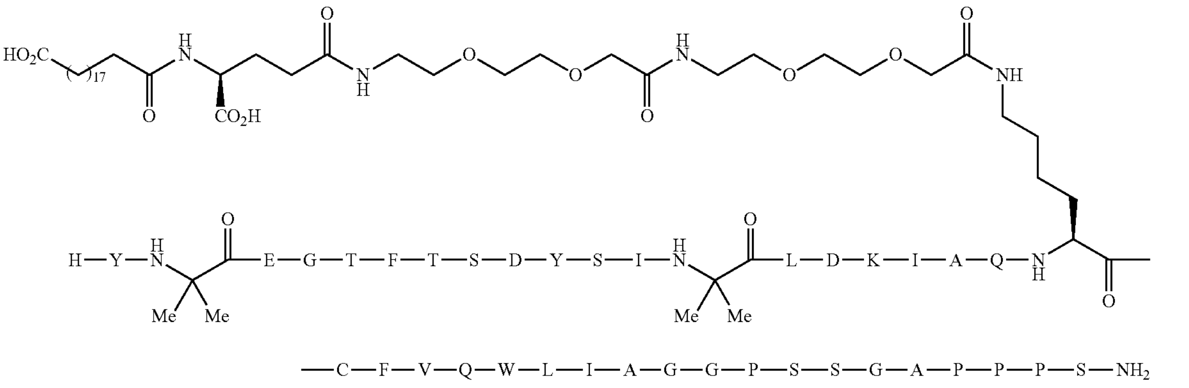

SEQ ID NO: 40

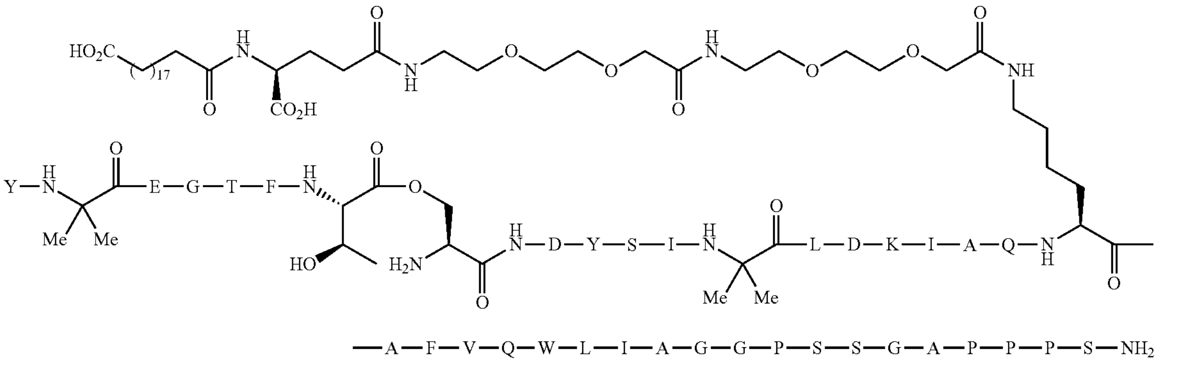

We claim:

1. A process of making a purified tirzepatide (SEQ ID NO: 1) composition comprising:

a. synthesizing tirzepatide intermediate SEQ ID NO: 24 by solid phase peptide synthesis, conjugating the epsilon-amino group of Lys(20) of tirzepatide intermediate SEQ ID NO: 24 with (2-[2-(2-Amino-ethoxy)-ethoxy]-acetyl)$_2$-(gamma-Glu)$_1$-CO—$(CH_2)_{18}$—$CO_2H$, and conducting resin cleavage to yield a crude tirzepatide composition comprising tirzepatide (SEQ ID NO: 1) and 10-15% of depsi peptide isomers of tirzepatide;

b. adjusting the crude tirzepatide composition to a pH between about pH 7 to about pH 10;

c. incubating the crude tirzepatide composition at the pH between about pH 7 to about pH 10 for at least one hour to convert the depsi peptide isomers to tirzepatide (SEQ ID NO: 1); and d. adjusting the composition resulting from step (c) to a pH between about pH 1.5 to about pH 2.5, thereby increasing the purity and yield of tirzepatide relative to a process without steps (b)-(d).

2. A process as claimed by claim 1 wherein the crude tirzepatide composition is adjusted to about pH 8.5 to about pH 9.5.

3. A process as claimed by claim 1 wherein the crude tirzepatide composition is recovered from a process waste stream.

4. A process as claimed by claim 1 wherein the crude tirzepatide composition comprises depsi peptide isomer SEQ ID NO: 40.

5. A process as claimed by claim 1 further comprising a chromatography purification step after step (d).

* * * * *

SEQUENCE LISTING

Sequence total quantity: 40
SEQ ID NO: 1 moltype = AA length = 39
FEATURE Location/Qualifiers
REGION 1..39
note = Synthetic Construct
SITE 2
note = X at position 2 is nonnaturally occurring amino acid 2-Aminoisobutyric Acid
SITE 13
note = X at position 13 is nonnaturally occurring amino acid 2-Aminoisobutyric Acid
MOD_RES 20
note = Lys at position 20 is chemically modified through conjugation to the epsilon-amino group of the K side-chain with (2-[2-(2-Amino-ethoxy)-ethoxy]-acetyl)2-(gamma-Glu)1-CO-(CH 2)18-CO2H
MOD_RES 39
note = Ser at position 39 is amidated as a C-terminal primary amide
source 1..39
mol_type = protein
organism = synthetic construct
SEQUENCE: 1
YXEGTFTSDY SIXLDKIAQK AFVQWLIAGG PSSGAPPPS 39

SEQ ID NO: 2 moltype = AA length = 10
FEATURE Location/Qualifiers
REGION 1..10
note = Synthetic Construct
MOD_RES 3
note = The sidechain of serine is protected by t-butyl.
MOD_RES 4
note = The sidechain of serine is protected by t-butyl.
MOD_RES 10
note = The sidechain of serine is protected by t-butyl.

-continued

```
MOD_RES                 10
                        note = Serine at position 10 is amidated as a C-terminal
                         primary amide.
source                  1..10
                        mol_type = protein
                        organism = synthetic construct
SEQUENCE: 2
GPSSGAPPPS                                                           10

SEQ ID NO: 3            moltype = AA  length = 15
FEATURE                 Location/Qualifiers
REGION                  1..15
                        note = Synthetic Construct
MOD_RES                 1
                        note = N-terminus is protected by Fmoc.
MOD_RES                 1
                        note = The sidechain of aspartic acid is protected by
                         t-butyl.
MOD_RES                 2
                        note = The sidechain of lysine is protected by a
                         t-butyloxycarbonyl (Boc) protecting group.
MOD_RES                 5
                        note = The sidechain of glutamine is protected by a Trityl
                         (Trt) protecting group.
MOD_RES                 6
                        note = The epsilon amino group of K is modified with
                         -CO-O-CH2-CH=CH2
MOD_RES                 10
                        note = The sidechain of glutamine is protected by a Trityl
                         (Trt) protecting group.
MOD_RES                 11
                        note = The sidechain of Tryptophan is protected by a
                         t-butyloxycarbonyl (Boc) protecting group.
source                  1..15
                        mol_type = protein
                        organism = synthetic construct
SEQUENCE: 3
DKIAQKAFVQ WLIAG                                                     15

SEQ ID NO: 4            moltype = AA  length = 14
FEATURE                 Location/Qualifiers
REGION                  1..14
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
SITE                    2
                        note = X at position 2 is 2-Aminoisobutyric Acid (Aib)
MOD_RES                 3
                        note = The sidechain of glutamic acid is protected with
                         t-Butyl.
MOD_RES                 5
                        note = The sidechain of threonine is protected with t-Butyl.
MOD_RES                 7
                        note = The sidechain of threonine is protected with t-Butyl.
MOD_RES                 8
                        note = The sidechain of serine is protected with t-Butyl.
MOD_RES                 9
                        note = The sidechain of aspartic acid is protected with
                         t-Butyl.
MOD_RES                 10
                        note = The sidechain of tyrosine is protected with t-Butyl.
MOD_RES                 11
                        note = The sidechain of serine is protected with t-Butyl.
SITE                    13
                        note = X at position 13 is 2-Aminoisobutyric Acid (Aib)
source                  1..14
                        mol_type = protein
                        organism = synthetic construct
SEQUENCE: 4
YXEGTFTSDY SIXL                                                      14

SEQ ID NO: 5            moltype = AA  length = 25
FEATURE                 Location/Qualifiers
REGION                  1..25
                        note = Synthetic Construct
MOD_RES                 1
                        note = The sidechain of aspartic acid is protected by
```

-continued

```
                         t-butyl.
MOD_RES                 2
                        note = The sidechain of lysine is protected by a
                         t-butyloxycarbonyl (Boc) protecting group.
MOD_RES                 5
                        note = The sidechain of glutamine is protected by a Trityl
                         (Trt) protecting group.
MOD_RES                 6
                        note = The lysine at position 6 is chemically modified
                         through conjugation to the epsilon-amino group of the K
                         side-chain with C(O)-O-CH2-CH=CH2.
MOD_RES                 10
                        note = The sidechain of glutamine is protected by a Trityl
                         (Trt) protecting group.
MOD_RES                 11
                        note = The sidechain of tryptophan is protected by Boc.
MOD_RES                 18
                        note = The sidechain od serine is protected by t-butyl.
MOD_RES                 19
                        note = The sidechain of serine is protected by t-butyl.
MOD_RES                 25
                        note = The sidechain of serine is protected by t-butyl.
MOD_RES                 25
                        note = Serine at position 25 is amidated as a C-terminal
                         primary amide.
source                  1..25
                        mol_type = protein
                        organism = synthetic construct
SEQUENCE: 5
DKIAQKAFVQ WLIAGGPSSG APPPS                                          25

SEQ ID NO: 6            moltype = AA  length = 39
FEATURE                 Location/Qualifiers
REGION                  1..39
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
SITE                    2
                        note = X at position 2 is 2-Aminoisobutyric Acid (Aib)
MOD_RES                 3
                        note = The sidechain of glutamic acid is protected by
                         t-butyl.
MOD_RES                 5
                        note = The sidechain of threoinine is protected by t-butyl.
MOD_RES                 7
                        note = The sidechain of threoinine is protected by t-butyl.
MOD_RES                 8
                        note = The sidechain of serine is protected by t-butyl.
MOD_RES                 9
                        note = The sidechain of aspartic acic is protected by
                         t-butyl.
MOD_RES                 10
                        note = The sidechain of tyrosine is protected by t-butyl.
MOD_RES                 11
                        note = The sidechain of serine is protected by t-butyl.
SITE                    13
                        note = X at position 13 is 2-Aminoisobutyric Acid (Aib)
MOD_RES                 15
                        note = The sidechain of aspartic acid is protected by
                         t-butyl.
MOD_RES                 16
                        note = The sidechain of lysine is protected by a
                         t-butyloxycarbonyl (Boc) protecting group.
MOD_RES                 19
                        note = The sidechain of glutamine is protected by a Trityl
                         (Trt) protecting group.
MOD_RES                 20
                        note = The lysine at position 6 is chemically modified
                         through conjugation to the epsilon-amino group of the K
                         side-chain with C(O)-O-CH2-CH=CH2.
MOD_RES                 24
                        note = The sidechain of glutamine is protected by a Trityl
                         (Trt) protecting group.
MOD_RES                 25
                        note = The sidechain of Tryptophan is protected by a
                         t-butyloxycarbonyl (Boc) protecting group.
MOD_RES                 32
```

-continued

```
                        note = The sidechain of serine is protected by t-butyl.
MOD_RES                 33
                        note = The sidechain of serine is protected by t-butyl.
MOD_RES                 39
                        note = The sidechain of serine is protected by t-butyl.
MOD_RES                 39
                        note = Serine at position 39 is amidated as a C-terminal
                         primary amide.
source                  1..39
                        mol_type = protein
                        organism = synthetic construct
SEQUENCE: 6
YXEGTFTSDY SIXLDKIAQK AFVQWLIAGG PSSGAPPPS                         39

SEQ ID NO: 7            moltype = AA  length = 39
FEATURE                 Location/Qualifiers
REGION                  1..39
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
SITE                    2
                        note = X at position 2 is 2-Aminoisobutyric Acid (Aib)
MOD_RES                 3
                        note = The sidechain of glutamic acid is protected by
                         t-butyl.
MOD_RES                 5
                        note = The sidechain of threonine is protected by t-butyl.
MOD_RES                 7
                        note = The sidechain of threonine is protected by t-butyl.
MOD_RES                 8
                        note = The sidechain of serine is protected by t-butyl.
MOD_RES                 9
                        note = The sidechain of aspartic acid is protected by
                         t-butyl.
MOD_RES                 10
                        note = The sidechain of tyrosine is protected by t-butyl.
MOD_RES                 11
                        note = The sidechain of serine is protected by t-butyl.
SITE                    13
                        note = X at position 13 is 2-Aminoisobutyric Acid (Aib)
MOD_RES                 15
                        note = The sidechain of aspartic acid is protected by
                         t-butyl.
MOD_RES                 16
                        note = The sidechain of lysine is protected by a
                         t-butyloxycarbonyl (Boc) protecting group.
MOD_RES                 19
                        note = The sidechain of glutamine is protected by a Trityl
                         (Trt) protecting group.
MOD_RES                 24
                        note = The sidechain of glutamine is protected by a Trityl
                         (Trt) protecting group.
MOD_RES                 25
                        note = The sidechain of Tryptophan is protected by a
                         t-butyloxycarbonyl (Boc) protecting group.
MOD_RES                 32
                        note = The sidechain of serine is protected by t-butyl.
MOD_RES                 33
                        note = The sidechain of serine is protected by t-butyl.
MOD_RES                 39
                        note = The sidechain of serine is protected by t-butyl.
MOD_RES                 39
                        note = Serine at position 39 is amidated as a C-terminal
                         primary amide.
source                  1..39
                        mol_type = protein
                        organism = synthetic construct
SEQUENCE: 7
YXEGTFTSDY SIXLDKIAQK AFVQWLIAGG PSSGAPPPS                         39

SEQ ID NO: 8            moltype = AA  length = 39
FEATURE                 Location/Qualifiers
REGION                  1..39
                        note = Synthetic Construct
MOD_RES                 1
                        note = N-terminus is protected by (t-butyloxycarbonyl) Boc.
MOD_RES                 1
```

-continued

```
                      note = The sidechain of tyrosine is protected by t-butyl.
SITE                  2
                      note = X at position 2 is 2-Aminoisobutyric Acid (Aib)
MOD_RES               3
                      note = The sidechain of glutamic acid is protected by
                       t-butyl.
MOD_RES               5
                      note = The sidechain of threonine is protected by t-butyl.
MOD_RES               7
                      note = The sidechain of threonine is protected by t-butyl.
MOD_RES               8
                      note = The sidechain of serine is protected by t-butyl.
MOD_RES               9
                      note = The sidechain of aspartic acid is protected by
                       t-butyl.
MOD_RES               10
                      note = The sidechain of tyrosine is protected by t-butyl.
MOD_RES               11
                      note = The sidechain of serine is protected by t-butyl.
MOD_RES               15
                      note = The sidechain of aspartic acid is protected by
                       t-butyl.
MOD_RES               16
                      note = The sidechain of lysine is protected by a
                       t-butyloxycarbonyl (Boc) protecting group.
MOD_RES               19
                      note = The sidechain of glutamine is protected by a Trityl
                       (Trt) protecting group.
MOD_RES               20
                      note = Lys at position 20 is chemically modified through
                       conjugation to the epsilon-amino group of the K side-chain
                       with
                       (2-[2-(2-Amino-ethoxy)-ethoxy]-acetyl)2-(gamma-Glu(t-butyl)
                       )1-CO-(CH2)18-CO2-(t-butyl).
MOD_RES               24
                      note = The sidechain of glutamine is protected by a Trityl
                       (Trt) protecting group.
MOD_RES               25
                      note = The sidechain of Tryptophan is protected by a
                       t-butyloxycarbonyl (Boc) protecting group.
MOD_RES               32
                      note = The sidechain of serine is protected by t-butyl.
MOD_RES               33
                      note = The sidechain of serine is protected by t-butyl.
MOD_RES               39
                      note = The sidechain of serine is protected by t-butyl.
MOD_RES               39
                      note = Serine at position 39 is amidated as a C-terminal
                       primary amide.
source                1..39
                      mol_type = protein
                      organism = synthetic construct
SITE                  13
                      note = X at position 13 is 2-Aminoisobutyric Acid (Aib)
SEQUENCE: 8
YXEGTFTSDY SIXLDKIAQK AFVQWLIAGG PSSGAPPPS                         39

SEQ ID NO: 9          moltype = AA  length = 9
FEATURE               Location/Qualifiers
REGION                1..9
                      note = Synthetic Construct
MOD_RES               1
                      note = N-terminus is protected by Fmoc.
MOD_RES               2
                      note = The sidechain of serine is protected by t-butyl.
MOD_RES               3
                      note = The sidechain of serine is protected by t-butyl.
MOD_RES               9
                      note = The sidechain of serine is protected by t-butyl.
MOD_RES               9
                      note = Serine at position 9 is amidated as a C-terminal
                       primary amide.
source                1..9
                      mol_type = protein
                      organism = synthetic construct
SEQUENCE: 9
PSSGAPPPS                                                          9

SEQ ID NO: 10         moltype = AA  length = 9
```

-continued

```
FEATURE                 Location/Qualifiers
REGION                  1..9
                        note = Synthetic Construct
MOD_RES                 1
                        note = N-terminus is protected by Fmoc.
MOD_RES                 3
                        note = The sidechain of glutamine is protected by a Trityl
                         (Trt) protecting group.
MOD_RES                 4
                        note = The sidechain of Tryptophan is protected by a
                         t-butyloxycarbonyl (Boc) protecting group.
source                  1..9
                        mol_type = protein
                        organism = synthetic construct
SEQUENCE: 10
FVQWLIAGG                                                         9

SEQ ID NO: 11           moltype = AA  length = 8
FEATURE                 Location/Qualifiers
REGION                  1..8
                        note = Synthetic Construct
MOD_RES                 1
                        note = N-terminus is protected by Fmoc.
MOD_RES                 2
                        note = The sidechain of aspartic acid is protected by
                         t-butyl.
MOD_RES                 3
                        note = The sidechain of lysine is protected by a
                         t-butyloxycarbonyl (Boc) protecting group.
MOD_RES                 6
                        note = The sidechain of glutamine is protected by a Trityl
                         (Trt) protecting group.
MOD_RES                 7
                        note = Lys at position 7 is chemically modified through
                         conjugation to the epsilon-amino group of the K side-chain
                         with
                         (2-[2-(2-Amino-ethoxy)-ethoxy]-acetyl)2-(gamma-Glu(t-butyl)
                         )1-CO-(CH2)18-CO2-(t-butyl).
source                  1..8
                        mol_type = protein
                        organism = synthetic construct
SEQUENCE: 11
LDKIAQKA                                                          8

SEQ ID NO: 12           moltype = AA  length = 13
FEATURE                 Location/Qualifiers
REGION                  1..13
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
MOD_RES                 2
                        note = Xaa at position 2 is 2-Aminoisobutyric Acid (Aib).
MOD_RES                 3
                        note = The sidechain of glutamic acid is protected by
                         t-butyl.
MOD_RES                 5
                        note = The sidechain of threonine is protected by t-butyl.
MOD_RES                 7
                        note = The sidechain of threonine is protected by t-butyl.
MOD_RES                 8
                        note = The sidechain of serine is protected by t-butyl.
MOD_RES                 9
                        note = The sidechain of aspartic acid is protected by
                         t-butyl.
MOD_RES                 10
                        note = The sidechain of tyrosine is protected by t-butyl.
MOD_RES                 11
                        note = The sidechain of serine is protected by t-butyl.
SITE                    13
                        note = X at position 13 is 2-Aminoisobutyric Acid (Aib)
source                  1..13
                        mol_type = protein
                        organism = synthetic construct
SEQUENCE: 12
YXEGTFTSDY SIX                                                    13

SEQ ID NO: 13           moltype = AA  length = 18
```

-continued

```
FEATURE                Location/Qualifiers
REGION                 1..18
                       note = Synthetic Construct
MOD_RES                3
                       note = The sidechain of glutamine is protected by a Trityl
                        (Trt) protecting group.
MOD_RES                4
                       note = The sidechain of Tryptophan is protected by a
                        t-butyloxycarbonyl (Boc) protecting group.
MOD_RES                11
                       note = The sidechain of serine is protected by t-butyl.
MOD_RES                12
                       note = The sidechain of serine is protected by t-butyl.
MOD_RES                18
                       note = The sidechain of serine is protected by t-butyl.
MOD_RES                18
                       note = Serine at position 18 is amidated as a C-terminal
                        primary amide.
source                 1..18
                       mol_type = protein
                       organism = synthetic construct
SEQUENCE: 13
FVQWLIAGGP SSGAPPPS                                                18

SEQ ID NO: 14          moltype = AA  length = 26
FEATURE                Location/Qualifiers
REGION                 1..26
                       note = Synthetic Construct
MOD_RES                2
                       note = The sidechain of aspartic acid is protected by
                        t-butyl.
MOD_RES                3
                       note = The sidechain of lysine is protected by a
                        t-butyloxycarbonyl (Boc) protecting group.
MOD_RES                6
                       note = The sidechain of glutamine is protected by a Trityl
                        (Trt) protecting group.
MOD_RES                7
                       note = Lys at position 7 is chemically modified through
                        conjugation to the epsilon-amino group of the K side-chain
                        with
                        (2-[2-(2-Amino-ethoxy)-ethoxy]-acetyl)2-(gamma-Glu(t-butyl)
                        )1-CO-(CH2)18-CO2-(t-butyl).
MOD_RES                11
                       note = The sidechain of glutamine is protected by a Trityl
                        (Trt) protecting group.
MOD_RES                12
                       note = The sidechain of Tryptophan is protected by a
                        t-butyloxycarbonyl (Boc) protecting group.
MOD_RES                19
                       note = The sidechain of serine is protected by t-butyl.
MOD_RES                20
                       note = The sidechain of serine is protected by t-butyl.
MOD_RES                26
                       note = The sidechain of serine is protected by t-butyl.
MOD_RES                26
                       note = Serine at position 26 is amidated as a C-terminal
                        primary amide.
source                 1..26
                       mol_type = protein
                       organism = synthetic construct
SEQUENCE: 14
LDKIAQKAFV QWLIAGGPSS GAPPPS                                       26

SEQ ID NO: 15          moltype = AA  length = 39
FEATURE                Location/Qualifiers
REGION                 1..39
                       note = Synthetic Construct
MOD_RES                1
                       note = N-terminus is protected by (t-butyloxycarbonyl) Boc.
MOD_RES                1
                       note = The sidechain of tyrosine is protected by t-butyl.
SITE                   2
                       note = X at position 2 is 2-Aminoisobutyric Acid (Aib)
MOD_RES                3
                       note = The sidechain of glutamic acid is protected by
                        t-butyl.
MOD_RES                5
                       note = The sidechain of threonine is protected by t-butyl.
```

-continued

```
MOD_RES                 7
                        note = The sidechain of threonine is protected by t-butyl.
MOD_RES                 8
                        note = The sidechain of serine is protected by t-butyl.
MOD_RES                 9
                        note = The sidechain of aspartic acid is protected by
                         t-butyl.
MOD_RES                 10
                        note = The sidechain of tyrosine is protected by t-butyl.
MOD_RES                 11
                        note = The sidechain of serine is protected by t-butyl.
SITE                    13
                        note = X at position 13 is 2-Aminoisobutyric Acid (Aib)
MOD_RES                 15
                        note = The sidechain of aspartic acid is protected by
                         t-butyl.
MOD_RES                 16
                        note = The sidechain of lysine is protected by a
                         t-butyloxycarbonyl (Boc) protecting group.
MOD_RES                 19
                        note = The sidechain of glutamine is protected by a Trityl
                         (Trt) protecting group.
MOD_RES                 20
                        note = Lys at position 20 is chemically modified through
                         conjugation to the epsilon-amino group of the K side-chain
                         with
                         (2-[2-(2-Amino-ethoxy)-ethoxy]-acetyl)2-(gamma-Glu(t-butyl)
                         )1-CO-(CH2)18-CO2-(t-butyl).
MOD_RES                 24
                        note = The sidechain of glutamine is protected by a Trityl
                         (Trt) protecting group.
MOD_RES                 25
                        note = The sidechain of Tryptophan is protected by a
                         t-butyloxycarbonyl (Boc) protecting group.
MOD_RES                 32
                        note = The sidechain of serine is protected by t-butyl.
MOD_RES                 33
                        note = The sidechain of serine is protected by t-butyl.
MOD_RES                 39
                        note = The sidechain of serine is protected by t-butyl.
MOD_RES                 39
                        note = Serine at position 39 is amidated as a C-terminal
                         primary amide.
source                  1..39
                        mol_type = protein
                        organism = synthetic construct
SEQUENCE: 15
YXEGTFTSDY SIXLDKIAQK AFVQWLIAGG PSSGAPPPS                        39

SEQ ID NO: 16           moltype = AA  length = 8
FEATURE                 Location/Qualifiers
REGION                  1..8
                        note = Synthetic Construct
MOD_RES                 1
                        note = N-terminus is protected by Fmoc.
MOD_RES                 3
                        note = The sidechain of glutamine is protected by a Trityl
                         (Trt) protecting group.
MOD_RES                 4
                        note = The sidechain of Tryptophan is protected by a
                         t-butyloxycarbonyl (Boc) protecting group.
source                  1..8
                        mol_type = protein
                        organism = synthetic construct
SEQUENCE: 16
FVQWLIAG                                                          8

SEQ ID NO: 17           moltype = AA  length = 7
FEATURE                 Location/Qualifiers
REGION                  1..7
                        note = Synthetic Construct
MOD_RES                 1
                        note = N-terminus is protected by Fmoc.
MOD_RES                 1
                        note = The sidechain of aspartic acid is protected by
                         t-butyl.
MOD_RES                 2
                        note = The sidechain of lysine is protected by a
                         t-butyloxycarbonyl (Boc) protecting group.
```

-continued

```
MOD_RES                5
                       note = The sidechain of glutamine is protected by a Trityl
                        (Trt) protecting group.
MOD_RES                6
                       note = Lys at position 6 is chemically modified through
                        conjugation to the epsilon-amino group of the K side-chain
                        with
                        (2-[2-(2-Amino-ethoxy)-ethoxy]-acetyl)2-(gamma-Glu(t-butyl)
                        )1-CO-(CH2)18-CO2-(t-butyl).
source                 1..7
                       mol_type = protein
                       organism = synthetic construct
SEQUENCE: 17
DKIAQKA                                                                  7

SEQ ID NO: 18          moltype = AA  length = 14
FEATURE                Location/Qualifiers
REGION                 1..14
                       note = Synthetic Construct
MOD_RES                1
                       note = N-terminus is protected by (t-butyloxycarbonyl) Boc.
MOD_RES                1
                       note = The sidechain of tyrosine is protected by t-butyl.
SITE                   2
                       note = X at position 2 is 2-Aminoisobutyric Acid (Aib)
MOD_RES                3
                       note = The sidechain of glutamic acid is protected by
                        t-butyl.
MOD_RES                5
                       note = The glycine at position 4 combines with position 5
                        to create Gly-Thr (psiMe,Me-Pro) using pseudoproline.
MOD_RES                7
                       note = The sidechain of threonine is protected by t-butyl.
MOD_RES                8
                       note = The sidechain of serine is protected by t-butyl.
MOD_RES                9
                       note = The sidechain of aspartic acid is protected by
                        t-butyl.
MOD_RES                10
                       note = The sidechain of tyrosine is protected by t-butyl.
MOD_RES                11
                       note = The sidechain of serine is protected by t-butyl.
SITE                   13
                       note = X at position 13 is 2-Aminoisobutyric Acid (Aib)
source                 1..14
                       mol_type = protein
                       organism = synthetic construct
SEQUENCE: 18
YXEGXFTSDY SIXL                                                          14

SEQ ID NO: 19          moltype = AA  length = 14
FEATURE                Location/Qualifiers
REGION                 1..14
                       note = Synthetic Construct
MOD_RES                1
                       note = N-terminus is protected by (t-butyloxycarbonyl) Boc.
MOD_RES                1
                       note = The sidechain of tyrosine is protected by t-butyl.
SITE                   2
                       note = X at position 2 is 2-Aminoisobutyric Acid (Aib)
MOD_RES                3
                       note = The sidechain of glutamic acid is protected by
                        t-butyl.
MOD_RES                5
                       note = The sidechain of threonine is protected by t-butyl.
MOD_RES                7
                       note = The sidechain of threonine is protected by t-butyl.
MOD_RES                8
                       note = The sidechain of serine is protected by t-butyl.
MOD_RES                9
                       note = The sidechain of aspartic acid is protected by
                        t-butyl.
MOD_RES                10
                       note = The sidechain of tyrosine is protected by t-butyl.
MOD_RES                11
                       note = The sidechain of serine is protected by t-butyl.
SITE                   13
                       note = X at position 13 is 2-Aminoisobutyric Acid (Aib)
source                 1..14
```

```
                        mol_type = protein
                        organism = synthetic construct
SEQUENCE: 19
YXEGTFTSDY SIXL                                                 14

SEQ ID NO: 20           moltype = AA  length = 18
FEATURE                 Location/Qualifiers
REGION                  1..18
                        note = Synthetic Construct
MOD_RES                 3
                        note = The sidechain of glutamine is protected by a Trityl
                         (Trt) protecting group.
MOD_RES                 4
                        note = The sidechain of Tryptophan is protected by a
                         t-butyloxycarbonyl (Boc) protecting group.
MOD_RES                 11
                        note = The sidechain of serine is protected by t-butyl.
MOD_RES                 12
                        note = The sidechain of serine is protected by t-butyl.
MOD_RES                 18
                        note = The sidechain of serine is protected by t-butyl.
MOD_RES                 18
                        note = Serine at position 18 is amidated as a C-terminal
                         primary amide.
source                  1..18
                        mol_type = protein
                        organism = synthetic construct
SEQUENCE: 20
FVQWLIAGGP SSGAPPPS                                             18

SEQ ID NO: 21           moltype = AA  length = 25
FEATURE                 Location/Qualifiers
REGION                  1..25
                        note = Synthetic Construct
MOD_RES                 1
                        note = The sidechain of aspartic acid is protected by
                         t-butyl.
MOD_RES                 2
                        note = The sidechain of lysine is protected by a
                         t-butyloxycarbonyl (Boc) protecting group.
MOD_RES                 5
                        note = The sidechain of glutamine is protected by a Trityl
                         (Trt) protecting group.
MOD_RES                 6
                        note = Lys at position 6 is chemically modified through
                         conjugation to the epsilon-amino group of the K side-chain
                         with
                         (2-[2-(2-Amino-ethoxy)-ethoxy]-acetyl)2-(gamma-Glu(t-butyl)
                         )1-CO-(CH2)18-CO2-(t-butyl).
MOD_RES                 10
                        note = The sidechain of glutamine is protected by a Trityl
                         (Trt) protecting group.
MOD_RES                 11
                        note = The sidechain of Tryptophan is protected by a
                         t-butyloxycarbonyl (Boc) protecting group.
MOD_RES                 18
                        note = The sidechain of serine is protected by t-butyl.
MOD_RES                 19
                        note = The sidechain of serine is protected by t-butyl.
MOD_RES                 25
                        note = The sidechain of serine is protected by t-butyl.
MOD_RES                 25
                        note = Serine at position 25 is amidated as a C-terminal
                         primary amide.
source                  1..25
                        mol_type = protein
                        organism = synthetic construct
SEQUENCE: 21
DKIAQKAFVQ WLIAGGPSSG APPPS                                     25

SEQ ID NO: 22           moltype = AA  length = 39
FEATURE                 Location/Qualifiers
REGION                  1..39
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
SITE                    2
```

```
                          note = X at position 2 is 2-Aminoisobutyric Acid (Aib)
MOD_RES                   3
                          note = The sidechain of glutamic acid is protected by
                           t-butyl.
MOD_RES                   5
                          note = The sidechain of threonine is protected by t-butyl.
MOD_RES                   7
                          note = The sidechain of threonine is protected by t-butyl.
MOD_RES                   8
                          note = The sidechain of serine is protected by t-butyl.
MOD_RES                   9
                          note = The sidechain of aspartic acid is protected by
                           t-butyl.
MOD_RES                   10
                          note = The sidechain of tyrosine is protected by t-butyl.
MOD_RES                   11
                          note = The sidechain of serine is protected by t-butyl.
SITE                      13
                          note = X at position 13 is 2-Aminoisobutyric Acid (Aib)
MOD_RES                   15
                          note = The sidechain of aspartic acid is protected by
                           t-butyl.
MOD_RES                   16
                          note = The sidechain of lysine is protected by a
                           t-butyloxycarbonyl (Boc) protecting group.
MOD_RES                   19
                          note = The sidechain of glutamine is protected by a Trityl
                           (Trt) protecting group.
MOD_RES                   20
                          note = Lys at position 20 is chemically modified through
                           conjugation to the epsilon-amino group of the K side-chain
                           with
                           (2-[2-(2-Amino-ethoxy)-ethoxy]-acetyl)2-(gamma-Glu(t-butyl)
                           )1-CO-(CH2)18-CO2-(t-butyl).
MOD_RES                   24
                          note = The sidechain of glutamine is protected by a Trityl
                           (Trt) protecting group.
MOD_RES                   25
                          note = The sidechain of Tryptophan is protected by a
                           t-butyloxycarbonyl (Boc) protecting group.
MOD_RES                   32
                          note = The sidechain of serine is protected by t-butyl.
MOD_RES                   33
                          note = The sidechain of serine is protected by t-butyl.
MOD_RES                   39
                          note = The sidechain of serine is protected by t-butyl.
MOD_RES                   39
                          note = Serine at position 39 is amidated as a C-terminal
                           primary amide.
source                    1..39
                          mol_type = protein
                          organism = synthetic construct
SEQUENCE: 22
YXEGTFTSDY SIXLDKIAQK AFVQWLIAGG PSSGAPPPS                          39

SEQ ID NO: 23             moltype = AA  length = 39
FEATURE                   Location/Qualifiers
REGION                    1..39
                          note = Synthetic Construct
MOD_RES                   1
                          note = N-terminus is protected by (t-butyloxycarbonyl) Boc.
MOD_RES                   1
                          note = The sidechain of tyrosine is protected by t-butyl.
MOD_RES                   3
                          note = The sidechain of glutamic acid is protected by
                           t-butyl.
MOD_RES                   5
                          note = The sidechain of threonine is protected by t-butyl.
MOD_RES                   7
                          note = The sidechain of threonine is protected by t-butyl.
MOD_RES                   8
                          note = The sidechain of serine is protected by t-butyl.
MOD_RES                   9
                          note = The sidechain of aspartic acid is protected by
                           t-butyl.
MOD_RES                   10
                          note = The sidechain of tyrosine is protected by t-butyl.
MOD_RES                   11
                          note = The sidechain of serine is protected by t-butyl.
```

-continued

```
MOD_RES                 15
                        note = The sidechain of aspartic acid is protected by
                         t-butyl.
MOD_RES                 16
                        note = The sidechain of lysine is protected by a
                         t-butyloxycarbonyl (Boc) protecting group.
MOD_RES                 19
                        note = The sidechain of glutamine is protected by a Trityl
                         (Trt) protecting group.
MOD_RES                 20
                        note = The epsilon amino group of K is modified with
                         5,5-dimethyl-2-(3-methylbutylidene)cyclohexane-1,3-dione
MOD_RES                 24
                        note = The sidechain of glutamine is protected by a Trityl
                         (Trt) protecting group.
MOD_RES                 25
                        note = The sidechain of Tryptophan is protected by a
                         t-butyloxycarbonyl (Boc) protecting group.
MOD_RES                 32
                        note = The sidechain of serine is protected by t-butyl.
MOD_RES                 33
                        note = The sidechain of serine is protected by t-butyl.
MOD_RES                 39
                        note = The sidechain of serine is protected by t-butyl.
MOD_RES                 39
                        note = The C-terminal serine is amidated and is bound to
                         Sieber resin through this amine group.
source                  1..39
                        mol_type = protein
                        organism = synthetic construct
SITE                    13
                        note = X at position 13 is 2-Aminoisobutyric Acid (Aib)
SITE                    2
                        note = X at position 2 is 2-Aminoisobutyric Acid (Aib)
SEQUENCE: 23
YXEGTFTSDY SIXLDKIAQK AFVQWLIAGG PSSGAPPPS                         39

SEQ ID NO: 24           moltype = AA  length = 39
FEATURE                 Location/Qualifiers
REGION                  1..39
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
SITE                    2
                        note = X at position 2 is 2-Aminoisobutyric Acid (Aib)
MOD_RES                 3
                        note = The sidechain of glutamic acid is protected by
                         t-butyl.
MOD_RES                 5
                        note = The sidechain of threonine is protected by t-butyl.
MOD_RES                 7
                        note = The sidechain of threonine is protected by t-butyl.
MOD_RES                 8
                        note = The sidechain of serine is protected by t-butyl.
MOD_RES                 9
                        note = The sidechain of aspartic acid is protected by
                         t-butyl.
MOD_RES                 10
                        note = The sidechain of tyrosine is protected by t-butyl.
MOD_RES                 11
                        note = The sidechain of serine is protected by t-butyl.
SITE                    13
                        note = X at position 13 is 2-Aminoisobutyric Acid (Aib)
MOD_RES                 15
                        note = The sidechain of aspartic acid is protected by
                         t-butyl.
MOD_RES                 16
                        note = The sidechain of lysine is protected by a
                         t-butyloxycarbonyl (Boc) protecting group.
MOD_RES                 19
                        note = The sidechain of glutamine is protected by a Trityl
                         (Trt) protecting group.
MOD_RES                 24
                        note = The sidechain of glutamine is protected by a Trityl
                         (Trt) protecting group.
MOD_RES                 25
                        note = The sidechain of Tryptophan is protected by a
```

```
                         t-butyloxycarbonyl (Boc) protecting group.
MOD_RES                 32
                        note = The sidechain of serine is protected by t-butyl.
MOD_RES                 33
                        note = The sidechain of serine is protected by t-butyl.
MOD_RES                 39
                        note = The sidechain of serine is protected by t-butyl.
MOD_RES                 39
                        note = The C-terminal serine is amidated and is bound to
                         Sieber resin through this amine group.
source                  1..39
                        mol_type = protein
                        organism = synthetic construct
SEQUENCE: 24
YXEGTFTSDY SIXLDKIAQK AFVQWLIAGG PSSGAPPPS                         39

SEQ ID NO: 25           moltype = AA  length = 10
FEATURE                 Location/Qualifiers
REGION                  1..10
                        note = Synthetic Construct
MOD_RES                 3
                        note = The sidechain of serine is protected by t-butyl.
MOD_RES                 4
                        note = The sidechain of serine is protected by t-butyl.
MOD_RES                 10
                        note = The sidechain of serine is protected by t-butyl.
MOD_RES                 10
                        note = Serine at position 10 is amidated as a C-terminal
                         primary amide.
source                  1..10
                        mol_type = protein
                        organism = synthetic construct
SEQUENCE: 25
GPSSGAPPPS                                                         10

SEQ ID NO: 26           moltype = AA  length = 8
FEATURE                 Location/Qualifiers
REGION                  1..8
                        note = Synthetic Construct
MOD_RES                 1
                        note = N-terminus is protected by Fmoc.
MOD_RES                 3
                        note = The sidechain of glutamine is protected by a Trityl
                         (Trt) protecting group.
MOD_RES                 4
                        note = The sidechain of Tryptophan is protected by a
                         t-butyloxycarbonyl (Boc) protecting group.
source                  1..8
                        mol_type = protein
                        organism = synthetic construct
SEQUENCE: 26
FVQWLIAG                                                           8

SEQ ID NO: 27           moltype = AA  length = 18
FEATURE                 Location/Qualifiers
REGION                  1..18
                        note = Synthetic Construct
MOD_RES                 3
                        note = The sidechain of glutamine is protected by a Trityl
                         (Trt) protecting group.
MOD_RES                 4
                        note = The sidechain of Tryptophan is protected by a
                         t-butyloxycarbonyl (Boc) protecting group.
MOD_RES                 11
                        note = The sidechain of serine is protected by t-butyl.
MOD_RES                 12
                        note = The sidechain of serine is protected by t-butyl.
MOD_RES                 18
                        note = The sidechain of serine is protected by t-butyl.
MOD_RES                 18
                        note = Serine at position 18 is amidated as a C-terminal
                         primary amide.
source                  1..18
                        mol_type = protein
                        organism = synthetic construct
SEQUENCE: 27
FVQWLIAGGP SSGAPPPS                                                18

SEQ ID NO: 28           moltype = AA  length = 7
```

-continued

```
FEATURE                 Location/Qualifiers
REGION                  1..7
                        note = Synthetic Construct
MOD_RES                 1
                        note = N-terminus is protected by Fmoc.
MOD_RES                 1
                        note = The sidechain of aspartic acid is protected by
                         t-butyl.
MOD_RES                 2
                        note = The sidechain of lysine is protected by a
                         t-butyloxycarbonyl (Boc) protecting group.
MOD_RES                 5
                        note = The sidechain of glutamine is protected by a Trityl
                         (Trt) protecting group.
MOD_RES                 6
                        note = Lys at position 6 is chemically modified through
                         conjugation to the epsilon-amino group of the K side-chain
                         with
                         (2-[2-(2-Amino-ethoxy)-ethoxy]-acetyl)2-(gamma-Glu(t-butyl)
                         )1-CO-(CH2)18-CO2-(t-butyl).
source                  1..7
                        mol_type = protein
                        organism = synthetic construct
SEQUENCE: 28
DKIAQKA                                                                    7

SEQ ID NO: 29           moltype = AA  length = 25
FEATURE                 Location/Qualifiers
REGION                  1..25
                        note = Synthetic Construct
MOD_RES                 1
                        note = The sidechain of aspartic acid is protected by
                         t-butyl.
MOD_RES                 2
                        note = The sidechain of lysine is protected by a
                         t-butyloxycarbonyl (Boc) protecting group.
MOD_RES                 5
                        note = The sidechain of glutamine is protected by a Trityl
                         (Trt) protecting group.
MOD_RES                 6
                        note = Lys at position 6 is chemically modified through
                         conjugation to the epsilon-amino group of the K side-chain
                         with
                         (2-[2-(2-Amino-ethoxy)-ethoxy]-acetyl)2-(gamma-Glu(t-butyl)
                         )1-CO-(CH2)18-CO2-(t-butyl).
MOD_RES                 10
                        note = The sidechain of glutamine is protected by a Trityl
                         (Trt) protecting group.
MOD_RES                 11
                        note = The sidechain of Tryptophan is protected by a
                         t-butyloxycarbonyl (Boc) protecting group.
MOD_RES                 18
                        note = The sidechain of serine is protected by t-butyl.
MOD_RES                 19
                        note = The sidechain of serine is protected by t-butyl.
MOD_RES                 25
                        note = The sidechain of serine is protected by t-butyl.
MOD_RES                 25
                        note = Serine at position 25 is amidated as a C-terminal
                         primary amide.
source                  1..25
                        mol_type = protein
                        organism = synthetic construct
SEQUENCE: 29
DKIAQKAFVQ WLIAGGPSSG APPPS                                                25

SEQ ID NO: 30           moltype = AA  length = 14
FEATURE                 Location/Qualifiers
REGION                  1..14
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
SITE                    2
                        note = X at position 2 is 2-Aminoisobutyric Acid (Aib)
MOD_RES                 3
                        note = The sidechain of glutamic acid is protected by
                         t-butyl.
```

-continued

```
MOD_RES                 5
                        note = The sidechain of threonine is protected by t-butyl.
MOD_RES                 7
                        note = The sidechain of threonine is protected by t-butyl.
MOD_RES                 8
                        note = The sidechain of serine is protected by t-butyl.
MOD_RES                 9
                        note = The sidechain of aspartic acid is protected by
                         t-butyl.
MOD_RES                 10
                        note = The sidechain of tyrosine is protected by t-butyl.
MOD_RES                 11
                        note = The sidechain of serine is protected by t-butyl.
SITE                    13
                        note = X at position 13 is 2-Aminoisobutyric Acid (Aib)
source                  1..14
                        mol_type = protein
                        organism = synthetic construct
SEQUENCE: 30
YXEGTFTSDY SIXL                                                   14

SEQ ID NO: 31           moltype = AA  length = 39
FEATURE                 Location/Qualifiers
REGION                  1..39
                        note = Synthetic Construct
MOD_RES                 1
                        note = N-terminus is protected by (t-butyloxycarbonyl) Boc.
MOD_RES                 1
                        note = The sidechain of tyrosine is protected by t-butyl.
SITE                    2
                        note = X at position 2 is 2-Aminoisobutyric Acid (Aib)
MOD_RES                 3
                        note = The sidechain of glutamic acid is protected by
                         t-butyl.
MOD_RES                 5
                        note = The sidechain of threonine is protected by t-butyl.
MOD_RES                 7
                        note = The sidechain of threonine is protected by t-butyl.
MOD_RES                 8
                        note = The sidechain of serine is protected by t-butyl.
MOD_RES                 9
                        note = The sidechain of aspartic acid is protected by
                         t-butyl.
MOD_RES                 10
                        note = The sidechain of tyrosine is protected by t-butyl.
MOD_RES                 11
                        note = The sidechain of serine is protected by t-butyl.
SITE                    13
                        note = X at position 13 is 2-Aminoisobutyric Acid (Aib)
MOD_RES                 15
                        note = The sidechain of aspartic acid is protected by
                         t-butyl.
MOD_RES                 16
                        note = The sidechain of lysine is protected by a
                         t-butyloxycarbonyl (Boc) protecting group.
MOD_RES                 19
                        note = The sidechain of glutamine is protected by a Trityl
                         (Trt) protecting group.
MOD_RES                 20
                        note = Lys at position 20 is chemically modified through
                         conjugation to the epsilon-amino group of the K side-chain
                         with
                         (2-[2-(2-Amino-ethoxy)-ethoxy]-acetyl)2-(gamma-Glu(t-butyl)
                         )1-CO-(CH2)18-CO2-(t-butyl).
MOD_RES                 24
                        note = The sidechain of glutamine is protected by a Trityl
                         (Trt) protecting group.
MOD_RES                 25
                        note = The sidechain of Tryptophan is protected by a
                         t-butyloxycarbonyl (Boc) protecting group.
MOD_RES                 32
                        note = The sidechain of serine is protected by t-butyl.
MOD_RES                 33
                        note = The sidechain of serine is protected by t-butyl.
MOD_RES                 39
                        note = The sidechain of serine is protected by t-butyl.
MOD_RES                 39
                        note = Serine at position 39 is amidated as a C-terminal
                         primary amide.
```

-continued

```
source                1..39
                      mol_type = protein
                      organism = synthetic construct
SEQUENCE: 31
YXEGTFTSDY SIXLDKIAQK AFVQWLIAGG PSSGAPPPS                        39

SEQ ID NO: 32         moltype = AA  length = 17
FEATURE               Location/Qualifiers
REGION                1..17
                      note = Synthetic Construct
SITE                  2
                      note = X at position 2 is 2-Aminoisobutyric Acid (Aib)
SITE                  13
                      note = X at position 13 is 2-Aminoisobutyric Acid (Aib)
MOD_RES               17
                      note = The C-terminal hydroxyl of Isoleucine is modified
                       with hydrazide (N-NH2)
source                1..17
                      mol_type = protein
                      organism = synthetic construct
SEQUENCE: 32
YXEGTFTSDY SIXLDKI                                                17

SEQ ID NO: 33         moltype = AA  length = 22
FEATURE               Location/Qualifiers
REGION                1..22
                      note = Synthetic Construct
MOD_RES               3
                      note = Lys at position 3 is chemically modified through
                       conjugation to the epsilon-amino group of the K side-chain
                       with
                       (2-[2-(2-Amino-ethoxy)-ethoxy]-acetyl)2-(gamma-Glu)1-CO-(CH
                       2)18-CO2H
MOD_RES               22
                      note = Ser at position 22 is amidated as a C-terminal
                       primary amide
source                1..22
                      mol_type = protein
                      organism = synthetic construct
SEQUENCE: 33
CQKAFVQWLI AGGPSSGAPP PS                                          22

SEQ ID NO: 34         moltype = AA  length = 17
FEATURE               Location/Qualifiers
REGION                1..17
                      note = Synthetic Construct
SITE                  2
                      note = X at position 2 is 2-Aminoisobutyric Acid (Aib)
SITE                  13
                      note = X at position 13 is 2-Aminoisobutyric Acid (Aib)
MOD_RES               17
                      note = The C terminal hydroxyl is modified with S-CH2-CF3
source                1..17
                      mol_type = protein
                      organism = synthetic construct
SEQUENCE: 34
YXEGTFTSDY SIXLDKI                                                17

SEQ ID NO: 35         moltype = AA  length = 39
FEATURE               Location/Qualifiers
REGION                1..39
                      note = Synthetic Construct
SITE                  2
                      note = X at position 2 is 2-Aminoisobutyric Acid (Aib)
SITE                  13
                      note = X at position 13 is 2-Aminoisobutyric Acid (Aib)
MOD_RES               20
                      note = Lys at position 20 is chemically modified through
                       conjugation to the epsilon-amino group of the K side-chain
                       with
                       (2-[2-(2-Amino-ethoxy)-ethoxy]-acetyl)2-(gamma-Glu)1-CO-(CH
                       2)18-CO2H
MOD_RES               39
                      note = Ser at position 39 is amidated as a C-terminal
                       primary amide
source                1..39
                      mol_type = protein
                      organism = synthetic construct
SEQUENCE: 35
```

-continued

```
YXEGTFTSDY SIXLDKICQK AFVQWLIAGG PSSGAPPPS                   39

SEQ ID NO: 36          moltype = AA  length = 20
FEATURE                Location/Qualifiers
REGION                 1..20
                       note = Synthetic Construct
SITE                   2
                       note = MISC_FEATURE - Xaa at position 2 is Aib
SITE                   13
                       note = MISC_FEATURE - Xaa at position 13 is Aib
MOD_RES                20
                       note = Lys at position 20 is chemically modified through
                        conjugation to the epsilon-amino group of the K side-chain
                        with
                        (2-[2-(2-Amino-ethoxy)-ethoxy]-acetyl)2-(gamma-Glu)1-CO-(CH
                        2)18-CO2H
MOD_RES                20
                       note = The C-terminal hydroxyl is modified with hydrazide
                        (-N-NH2)
source                 1..20
                       mol_type = protein
                       organism = synthetic construct
SEQUENCE: 36
YXEGTFTSDY SIXLDKIAQK                                        20

SEQ ID NO: 37          moltype = AA  length = 19
FEATURE                Location/Qualifiers
REGION                 1..19
                       note = Synthetic Construct
MOD_RES                19
                       note = Ser at position 19 is amidated as a C-terminal
                        primary amide
source                 1..19
                       mol_type = protein
                       organism = synthetic construct
SEQUENCE: 37
CFVQWLIAGG PSSGAPPPS                                         19

SEQ ID NO: 38          moltype = AA  length = 20
FEATURE                Location/Qualifiers
REGION                 1..20
                       note = Synthetic Construct
SITE                   2
                       note = X at position 2 is 2-Aminoisobutyric Acid (Aib)
SITE                   13
                       note = X at position 13 is 2-Aminoisobutyric Acid (Aib)
MOD_RES                20
                       note = Lys at position 20 is chemically modified through
                        conjugation to the epsilon-amino group of the K side-chain
                        with
                        (2-[2-(2-Amino-ethoxy)-ethoxy]-acetyl)2-(gamma-Glu)1-CO-(CH
                        2)18-CO2H
MOD_RES                20
                       note = The C-terminal hydroxyl is modified with
                        4-mercaptophenylacetic acid
source                 1..20
                       mol_type = protein
                       organism = synthetic construct
SEQUENCE: 38
YXEGTFTSDY SIXLDKIAQK                                        20

SEQ ID NO: 39          moltype = AA  length = 39
FEATURE                Location/Qualifiers
REGION                 1..39
                       note = Synthetic Construct
SITE                   2
                       note = X at position 2 is 2-Aminoisobutyric Acid (Aib)
SITE                   13
                       note = X at position 13 is 2-Aminoisobutyric Acid (Aib)
MOD_RES                20
                       note = Lys at position 20 is chemically modified through
                        conjugation to the epsilon-amino group of the K side-chain
                        with
                        (2-[2-(2-Amino-ethoxy)-ethoxy]-acetyl)2-(gamma-Glu)1-CO-(CH
                        2)18-CO2H
MOD_RES                39
                       note = Ser at position 39 is amidated as a C-terminal
                        primary amide
source                 1..39
```

-continued

```
                        mol_type = protein
                        organism = synthetic construct
SEQUENCE: 39
YXEGTFTSDY SIXLDKIAQK CFVQWLIAGG PSSGAPPPS                    39

SEQ ID NO: 40           moltype = AA  length = 39
FEATURE                 Location/Qualifiers
REGION                  1..39
                        note = Synthetic Construct
SITE                    2
                        note = X at position 2 is 2-Aminoisobutyric Acid (Aib)
MOD_RES                 7..8
                        note = Thr at position 7 and Ser at position 8 form a depsi
                         peptide
SITE                    13
                        note = X at position 13 is 2-Aminoisobutyric Acid (Aib)
MOD_RES                 20
                        note = Lys at position 20 is chemically modified through
                         conjugation to the epsilon-amino group of the K side-chain
                         with
                         (2-[2-(2-Amino-ethoxy)-ethoxy]-acetyl)2-(gamma-Glu)1-CO-(CH
                         2)18-CO2H
MOD_RES                 39
                        note = Ser at position 39 is amidated as a C-terminal
                         primary amide
source                  1..39
                        mol_type = protein
                        organism = synthetic construct
SEQUENCE: 40
YXEGTFXXDY SIXLDKIAQK AFVQWLIAGG PSSGAPPPS                    39
```